US006939546B2

(12) United States Patent
Nauss et al.

(10) Patent No.: US 6,939,546 B2
(45) Date of Patent: *Sep. 6, 2005

(54) MODEL FOR TESTING IMMUNOGENICITY OF PEPTIDES

(75) Inventors: Jeffrey Nauss, San Diego, CA (US); Robert Reid, Fairfield, PA (US); Marcia Kay Wolf, Silver Spring, MD (US); Scheberazade Sadegh-Nasseri, Baltimore, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/013,077

(22) Filed: Jan. 26, 1998

(65) Prior Publication Data

US 2003/0082193 A1 May 1, 2003

Related U.S. Application Data

(63) Continuation-in-part of application No. 08/798,734, filed on Jan. 27, 1997, now Pat. No. 6,309,669, which is a continuation-in-part of application No. 08/590,973, filed on Jan. 24, 1996, now abandoned, which is a continuation-in-part of application No. 08/247,884, filed on May 23, 1994, now abandoned, which is a continuation-in-part of application No. 08/064,559, filed on May 21, 1993, now abandoned.

(51) Int. Cl.[7] .................... A61K 39/00; G01N 33/543
(52) U.S. Cl. .................... 424/184.1; 424/185.1; 514/13; 514/14
(58) Field of Search .................... 424/184.1, 185.1; 514/14, 13

(56) References Cited

U.S. PATENT DOCUMENTS

| | | | |
|---|---|---|---|
| 3,540,444 A | 11/1970 | Moreland | 128/173 |
| 3,773,919 A | 11/1973 | Boswell | 424/19 |
| 3,788,315 A | 1/1974 | Laurens | 128/173 H |
| 4,166,800 A | 9/1979 | Fong | 252/316 |
| 4,384,975 A | 5/1983 | Fong | 427/213.36 |
| 4,530,840 A | 7/1985 | Tice et al. | 514/179 |
| 4,542,025 A | 9/1985 | Tice et al. | 424/78 |
| 4,585,482 A | 4/1986 | Tice et al. | 106/15.05 |
| 4,622,244 A | 11/1986 | Lapka et al. | 427/213.32 |
| 4,637,905 A | 1/1987 | Gardner | 264/4.3 |
| 4,675,189 A | 6/1987 | Kent et al. | 424/490 |
| 4,798,786 A | 1/1989 | Tice et al. | 435/177 |
| 4,835,139 A | 5/1989 | Tice et al. | 514/15 |
| 4,863,735 A | 9/1989 | Kohn et al. | 524/422 |
| 4,897,268 A | 1/1990 | Tice et al. | 424/422 |
| 4,938,763 A | 7/1990 | Dunn et al. | 604/891.1 |
| 4,941,880 A | 7/1990 | Burns | 604/143 |
| 5,000,886 A | 3/1991 | Lawter et al. | 264/4.3 |
| 5,019,096 A | 5/1991 | Fox, Jr. et al. | 623/1 |
| 5,059,187 A | 10/1991 | Sperry et al. | 604/290 |
| 5,064,413 A | 11/1991 | McKinnon et al. | 604/70 |
| 5,075,109 A | 12/1991 | Tice et al. | 424/88 |
| 5,102,872 A | 4/1992 | Singh et al. | 514/21 |
| 5,129,825 A | 7/1992 | Discko, Jr. | 433/90 |
| 5,133,701 A | 7/1992 | Han | 604/289 |
| 5,236,355 A | 8/1993 | Brizzolara et al. | 433/80 |
| 5,278,202 A | 1/1994 | Dunn et al. | 523/113 |
| 5,290,494 A | 3/1994 | Coombes et al. | 264/41 |
| 5,360,610 A | 11/1994 | Tice et al. | 424/426 |
| 5,384,133 A | 1/1995 | Boyes et al. | 424/501 |
| 5,407,609 A | 4/1995 | Tice et al. | 264/46 |
| 5,417,986 A | 5/1995 | Reid et al. | 424/499 |
| 5,424,289 A * | 6/1995 | Yang et al. | 514/12 |
| 5,429,822 A | 7/1995 | Gresser et al. | 424/426 |
| 5,500,228 A | 3/1996 | Lawter et al. | 424/486 |
| 5,538,739 A | 7/1996 | Bodmer et al. | 424/501 |
| 5,639,480 A | 6/1997 | Bodmer et al. | 424/501 |
| 5,643,605 A | 7/1997 | Cleland et al. | 424/489 |
| 5,648,096 A | 7/1997 | Gander et al. | 424/489 |
| 5,650,173 A | 7/1997 | Ramstack et al. | 424/489 |
| 5,688,530 A | 11/1997 | Bodmer et al. | 424/501 |
| 5,693,343 A | 12/1997 | Reid et al. | 424/491 |
| 5,762,965 A | 6/1998 | Burnett et al. | 424/499 |
| 5,811,128 A | 9/1998 | Tice et al. | 424/501 |
| 5,814,344 A | 9/1998 | Tice et al. | 424/501 |
| 5,820,883 A | 10/1998 | Tice et al. | 424/501 |
| 5,853,763 A | 12/1998 | Tice et al. | 424/489 |
| 6,309,669 B1 * | 10/2001 | Setterstrom et al. | 424/486 |

FOREIGN PATENT DOCUMENTS

EP          0052510 B2    10/1994    ............ A61K/9/50

OTHER PUBLICATIONS

Chicz et al, Nature, 358, (Aug. 27, 1992), 769–768.*

Nauss et al, Jornl. of Immunology, vol. 150/ No. 8, Part II, (Apr. 15, 1993).*

Busch et al, The Jornl. of Immunology, vol. 147, 4, 1292–98, (8/91).*

Tang et al, Jrnl. of Virology, 62(12), 4745–51, (12/88).*

Jackson et al, Dept. Res., 4(3), (1991), 114–24.*

Rothbard et al, Bacterial Protein Toxins, 261 Bakt. Suppl. 19, (1989), 437–45.*

Gilding, Biodegradable polymers for use in surgery–polyglycolic/poly (ac c acid) homo– and copolymers: 1, Polymer, vol. 20, Dec. 1979, pp 1459–1464.

Biotechnology News, Aug. 22, 1997, vol. 17, No. 20, Topical DNA vaccine elicits immune response.

(Continued)

Primary Examiner—Bennett Celsa
(74) Attorney, Agent, or Firm—Elizabeth Arwine

(57) ABSTRACT

Assay methods for determining whether a peptide is likely to be immunogenic are based on a computer modeling of binding to a Class II MHC DR1 receptor. This is confirmed by competitive inhibition binding assays. The peptides are useful for eliciting an immune response for vaccination or the production of antibodies or T-cells.

12 Claims, 32 Drawing Sheets

OTHER PUBLICATIONS

Hall, et al., Purification and Analysis of Colonization Factor Antigen I, Coli Surface Antigen 1, and Coli Surface ANtigen 3 Fimbriae from Enterotoxigenic *Escherichia coli*, Journal of Bacteriology, Nov. 1989, p6372–6374, vol. 171, No. 11.

Evans, et al. Purification and Characterization of the CFR/I Antigen of Enterotoxigenic *Escherichia coli*, Infection and Immunity, Aug. 1979, p 738–748, vol. 25.

Karjalainen, et al., Molecular Cloning and Nucleotide Sequence of the Colonization Factor Antigen I Gene of *Escherichia coli*, Infection and Immunity, Apr. 1989, p1126–1130, vol. 57.

Jeyanthi, et al., Novel, Burst Free Programmable Biodegradable Microspheres For Controlled Release of Polypeptides, Proceedings Int. Symp. control Release Bioact. Mater. (1996) p351–352/.

Yeh, A novel emulsification–solvent extraction technique for production of protein loaded biodegradable microparticles for vaccine and drug delivery, Journal of Controlled Release, 33 (1005) 437–445.

Yan, Characterization and morphological analysis of protein–loaded poly(lactide–co–glycolide) microparticles prepared by watewr–in–oil–in–water emulsion technique, Journal of Controlled Release, 32 (1994) 231–241.

Wang, et al., Influence of formulation methods on the in vitro controlled release of protein from poly (ester) microspheres Journal of Controlled Release, 17 (1991) 23–32.

Brown, Wonder Drugs' Losing Healing Aura, The Washing Post, Jun. 26, 1995, A section.

Setterstrom, Controlled Release of Antibiotics From biodegradable Microcapsules For Wound infection Control, Chemical Abstracts, 1983, pp215–226.

Perez–Casal, et al., Gene Encoding the Major Subunit of CS1 Pili of Human Enterotoxigenic *Escherichia coli*, Infection and Immunity, Nov., 1990, p 3594–3600, vol. 58, No. 11.

Jordi, et al., Analysis of the first two genes of the CS1 fimbrial operon in human enterotoxigenic *Escherichia coli* of serotype 0139: H28, FEMS Microbiology Letters 80, (1991) p265–270.

Tan, et al., Mapping the Antigenic Epitopes of Human Dihydrofolate Reductase by systematic Synthesis of Peptides on solid Supports, The Journal of Biological Chemistry, vol. 265, No. 14, Issue of May 15, pp. 8022–8026 (1990).

McConnel, et al., Antigenic homology within human enterotoxigenic *Esherichia coli* fimbrial colonization factor antigens: CFA/I, coli–surface–associated antigens (CS)1,CS2, CS4 and CS17, FEMS Microbiology Letters 61 (1989) 105–108.

Van der Zee, Efficient mapping and characterization of a T cell epitope by the simultaneous synthesis of multiple peptides, Eur. J. Immunol. 1989, 19: 43–47.

Cassels, et al., Analysis of *Escherichia coli* Colonization Factor Antigen I Linear B–Cell Epitopes, as Determined by Primate Responses, following Protein Sequence Verification, Infection and Immunity, Jun. 1992, p. 2174–2181, vol. 60, No. 6.

Romagnoli, et al. Peptide–MHC Interaction: A Rational Approach to Vaccine Design, Inter, RE. Immunol. 6, 1990, 00 61–73.

Maister, First Oral AIDS Vaccine Trials Near, BioWorld Today, Tuesday, Apr. 19, 1994, p. 4.

Rognan, et al., Molecular Modeling of an Antigenic Complex Between a Viral Peptide and a Class I Major Histocompatibility Glycoprotein, Proteins Structure, Function and Genetics 13 70–85 (1992).

Brown, A hypothetical model of the foreign antigen biinding site of Class II histocompatibility molecules, Nature, vol. 332, Apr. 28, 1988, p845–850.

The Journal of Immunology, vol. 150, No. 8, Part II, Apr. 1993, Nauss et al., Binding Interactions of Peptides in a Structural Homology Model of the DR1 Class MHC, pp. 41A, Abstract 221.

Nature, vol. 358, Issued Aug. 27, 1992, Chiez et al., Predominant Nturally processed Peptides Bound to HLA DR1 are derived from MHC–related Molecule and are Heterogenous in Size, pp. 764–768.

The Journal of Immunology, vol. 150, No. 2, issued Jan. 15, 1993, Boehncke et al., The Importance of Dominant Negative Effects of Amino Acid Side Chain substitution in Peptide–MHC Molecule Interations and T Cell Recognition, pp. 331–341, see Abstract.

The EMBO Journal, vol. 9, No. 6, issued 1990, jardetsky et al., Peptide binding to HLA–DR1: A Peptide with most residues substituted to alanine retains MHC binding, pp. 1797–1803.

Nature, vol. 332, Apr. 28, 1988, Brown et al., A hypothetical model of the foreign antigen binding site of Class II histocompatibility molecules, pp. 845–850.

\* cited by examiner

FIG. 1

```
* MINIMIZED COORDINATES FROM CHARMM
* DATE:     2/25/93     14:    18        CREATED BY USER: nbuss
*
1639
    1    1 ILE  N    -53.41835 -52.07964  96.86949 A1    1    0.00000
    2    1 ILE  HT1  -54.06550 -53.37379  96.22549 A1    1    0.00000
    3    1 ILE  HT2  -52.48505 -53.33354  96.89426 A1    1    0.00000
    4    1 ILE  HT3  -53.81151 -52.85195  97.84341 A1    1    0.00000
    5    1 ILE  CA   -53.29159 -51.45945  96.52548 A1    1    0.00000
    6    1 ILE  CB   -54.51076 -51.09296  95.64551 A1    1    0.00000
    7    1 ILE  CG2  -55.84867 -51.39510  96.33544 A1    1    0.00000
    8    1 ILE  CG1  -54.43380 -49.65164  95.12978 A1    1    0.00000
    9    1 ILE  CD   -55.55018 -49.30658  94.14124 A1    1    0.00000
   10    1 ILE  C    -53.31306 -50.79352  97.88119 A1    1    0.00000
   11    1 ILE  O    -53.76732 -51.45486  98.80000 A1    1    0.00000
   12    2 LYS  N    -52.70566 -49.57271  97.98462 A1    2    0.00000
   13    2 LYS  H    -52.43149 -49.07042  97.19065 A1    2    0.00000
   14    2 LYS  CA   -52.72856 -48.82990  99.24363 A1    2    0.00000
   15    2 LYS  CB   -51.40674 -49.22996 100.05168 A1    2    0.00000
   16    2 LYS  CG   -51.65942 -50.46422 100.94226 A1    2    0.00000
   17    2 LYS  CD   -50.39491 -50.76541 101.74483 A1    2    0.00000
   18    2 LYS  CE   -50.65567 -51.67024 102.94896 A1    2    0.00000
   19    2 LYS  NZ   -49.48784 -51.62033 103.84066 A1    2    0.00000
   20    2 LYS  HZ1  -49.68891 -52.15413 104.71032 A1    2    0.00000
   21    2 LYS  HZ2  -48.66152 -52.03086 103.36182 A1    2    0.00000
   22    2 LYS  HZ3  -49.20787 -50.62063 104.08530 A1    2    0.00000
   23    2 LYS  C    -52.58080 -47.37619  98.05749 A1    2    0.00000
   24    2 LYS  O    -52.16561 -47.08993  97.74074 A1    2    0.00000
   25    3 GLU  N    -52.93375 -46.48610  99.78817 A1    3    0.00000
   26    3 GLU  H    -53.25920 -46.74733 100.69754 A1    3    0.00000
   27    3 GLU  CA   -52.88416 -45.05669  99.49342 A1    3    0.00000
   28    3 GLU  CB   -54.17633 -44.67728  98.75869 A1    3    0.00000
   29    3 GLU  CG   -54.16941 -43.30721  98.07127 A1    3    0.00000
   30    3 GLU  CD   -55.38365 -43.14902  97.16830 A1    3    0.00000
   31    3 GLU  OE1  -55.40070 -42.20412  96.38367 A1    3    0.00000
   32    3 GLU  OE2  -56.30088 -43.96983  97.23742 A1    3    0.00000
   33    3 GLU  C    -52.73723 -44.30588 100.80334 A1    3    0.00000
   34    3 GLU  O    -53.13310 -44.80269 101.85375 A1    3    0.00000
   35    4 GLU  N    -52.10513 -43.13147 100.72198 A1    4    0.00000
   36    4 GLU  H    -51.89913 -42.70887  99.83885 A1    4    0.00000
   37    4 GLU  CA   -51.71490 -42.41569 101.93532 A1    4    0.00000
   38    4 GLU  CB   -50.23606 -42.65775 102.23912 A1    4    0.00000
   39    4 GLU  CG   -49.88908 -44.07273 102.69972 A1    4    0.00000
   40    4 GLU  CD   -48.39447 -44.20822 102.86978 A1    4    0.00000
   41    4 GLU  OE1  -47.71593 -43.20739 103.12446 A1    4    0.00000
   42    4 GLU  OE2  -47.87485 -45.31626 102.72475 A1    4    0.00000
   43    4 GLU  C    -51.86859 -40.92476 101.75610 A1    4    0.00000
   44    4 GLU  O    -51.85445 -40.40438 100.64776 A1    4    0.00000
   45    5 HIS  N    -51.98758 -40.25490 102.89941 A1    5    0.00000
   46    5 HIS  H    -51.95529 -40.74179 103.77267 A1    5    0.00000
   47    5 HIS  CA   -52.02510 -38.79739 102.88794 A1    5    0.00000
   48    5 HIS  CB   -52.95268 -38.30654 104.00423 A1    5    0.00000
   49    5 HIS  CG   -54.39292 -38.58657 103.64511 A1    5    0.00000
   50    5 HIS  ND1  -55.01336 -38.04007 102.58831 A1    5    0.00000
   51    5 HIS  HD1  -54.63216 -37.40030 101.93314 A1    5    0.00000
   52    5 HIS  CD2  -55.29163 -39.42491 104.31043 A1    5    0.00000
   53    5 HIS  NE2  -56.46563 -39.37373 103.63249 A1    5    0.00000
   54    5 HIS  CE1  -56.29489 -38.51954 102.57197 A1    5    0.00000
   55    5 HIS  C    -50.64149 -38.20241 103.06558 A1    5    0.00000
   56    5 HIS  O    -49.75908 -38.78174 103.68940 A1    5    0.00000
   57    6 VAL  N    -50.46014 -37.02655 102.46317 A1    6    0.00000
   58    6 VAL  H    -51.22069 -36.59864 101.97707 A1    6    0.00000
   59    6 VAL  CA   -49.12695 -36.41474 102.46428 A1    6    0.00000
   60    6 VAL  CB   -48.60121 -35.23669 101.01420 A1    6    0.00000
```

FIG. 2

```
./CAL_KIN2.CRD        Thu Feb 25 14:58:48 1993        2

61   6 VAL  CG1  -47.(    2 -36.30119 101.00326 A1   6    0.00000
62   6 VAL  CG2  -49.16544 -37.46647 100.11057 A1    6    0.00000
63   6 VAL  C    -49.19435 -35.00190 103.02675 A1    6    0.00000
64   6 VAL  O    -50.21018 -34.34041 102.87457 A1    6    0.00000
65   7 ILE  N    -48.11527 -34.52120 103.65431 A1    7    0.00000
66   7 ILE  H    -47.35972 -35.13148 103.91409 A1    7    0.00000
67   7 ILE  CA   -48.09506 -33.08697 103.98819 A1    7    0.00000
68   7 ILE  CB   -48.69197 -32.86813 105.39701 A1    7    0.00000
69   7 ILE  CG2  -47.96322 -33.71317 106.43001 A1    7    0.00000
70   7 ILE  CG1  -48.74316 -31.39586 105.81727 A1    7    0.00000
71   7 ILE  CD   -49.28846 -31.20489 107.23523 A1    7    0.00000
72   7 ILE  C    -46.69381 -32.50114 103.87753 A1    7    0.00000
73   7 ILE  O    -45.72315 -33.10109 104.32366 A1    7    0.00000
74   8 ILE  N    -46.61414 -31.32789 103.23109 A1    8    0.00000
75   8 ILE  H    -47.43598 -30.79777 103.00074 A1    8    0.00000
76   8 ILE  CA   -45.31176 -30.85113 102.75879 A1    8    0.00000
77   8 ILE  CB   -45.18096 -31.21426 101.24826 A1    8    0.00000
78   8 ILE  CG2  -46.47692 -30.98133 100.47371 A1    8    0.00000
79   8 ILE  CG1  -44.01581 -30.53590 100.51961 A1    8    0.00000
80   8 ILE  CD   -42.65515 -30.85297 101.12422 A1    8    0.00000
81   8 ILE  C    -45.00402 -29.37643 103.03239 A1    8    0.00000
82   8 ILE  O    -45.69216 -28.63922 102.63903 A1    8    0.00000
83   9 GLN  N    -43.86371 -29.19466 103.70229 A1    9    0.00000
84   9 GLN  H    -43.33777 -29.97409 104.05676 A1    9    0.00000
85   9 GLN  CA   -43.27910 -27.85712 103.71549 A1    9    0.00000
86   9 GLN  CB   -42.97213 -27.43231 105.14730 A1    9    0.00000
87   9 GLN  CG   -44.24353 -27.13894 105.94550 A1    9    0.00000
88   9 GLN  CD   -43.92932 -26.69043 107.36355 A1    9    0.00000
89   9 GLN  OE1  -44.59992 -27.05224 108.31811 A1    9    0.00000
90   9 GLN  NE2  -42.89278 -25.86874 107.50418 A1    9    0.00000
91   9 GLN  HE21 -42.33586 -25.58069 106.73881 A1    9    0.00000
92   9 GLN  HE22 -42.66204 -25.53260 108.41526 A1    9    0.00000
93   9 GLN  C    -42.00840 -27.79728 102.89330 A1    9    0.00000
94   9 GLN  O    -41.07030 -28.56703 103.06902 A1    9    0.00000
95  10 ALA  N    -42.01720 -26.84230 101.96835 A1   10    0.00000
96  10 ALA  H    -42.80016 -26.24022 101.81084 A1   10    0.00000
97  10 ALA  CA   -40.93664 -26.60034 101.15833 A1   10    0.00000
98  10 ALA  CB   -41.09424 -26.95993  99.69281 A1   10    0.00000
99  10 ALA  C    -40.41733 -25.14834 101.25674 A1   10    0.00000
100 10 ALA  O    -41.21138 -24.24680 101.50542 A1   10    0.00000
101 11 GLU  N    -39.11637 -24.95043 101.08226 A1   11    0.00000
102 11 GLU  H    -38.51800 -25.72332 100.86462 A1   11    0.00000
103 11 GLU  CA   -38.56697 -23.61077 101.26935 A1   11    0.00000
104 11 GLU  CB   -37.61570 -23.62729 102.46404 A1   11    0.00000
105 11 GLU  CG   -30.29740 -24.15021 103.73032 A1   11    0.00000
106 11 GLU  CD   -37.31724 -24.35236 104.86668 A1   11    0.00000
107 11 GLU  OE1  -37.72498 -24.91514 105.87939 A1   11    0.00000
108 11 GLU  OE2  -36.15746 -23.95826 104.74301 A1   11    0.00000
109 11 GLU  C    -37.79619 -23.17941 100.04756 A1   11    0.00000
110 11 GLU  O    -37.17390 -23.99314  99.37097 A1   11    0.00000
111 12 PHE  N    -37.86688 -21.67280  99.78525 A1   12    0.00000
112 12 PHE  H    -38.38856 -21.25141 100.37827 A1   12    0.00000
113 12 PHE  CA   -37.20863 -21.33691  98.59813 A1   12    0.00000
114 12 PHE  CB   -38.26225 -21.06791  97.51950 A1   12    0.00000
115 12 PHE  CG   -37.93682 -21.86124  96.27668 A1   12    0.00000
116 12 PHE  CD1  -38.35291 -23.20899  96.17465 A1   12    0.00000
117 12 PHE  CD2  -37.21678 -21.25353  95.22261 A1   12    0.00000
118 12 PHE  CE1  -38.04712 -23.95258  95.01356 A1   12    0.00000
119 12 PHE  CE2  -36.91098 -21.99741  94.06122 A1   12    0.00000
120 12 PHE  CZ   -37.22685 -23.34453  93.96022 A1   12    0.00000
121 12 PHE  C    -36.45949 -20.05659  98.90209 A1   12    0.00000
122 12 PHE  O    -37.00216 -18.95008  98.93077 A1   12    0.00000
123 13 TYR  N    -35.16677 -20.22034  99.15293 A1   13    0.00000
124 13 TYR  H    -34.71888 -21.10856  99.03345 A1   13    0.00000
```

FIG. 3

```
/DR_HD2.CRD        Thu Feb 25 14:58:48 1993        3

125   13 TYR  CA   -34.44    -19.02891   99.57908 A1   13    1.00000
126   13 TYR  CB   -33.74    -19.31637  100.90471 A1   13    0.00000
127   13 TYR  CG   -33.63229 -18.04844  101.71489 A1   13    0.00000
128   13 TYR  CD1  -34.79192 -17.52707  102.32828 A1   13    0.00000
129   13 TYR  CE1  -34.69736 -16.35710  103.10470 A1   13    0.00000
130   13 TYR  CD2  -32.38328 -17.40687  101.86606 A1   13    0.00000
131   13 TYR  CE2  -32.29405 -16.23332  102.64552 A1   13    0.00000
132   13 TYR  CZ   -33.45188 -15.71594  103.26657 A1   13    0.00000
133   13 TYR  OH   -33.37191 -14.58930  104.06109 A1   13    0.00000
134   13 TYR  HH   -33.47343 -14.89238  104.98360 A1   13    0.00000
135   13 TYR  C    -33.46702 -18.52544   98.54525 A1   13    0.00000
136   13 TYR  O    -32.59456 -19.23915   98.06786 A1   13    0.00000
137   14 LEU  N    -33.65240 -17.25550   98.19697 A1   14    0.00000
138   14 LEU  H    -34.33538 -16.68306   98.64807 A1   14    0.00000
139   14 LEU  CA   -32.81168 -16.70428   97.14258 A1   14    0.00000
140   14 LEU  CB   -33.70274 -16.21044   96.00105 A1   14    0.00000
141   14 LEU  CG   -33.98219 -17.29674   94.96260 A1   14    0.00000
142   14 LEU  CD1  -35.16663 -16.92524   94.07539 A1   14    0.00000
143   14 LEU  CD2  -32.72461 -17.54798   94.13078 A1   14    0.00000
144   14 LEU  C    -31.93377 -15.56813   97.60681 A1   14    0.00000
145   14 LEU  O    -32.31049 -14.71998   98.40126 A1   14    0.00000
146   15 ASN  N    -30.73908 -15.58168   97.02166 A1   15    0.00000
147   15 ASN  H    -30.47955 -16.38705   96.48149 A1   15    0.00000
148   15 ASN  CA   -29.88530 -14.39297   97.02352 A1   15    0.00000
149   15 ASN  CB   -28.47094 -14.93729   97.29287 A1   15    0.00000
150   15 ASN  CG   -27.86774 -14.18957   98.46652 A1   15    0.00000
151   15 ASN  OD1  -28.47231 -13.98878   99.50693 A1   15    0.00000
152   15 ASN  ND2  -26.63329 -13.74712   98.26721 A1   15    0.00000
153   15 ASN  HD21 -26.12722 -13.93409   97.42633 A1   15    0.00000
154   15 ASN  HD22 -26.21377 -13.18778   98.98020 A1   15    0.00000
155   15 ASN  C    -30.09328 -13.70870   95.65633 A1   15    0.00000
156   15 ASN  O    -30.96066 -14.17939   94.92357 A1   15    0.00000
157   16 PRO  N    -29.35358 -12.64312   95.25454 A1   16    0.00000
158   16 PRO  CD   -29.47390 -12.14147   93.88390 A1   16    0.00000
159   16 PRO  CA   -28.34388 -11.89943   96.02164 A1   16    0.00000
160   16 PRO  CB   -27.47317 -11.32145   94.90180 A1   16    0.00000
161   16 PRO  CG   -28.40713 -11.06430   93.72211 A1   16    0.00000
162   16 PRO  C    -28.67201 -10.84560   96.98393 A1   16    0.00000
163   16 PRO  O    -28.49727 -10.81095   98.14625 A1   16    0.00000
164   17 ASP  N    -29.73099  -9.96981   96.45979 A1   17    0.00000
165   17 ASP  H    -30.06531 -10.06794   95.52595 A1   17    0.00000
166   17 ASP  CA   -30.07647  -8.75629   97.18869 A1   17    0.00000
167   17 ASP  CB   -30.80318  -7.83976   96.20071 A1   17    0.00000
168   17 ASP  CG   -30.22601  -6.44601   96.27578 A1   17    0.00000
169   17 ASP  OD1  -29.42577  -6.10216   95.40955 A1   17    0.00000
170   17 ASP  OD2  -30.58500  -5.71147   97.19272 A1   17    0.00000
171   17 ASP  C    -30.91226  -8.96778   98.44177 A1   17    0.00000
172   17 ASP  O    -30.52677  -8.65960   99.56331 A1   17    0.00000
173   18 GLN  N    -32.11780  -9.49744   98.20428 A1   18    0.00000
174   18 GLN  H    -32.36542  -9.81984   97.29256 A1   18    0.00000
175   18 GLN  CA   -33.10696  -9.57864   99.27949 A1   18    0.00000
176   18 GLN  CB   -34.05728  -8.37464   99.14180 A1   18    0.00000
177   18 GLN  CG   -33.36307  -7.07517   99.58476 A1   18    0.00000
178   18 GLN  CD   -33.97880  -5.85158   98.94046 A1   18    0.00000
179   18 GLN  OE1  -35.13776  -5.50918   99.12725 A1   18    0.00000
180   18 GLN  NE2  -33.14378  -5.16835   98.16624 A1   18    0.00000
181   18 GLN  HE21 -32.19859  -5.47544   97.99847 A1   18    0.00000
182   18 GLN  HE22 -33.43475  -4.32502   97.72302 A1   18    0.00000
183   18 GLN  C    -33.83924 -10.91558   99.26964 A1   18    0.00000
184   18 GLN  O    -33.74750 -11.68763   98.32391 A1   18    0.00000
185   19 SER  N    -34.51482 -11.16924  100.39831 A1   19    0.00000
186   19 SER  H    -34.63228 -10.43017  101.06649 A1   19    0.00000
187   19 SER  CA   -34.94474 -12.50816  100.83625 A1   19    0.00000
188   19 SER  CB   -35.43672 -12.36114  102.28173 A1   19    0.00000
```

FIG. 4

```
./DFL_MIN2.CRD        Thu Feb 25 14:58:48 1993        4

189    19 SER   OG   -34.37   1 -11.87727 103.10841 A1   19   0.00000
190    19 SER   HG   -33.85..4  -12.63499 103.40254 A1   19   0.00000
191    19 SER   C    -35.97640 -13.29776 100.02197 A1   19   0.00000
192    19 SER   O    -36.49518 -12.86400  99.00144 A1   19   0.00000
193    20 GLY   N    -36.24917 -14.51787 100.53004 A1   20   0.00000
194    20 GLY   H    -35.87834 -14.79673 101.41380 A1   20   0.00000
195    20 GLY   CA   -37.08223 -15.47533  99.79192 A1   20   0.00000
196    20 GLY   C    -38.39897 -15.89747 100.44590 A1   20   0.00000
197    20 GLY   O    -39.10838 -15.10421 101.05171 A1   20   0.00000
198    21 GLU   N    -38.72023 -17.18722 100.25477 A1   21   0.00000
199    21 GLU   H    -38.03254 -17.84573  99.94375 A1   21   0.00000
200    21 GLU   CA   -40.11538 -17.64629 100.27114 A1   21   0.00000
201    21 GLU   CB   -40.54163 -17.64420  98.79559 A1   21   0.00000
202    21 GLU   CG   -42.00974 -17.90322  98.44054 A1   21   0.00000
203    21 GLU   CD   -42.16555 -17.98331  96.93169 A1   21   0.00000
204    21 GLU   OE1  -43.22010 -17.59671  96.43390 A1   21   0.00000
205    21 GLU   OE2  -41.23758 -18.43207  96.25678 A1   21   0.00000
206    21 GLU   C    -40.28326 -19.04137 100.89226 A1   21   0.00000
207    21 GLU   O    -39.32286 -19.78361 101.07437 A1   21   0.00000
208    22 PHE   N    -41.54286 -19.38051 101.22645 A1   22   0.00000
209    22 PHE   H    -42.30204 -18.76344 101.01655 A1   22   0.00000
210    22 PHE   CA   -41.84777 -20.63223 101.93252 A1   22   0.00000
211    22 PHE   CB   -41.76716 -20.31207 103.43794 A1   22   0.00000
212    22 PHE   CG   -41.45246 -21.48591 104.34752 A1   22   0.00000
213    22 PHE   CD1  -40.59481 -21.25886 105.44935 A1   22   0.00000
214    22 PHE   CD2  -42.01384 -22.76966 104.14562 A1   22   0.00000
215    22 PHE   CE1  -40.30109 -22.30643 106.36948 A1   22   0.00000
216    22 PHE   CE2  -41.72224 -23.81970 105.04232 A1   22   0.00000
217    22 PHE   CZ   -40.86722 -23.58408 106.14281 A1   22   0.00000
218    22 PHE   C    -43.25845 -21.11988 101.58028 A1   22   0.00000
219    22 PHE   O    -44.19436 -20.32985 101.55111 A1   22   0.00000
220    23 MET   N    -43.39639 -22.43138 101.32298 A1   23   0.00000
221    23 MET   H    -42.59132 -23.03279 101.30500 A1   23   0.00000
222    23 MET   CA   -44.70480 -23.04357 101.02967 A1   23   0.00000
223    23 MET   CB   -45.08326 -22.73266  99.57140 A1   23   0.00000
224    23 MET   CG   -46.39952 -23.35273  99.09264 A1   23   0.00000
225    23 MET   SD   -46.67153 -23.10231  97.33272 A1   23   0.00000
226    23 MET   CE   -47.47592 -24.67640  96.98955 A1   23   0.00000
227    23 MET   C    -44.60710 -24.56281 101.21411 A1   23   0.00000
228    23 MET   O    -43.70841 -25.13566 100.62115 A1   23   0.00000
229    24 PHE   N    -45.43241 -25.30285 101.99622 A1   24   0.00000
230    24 PHE   H    -45.17063 -26.26850 102.03772 A1   24   0.00000
231    24 PHE   CA   -46.72021 -25.11140 102.69060 A1   24   0.00000
232    24 PHE   CB   -47.06193 -23.70552 103.21139 A1   24   0.00000
233    24 PHE   CG   -46.27878 -23.27691 104.43188 A1   24   0.00000
234    24 PHE   CD1  -46.28203 -24.06677 105.60532 A1   24   0.00000
235    24 PHE   CD2  -45.58233 -22.04683 104.40480 A1   24   0.00000
236    24 PHE   CE1  -45.58915 -23.62279 106.75356 A1   24   0.00000
237    24 PHE   CE2  -46.89083 -21.60180 105.55271 A1   24   0.00000
238    24 PHE   CZ   -45.89594 -22.39162 106.72434 A1   24   0.00000
239    24 PHE   C    -47.88569 -25.61775 101.85776 A1   24   0.00000
240    24 PHE   O    -48.73152 -24.87778 101.36424 A1   24   0.00000
241    25 ASP   N    -47.89055 -26.94593 101.74049 A1   25   0.00000
242    25 ASP   H    -47.22437 -27.52403 102.20704 A1   25   0.00000
243    25 ASP   CA   -48.86501 -27.64762 100.90165 A1   25   0.00000
244    25 ASP   CB   -48.21052 -27.81535  99.52046 A1   25   0.00000
245    25 ASP   CG   -49.19634 -28.30012  98.47932 A1   25   0.00000
246    25 ASP   OD1  -49.75750 -27.46672  97.77589 A1   25   0.00000
247    25 ASP   OD2  -49.39656 -29.50745  98.36197 A1   25   0.00000
248    25 ASP   C    -49.38430 -28.98699 101.56183 A1   25   0.00000
249    25 ASP   O    -48.57317 -29.35714 102.56241 A1   25   0.00000
250    26 PHE   N    -50.15819 -29.70261 101.00377 A1   26   0.00000
251    26 PHE   H    -50.60059 -29.39662 100.15349 A1   26   0.00000
252    26 PHE   CA   -50.56037 -30.99701 101.54898 A1   26   0.00000
```

FIG. 5

```
./DEL_MIN2.CRD       Thu Feb 25 14:58:48 1993         5

253  26 PHE  CB   -51. 78 -30.83090 102.82009 A1   26   0.00000
254  26 PHE  CG   -52.80356 -29.92038 102.57724 A1   26   0.00000
255  26 PHE  CD1  -52.50398 -28.55674 102.91777 A1   26   0.00000
256  26 PHE  CD2  -53.70380 -30.42265 101.99011 A1   26   0.00000
257  26 PHE  CE1  -53.58477 -30.68701 102.66706 A1   26   0.00000
258  26 PHE  CE2  -54.86474 -29.55076 101.74257 A1   26   0.00000
259  26 PHE  CZ   -54.76149 -28.18547 102.07912 A1   26   0.00000
260  26 PHE  C    -51.29340 -31.82500 100.51070 A1   26   0.00000
261  26 PHE  O    -51.63257 -31.38211  99.42184 A1   26   0.00000
262  27 ASP  N    -51.50640 -33.00225 100.89199 A1   27   0.00000
263  27 ASP  H    -51.30608 -33.34660 101.83544 A1   27   0.00000
264  27 ASP  CA   -52.05815 -34.11623 100.01741 A1   27   0.00000
265  27 ASP  CB   -53.56271 -34.25359 100.24733 A1   27   0.00000
266  27 ASP  CG   -53.82295 -35.66101 100.73899 A1   27   0.00000
267  27 ASP  OD1  -52.95640 -36.23164 101.40272 A1   27   0.00000
268  27 ASP  OD2  -54.89062 -36.19966 100.47314 A1   27   0.00000
269  27 ASP  C    -51.70102 -34.05698  98.54820 A1   27   0.00000
270  27 ASP  O    -52.51335 -34.10386  97.63254 A1   27   0.00000
271  28 GLY  N    -50.39045 -33.92246  98.35075 A1   28   0.00000
272  28 GLY  H    -49.78144 -33.80079  99.13160 A1   28   0.00000
273  28 GLY  CA   -49.88845 -33.86633  96.98221 A1   28   0.00000
274  28 GLY  C    -50.00090 -32.51821  96.28701 A1   28   0.00000
275  28 GLY  O    -49.04304 -32.03342  95.69731 A1   28   0.00000
276  29 ASP  N    -51.21573 -31.96145  96.33541 A1   29   0.00000
277  29 ASP  H    -51.53955 -32.39453  96.87595 A1   29   0.00000
278  29 ASP  CA   -51.52130 -30.85124  95.43198 A1   29   0.00000
279  29 ASP  CB   -52.38232 -31.44665  94.30287 A1   29   0.00000
280  29 ASP  CG   -52.46245 -30.54960  93.07581 A1   29   0.00000
281  29 ASP  OD1  -51.63429 -30.32445  92.44162 A1   29   0.00000
282  29 ASP  OD2  -53.56233 -30.10545  92.75048 A1   29   0.00000
283  29 ASP  C    -52.21461 -29.64631  96.07233 A1   29   0.00000
284  29 ASP  O    -52.39419 -28.59407  95.46732 A1   29   0.00000
285  30 GLU  N    -52.65130 -29.81701  97.32405 A1   30   0.00000
286  30 GLU  H    -52.34793 -30.57647  97.90251 A1   30   0.00000
287  30 GLU  CA   -53.43516 -28.70871  97.86160 A1   30   0.00000
288  30 GLU  CB   -54.71008 -29.18152  98.54724 A1   30   0.00000
289  30 GLU  CG   -55.04100 -29.71506  97.67444 A1   30   0.00000
290  30 GLU  CD   -57.13279 -29.50058  98.43828 A1   30   0.00000
291  30 GLU  OE1  -57.79466 -30.47326  98.78969 A1   30   0.00000
292  30 GLU  OE2  -57.48539 -28.34297  98.66447 A1   30   0.00000
293  30 GLU  C    -52.69655 -27.80995  98.82987 A1   30   0.00000
294  30 GLU  O    -52.13191 -28.20198  99.84476 A1   30   0.00000
295  31 ILE  N    -52.76110 -26.53268  98.46810 A1   31   0.00000
296  31 ILE  H    -53.28532 -26.29454  97.65353 A1   31   0.00000
297  31 ILE  CA   -51.98442 -25.52536  99.18511 A1   31   0.00000
298  31 ILE  CB   -51.81933 -24.32331  98.23317 A1   31   0.00000
299  31 ILE  CG2  -53.16329 -23.65625  97.91607 A1   31   0.00000
300  31 ILE  CG1  -50.75168 -23.33810  98.71478 A1   31   0.00000
301  31 ILE  CD   -50.41981 -22.27940  97.66271 A1   31   0.00000
302  31 ILE  C    -52.51316 -25.12446 100.56211 A1   31   0.00000
303  31 ILE  O    -53.70233 -24.97567 100.82175 A1   31   0.00000
304  32 PHE  N    -51.54696 -24.95576 101.46562 A1   32   0.00000
305  32 PHE  H    -50.59061 -25.06998 101.18020 A1   32   0.00000
306  32 PHE  CA   -51.85606 -24.57978 102.84494 A1   32   0.00000
307  32 PHE  CB   -50.76201 -25.18703 103.73391 A1   32   0.00000
308  32 PHE  CG   -51.19588 -26.22218 104.74893 A1   32   0.00000
309  32 PHE  CD1  -50.23927 -27.18148 105.15120 A1   32   0.00000
310  32 PHE  CD2  -52.49149 -26.22907 105.32211 A1   32   0.00000
311  32 PHE  CE1  -50.57386 -28.14516 106.12524 A1   32   0.00000
312  32 PHE  CE2  -52.82688 -27.19600 106.29575 A1   32   0.00000
313  32 PHE  CZ   -51.86606 -28.15152 106.69566 A1   32   0.00000
314  32 PHE  C    -51.84397 -23.07181 103.07985 A1   32   0.00000
315  32 PHE  O    -52.76581 -22.46086 103.62205 A1   32   0.00000
316  33 HIS  N    -50.69099 -22.11451 102.70013 A1   33   0.00000
```

FIG. 6

```
/DR: MIN2.CRD        Thu Feb 25 14:58:48 1993       6

317   33 HIS  N     -50.06   -22.98834 102.10706 A1   33   0.00000
318   33 HIS  CA    -50.22   -21.21727 103.23242 A1   33   0.00000
319   33 HIS  CB    -49.65908 -21.51540 104.63303 A1   33   0.00000
320   33 HIS  CG    -49.22984 -20.32142 105.45366 A1   33   0.00000
321   33 HIS  ND1   -48.02826 -19.72793 105.37205 A1   33   0.00000
322   33 HIS  HD1   -47.28999 -19.92757 104.75923 A1   33   0.00000
323   33 HIS  CD2   -49.97214 -19.68828 106.45019 A1   33   0.00000
324   33 HIS  NE2   -49.20118 -18.70682 106.97086 A1   33   0.00000
325   33 HIS  CE1   -48.00110 -18.72654 106.30763 A1   33   0.00000
326   33 HIS  C     -49.11511 -20.78472 102.29629 A1   33   0.00000
327   33 HIS  O     -48.59725 -21.61206 101.55845 A1   33   0.00000
328   34 VAL  N     -48.74537 -19.50449 102.33695 A1   34   0.00000
329   34 VAL  H     -49.19429 -18.80802 102.90183 A1   34   0.00000
330   34 VAL  CA    -47.51776 -19.11490 101.64269 A1   34   0.00000
331   34 VAL  CB    -47.81303 -18.42567 100.28392 A1   34   0.00000
332   34 VAL  CG1   -46.56686 -18.41158  99.39158 A1   34   0.00000
333   34 VAL  CG2   -48.95871 -19.06363  99.49006 A1   34   0.00000
334   34 VAL  C     -46.79652 -18.14692 102.56509 A1   34   0.00000
335   34 VAL  O     -47.41849 -17.54298 103.42874 A1   34   0.00000
336   35 ASP  N     -45.47963 -18.03426 102.37666 A1   35   0.00000
337   35 ASP  H     -45.03039 -18.68906 101.76710 A1   35   0.00000
338   35 ASP  CA    -44.68799 -16.93300 102.93355 A1   35   0.00000
339   35 ASP  CB    -44.74876 -15.73492 101.94639 A1   35   0.00000
340   35 ASP  CG    -46.11850 -15.06364 101.88569 A1   35   0.00000
341   35 ASP  OD1   -46.85196 -15.31279 100.93528 A1   35   0.00000
342   35 ASP  OD2   -46.43780 -14.28565 102.76747 A1   35   0.00000
343   35 ASP  C     -44.90949 -16.57120 104.41152 A1   35   0.00000
344   35 ASP  O     -45.03304 -17.43137 105.27733 A1   35   0.00000
345   36 MET  N     -44.91212 -15.26386 104.68945 A1   36   0.00000
346   36 MET  H     -44.97503 -14.58792 103.95356 A1   36   0.00000
347   36 MET  CA    -45.05621 -14.74244 106.04065 A1   36   0.00000
348   36 MET  CB    -44.58443 -13.28473 106.01845 A1   36   0.00000
349   36 MET  CG    -43.15122 -13.10955 105.50403 A1   36   0.00000
350   36 MET  SD    -42.96722 -11.71848 104.37016 A1   36   0.00000
351   36 MET  CE    -43.60204 -10.40582 105.42531 A1   36   0.00000
352   36 MET  C     -46.49207 -14.77022 106.53712 A1   36   0.00000
353   36 MET  O     -46.75425 -14.73983 107.73458 A1   36   0.00000
354   37 ALA  N     -47.43476 -14.78996 105.58618 A1   37   0.00000
355   37 ALA  H     -47.21869 -14.87225 104.60519 A1   37   0.00000
356   37 ALA  CA    -48.80100 -14.57493 106.05297 A1   37   0.00000
357   37 ALA  CB    -49.30059 -13.19637 105.61316 A1   37   0.00000
358   37 ALA  C     -49.83252 -15.61256 105.65673 A1   37   0.00000
359   37 ALA  O     -49.85254 -16.18787 104.57639 A1   37   0.00000
360   38 LYS  N     -50.76933 -15.79391 106.59397 A1   38   0.00000
361   38 LYS  H     -50.65212 -15.37866 107.49351 A1   38   0.00000
362   38 LYS  CA    -52.00981 -16.48765 106.23832 A1   38   0.00000
363   38 LYS  CB    -52.90628 -16.55867 107.48308 A1   38   0.00000
364   38 LYS  CG    -52.41585 -17.40517 108.60236 A1   38   0.00000
365   38 LYS  CD    -53.40991 -18.62084 108.86903 A1   38   0.00000
366   38 LYS  CE    -53.42547 -19.66155 107.75111 A1   38   0.00000
367   38 LYS  NZ    -54.76503 -20.17861 107.56038 A1   38   0.00000
368   38 LYS  HZ1   -54.79226 -20.92377 106.83759 A1   38   0.00000
369   38 LYS  HZ2   -55.17879 -20.59510 108.44046 A1   38   0.00000
370   38 LYS  HZ3   -55.42747 -19.41621 107.27224 A1   38   0.00000
371   38 LYS  C     -52.74081 -15.73437 105.12989 A1   38   0.00000
372   38 LYS  O     -52.72521 -14.51209 105.10297 A1   38   0.00000
373   39 LYS  N     -53.35457 -16.44351 104.17702 A1   39   0.00000
374   39 LYS  H     -53.59774 -15.96113 103.33578 A1   39   0.00000
375   39 LYS  CA    -53.67982 -17.86931 104.22041 A1   39   0.00000
376   39 LYS  CB    -55.18971 -18.00505 104.55346 A1   39   0.00000
377   39 LYS  CG    -56.24681 -17.64030 103.42417 A1   39   0.00000
378   39 LYS  CD    -56.27039 -16.52550 102.62130 A1   39   0.00000
379   39 LYS  CE    -56.64532 -16.69561 101.13213 A1   39   0.00000
380   39 LYS  NZ    -55.66337 -17.54692 100.43802 A1   39   0.00000
```

FIG. 7

```
./CA1_XH2.CRD        Thu Feb 25 14:58:48 1993         7

381   39 LYS  HZ1   -55.( 45 -18.54581 100.36313 A1   39   0.00000
382   39 LYS  HZ2   -55.   53 -17.26725  99.46103 A1   39   0.00000
383   39 LYS  HZ3   -54.72486 -17.51921 100.90690 A1   39   0.00000
384   39 LYS  C     -53.44423 -18.44283 102.84433 A1   39   0.00000
385   39 LYS  O     -53.43351 -17.67518 101.88936 A1   39   0.00000
386   40 GLU  N     -53.41332 -19.77420 102.71885 A1   40   0.00000
387   40 GLU  H     -53.16154 -20.43691 103.42697 A1   40   0.00000
388   40 GLU  CA    -54.08892 -20.14645 101.48663 A1   40   0.00000
389   40 GLU  CB    -53.22132 -20.84643 100.44056 A1   40   0.00000
390   40 GLU  CG    -52.68203 -19.82757  99.41114 A1   40   0.00000
391   40 GLU  CD    -53.78227 -18.90107  98.89631 A1   40   0.00000
392   40 GLU  OE1   -53.60681 -17.68372  98.89245 A1   40   0.00000
393   40 GLU  OE2   -54.88246 -19.35560  98.59153 A1   40   0.00000
394   40 GLU  C     -55.46625 -20.74566 101.61501 A1   40   0.00000
395   40 GLU  O     -56.42031 -20.18304 101.08479 A1   40   0.00000
396   41 THR  N     -55.56321 -21.84976 102.35754 A1   41   0.00000
397   41 THR  H     -54.77319 -22.20472 102.86321 A1   41   0.00000
398   41 THR  CA    -56.84476 -22.55464 102.30963 A1   41   0.00000
399   41 THR  CB    -56.55011 -24.05830 102.16109 A1   41   0.00000
400   41 THR  OG1   -57.73042 -24.75407 101.74066 A1   41   0.00000
401   41 THR  HG1   -57.47835 -25.59614 101.33840 A1   41   0.00000
402   41 THR  CG2   -55.95304 -24.67173 103.43152 A1   41   0.00000
403   41 THR  C     -57.85722 -22.26510 103.42344 A1   41   0.00000
404   41 THR  O     -57.54677 -21.93546 104.56718 A1   41   0.00000
405   42 VAL  N     -59.12316 -22.41525 103.00455 A1   42   0.00000
406   42 VAL  H     -59.25687 -22.81422 102.09633 A1   42   0.00000
407   42 VAL  CA    -60.29134 -22.03291 103.80812 A1   42   0.00000
408   42 VAL  CB    -61.57611 -22.26646 102.98525 A1   42   0.00000
409   42 VAL  CG1   -62.83989 -21.83994 103.74041 A1   42   0.00000
410   42 VAL  CG2   -61.49852 -21.55078 101.63610 A1   42   0.00000
411   42 VAL  C     -60.39368 -22.75550 105.14170 A1   42   0.00000
412   42 VAL  O     -60.54018 -22.16641 106.20404 A1   42   0.00000
413   43 TRP  N     -60.26652 -24.07997 105.07466 A1   43   0.00000
414   43 TRP  H     -60.09540 -24.53437 104.20145 A1   43   0.00000
415   43 TRP  CA    -60.35178 -24.82113 106.34002 A1   43   0.00000
416   43 TRP  CB    -60.91225 -26.25321 106.17013 A1   43   0.00000
417   43 TRP  CG    -60.96314 -26.72606 104.73262 A1   43   0.00000
418   43 TRP  CD2   -59.88712 -27.12198 103.92127 A1   43   0.00000
419   43 TRP  CE2   -60.47947 -27.49629 102.60102 A1   43   0.00000
420   43 TRP  CE3   -58.50029 -27.24274 104.12574 A1   43   0.00000
421   43 TRP  CD1   -62.11826 -26.86040 103.93459 A1   43   0.00000
422   43 TRP  NE1   -61.84174 -27.31306 102.67766 A1   43   0.00000
423   43 TRP  HE1   -62.50030 -27.49046 101.97106 A1   43   0.00000
424   43 TRP  CZ2   -59.62565 -27.96652 101.58525 A1   43   0.00000
425   43 TRP  CZ3   -57.69263 -27.72260 103.07694 A1   43   0.00000
426   43 TRP  CH2   -58.24204 -28.07937 101.82597 A1   43   0.00000
427   43 TRP  C     -59.07150 -24.84373 107.16564 A1   43   0.00000
428   43 TRP  O     -58.85050 -25.68073 108.02836 A1   43   0.00000
429   44 ARG  N     -58.22471 -23.84563 106.89519 A1   44   0.00000
430   44 ARG  H     -58.31398 -23.27977 107.07364 A1   44   0.00000
431   44 ARG  CA    -57.22046 -23.49560 107.89144 A1   44   0.00000
432   44 ARG  CB    -55.83244 -23.09727 107.26013 A1   44   0.00000
433   44 ARG  CG    -54.63741 -23.63473 108.22026 A1   44   0.00000
434   44 ARG  CD    -53.30915 -23.64273 107.47006 A1   44   0.00000
435   44 ARG  NE    -52.10625 -23.26000 108.32672 A1   44   0.00000
436   44 ARG  HE    -52.36221 -22.91543 109.25139 A1   44   0.00000
437   44 ARG  CZ    -50.93149 -23.33650 107.86475 A1   44   0.00000
438   44 ARG  NH1   -49.92358 -22.86519 108.56844 A1   44   0.00000
439   44 ARG  HH11  -48.98076 -22.84912 108.24673 A1   44   0.00000
440   44 ARG  HH12  -50.05162 -22.52238 109.51721 A1   44   0.00000
441   44 ARG  NH2   -50.67215 -23.59024 106.69352 A1   44   0.00000
442   44 ARG  HH21  -49.73591 -23.96008 106.35339 A1   44   0.00000
443   44 ARG  HH22  -51.41769 -24.25918 106.14195 A1   44   0.00000
444   44 ARG  C     -57.42751 -22.55857 108.38029 A1   44   0.00000
```

FIG. 8

```
./DRI_KIN2.CRD        Thu Feb 25 14:58:48 1993

445    44 ARG  O    -56.5    4 -21.39201 108.88943 A1    44    0.00000
   446    45 LEU  N    -58.65410 -21.55686 108.18548 A1    45    0.00000
   447    45 LEU  H    -59.36846 -22.06382 107.69729 A1    45    0.00000
   448    45 LEU  CA   -58.94679 -20.21897 108.70611 A1    45    0.00000
   449    45 LEU  CB   -59.87267 -19.46515 107.74942 A1    45    0.00000
   450    45 LEU  CG   -59.15056 -18.96990 106.49579 A1    45    0.00000
   451    45 LEU  CD1  -60.14534 -18.41906 105.47407 A1    45    0.00000
   452    45 LEU  CD2  -58.10431 -17.92289 106.87944 A1    45    0.00000
   453    45 LEU  C    -59.55818 -20.20104 110.09168 A1    45    0.00000
   454    45 LEU  O    -59.53362 -19.19926 110.79199 A1    45    0.00000
   455    46 GLU  N    -60.08917 -21.36024 110.48954 A1    46    0.00000
   456    46 GLU  H    -60.14047 -22.14708 109.87631 A1    46    0.00000
   457    46 GLU  CA   -60.58379 -21.47317 111.86481 A1    46    0.00000
   458    46 GLU  CB   -61.47817 -22.71518 111.95437 A1    46    0.00000
   459    46 GLU  CG   -60.80881 -24.02305 111.51772 A1    46    0.00000
   460    46 GLU  CD   -61.85264 -25.11830 111.46594 A1    46    0.00000
   461    46 GLU  OE1  -62.26867 -25.47222 110.36424 A1    46    0.00000
   462    46 GLU  OE2  -62.24894 -25.60616 112.52280 A1    46    0.00000
   463    46 GLU  C    -59.48698 -21.49323 112.92683 A1    46    0.00000
   464    46 GLU  O    -59.60959 -21.22226 114.10493 A1    46    0.00000
   465    47 GLU  N    -58.27880 -21.79310 112.44220 A1    47    0.00000
   466    47 GLU  H    -58.18142 -22.06659 111.48920 A1    47    0.00000
   467    47 GLU  CA   -57.08155 -21.73864 113.27698 A1    47    0.00000
   468    47 GLU  CB   -55.89121 -22.09481 112.39059 A1    47    0.00000
   469    47 GLU  CG   -55.95036 -23.50661 111.78977 A1    47    0.00000
   470    47 GLU  CD   -55.55418 -24.59648 112.78701 A1    47    0.00000
   471    47 GLU  OE1  -55.48886 -25.74409 112.37878 A1    47    0.00000
   472    47 GLU  OE2  -55.29749 -24.27876 113.95212 A1    47    0.00000
   473    47 GLU  C    -56.83827 -20.38151 113.91510 A1    47    0.00000
   474    47 GLU  O    -56.67000 -19.35742 113.26194 A1    47    0.00000
   475    48 PHE  N    -56.83807 -20.40716 115.24713 A1    48    0.00000
   476    48 PHE  H    -56.92233 -21.28123 115.72305 A1    48    0.00000
   477    48 PHE  CA   -56.75617 -19.13647 115.96362 A1    48    0.00000
   478    48 PHE  CB   -57.20231 -19.34982 117.41420 A1    48    0.00000
   479    48 PHE  CG   -58.41657 -18.49841 117.70829 A1    48    0.00000
   480    48 PHE  CD1  -59.71122 -19.00320 117.44215 A1    48    0.00000
   481    48 PHE  CD2  -58.25459 -17.19966 118.24455 A1    48    0.00000
   482    48 PHE  CE1  -60.04630 -18.20670 117.71246 A1    48    0.00000
   483    48 PHE  CE2  -59.38540 -16.40286 118.51469 A1    48    0.00000
   484    48 PHE  CZ   -60.66202 -16.90878 118.24779 A1    48    0.00000
   485    48 PHE  C    -55.39240 -18.46628 115.93777 A1    48    0.00000
   486    48 PHE  O    -54.35117 -19.07618 115.72587 A1    48    0.00000
   487    49 GLY  N    -55.43214 -17.15361 116.19761 A1    49    0.00000
   488    49 GLY  H    -56.32069 -16.72101 116.34575 A1    49    0.00000
   489    49 GLY  CA   -54.23420 -16.30520 116.13162 A1    49    0.00000
   490    49 GLY  C    -52.92695 -16.86464 116.68056 A1    49    0.00000
   491    49 GLY  O    -51.85815 -16.69886 116.10714 A1    49    0.00000
   492    50 ARG  N    -53.03915 -17.56211 117.81779 A1    50    0.00000
   493    50 ARG  H    -53.93666 -17.67284 118.24069 A1    50    0.00000
   494    50 ARG  CA   -51.84656 -18.16800 118.42224 A1    50    0.00000
   495    50 ARG  CB   -52.27437 -18.92760 119.68340 A1    50    0.00000
   496    50 ARG  CG   -51.10260 -19.32736 120.58254 A1    50    0.00000
   497    50 ARG  CD   -51.53002 -20.14774 121.80047 A1    50    0.00000
   498    50 ARG  NE   -50.37432 -20.44943 122.64580 A1    50    0.00000
   499    50 ARG  HE   -49.69865 -19.71957 122.75767 A1    50    0.00000
   500    50 ARG  CZ   -50.24449 -21.63184 123.26571 A1    50    0.00000
   501    50 ARG  NH1  -49.18578 -21.04466 124.04503 A1    50    0.00000
   502    50 ARG  HH11 -49.05579 -22.71179 124.52612 A1    50    0.00000
   503    50 ARG  HH12 -48.49360 -21.13233 124.16453 A1    50    0.00000
   504    50 ARG  NH2  -51.15926 -22.58829 123.10823 A1    50    0.00000
   505    50 ARG  HH21 -51.08073 -23.47414 123.56513 A1    50    0.00000
   506    50 ARG  HH22 -51.95092 -22.42795 122.51852 A1    50    0.00000
   507    50 ARG  C    -51.06703 -19.09561 117.49074 A1    50    0.00000
   508    50 ARG  O    -49.84240 -19.05133 117.41526 A1    50    0.00000
```

FIG. 9

```
/DRJ_KD2.CRD       Thu Feb 25 14:58:48 1993       9

509   51 PHE  N     -51.84     -19.87778  116.73839  A1   51   0.00000
510   51 PHE  H     -52.84564  -19.76657  116.76797  A1   51   0.00000
511   51 PHE  CA    -51.29477  -20.78796  115.73402  A1   51   0.00000
512   51 PHE  CB    -52.51672  -21.52503  115.15449  A1   51   0.00000
513   51 PHE  CG    -52.25099  -22.49194  114.02359  A1   51   0.00000
514   51 PHE  CD1   -51.87888  -23.82851  114.29503  A1   51   0.00000
515   51 PHE  CD2   -52.45788  -22.06484  112.69289  A1   51   0.00000
516   51 PHE  CE1   -51.72483  -24.74621  113.22969  A1   51   0.00000
517   51 PHE  CE2   -52.30778  -22.98082  111.63059  A1   51   0.00000
518   51 PHE  CZ    -51.94314  -24.31860  111.90000  A1   51   0.00000
519   51 PHE  C     -50.50268  -20.00696  114.69371  A1   51   0.00000
520   51 PHE  O     -49.31281  -20.20801  114.47961  A1   51   0.00000
521   52 ALA  N     -51.20469  -19.03212  114.10202  A1   52   0.00000
522   52 ALA  H     -52.16823  -18.89764  114.33870  A1   52   0.00000
523   52 ALA  CA    -50.54896  -18.16486  113.11957  A1   52   0.00000
524   52 ALA  CB    -51.52058  -17.09216  112.62511  A1   52   0.00000
525   52 ALA  C     -49.28257  -17.48933  113.62687  A1   52   0.00000
526   52 ALA  O     -48.27008  -17.39834  112.94510  A1   52   0.00000
527   53 SER  N     -49.35763  -17.04955  114.88764  A1   53   0.00000
528   53 SER  H     -50.22411  -17.11498  115.38567  A1   53   0.00000
529   53 SER  CA    -48.18100  -16.47055  115.53815  A1   53   0.00000
530   53 SER  CB    -48.58146  -16.02158  116.95383  A1   53   0.00000
531   53 SER  OG    -47.59593  -15.15541  117.52845  A1   53   0.00000
532   53 SER  HG    -47.05158  -14.90357  118.42105  A1   53   0.00000
533   53 SER  C     -46.99433  -17.42737  115.57436  A1   53   0.00000
534   53 SER  O     -45.85463  -17.11790  115.12568  A1   53   0.00000
535   54 PHE  N     -47.26082  -18.64220  116.08200  A1   54   0.00000
536   54 PHE  H     -48.18040  -18.87361  116.41568  A1   54   0.00000
537   54 PHE  CA    -46.18727  -19.64350  116.09995  A1   54   0.00000
538   54 PHE  CB    -46.69548  -20.99079  116.63413  A1   54   0.00000
539   54 PHE  CG    -46.90625  -20.99411  118.13255  A1   54   0.00000
540   54 PHE  CD1   -48.11656  -21.50310  118.65539  A1   54   0.00000
541   54 PHE  CD2   -45.89246  -20.53119  119.00621  A1   54   0.00000
542   54 PHE  CE1   -48.31310  -21.55376  120.05266  A1   54   0.00000
543   54 PHE  CE2   -46.08593  -20.57973  120.40382  A1   54   0.00000
544   54 PHE  CZ    -47.30008  -21.09192  120.92307  A1   54   0.00000
545   54 PHE  C     -45.57270  -19.90650  114.73758  A1   54   0.00000
546   54 PHE  O     -44.36030  -19.93109  114.55246  A1   54   0.00000
547   55 GLU  N     -46.46681  -20.08976  113.76558  A1   55   0.00000
548   55 GLU  H     -47.45338  -20.04226  113.95516  A1   55   0.00000
549   55 GLU  CA    -45.97322  -20.41545  112.42886  A1   55   0.00000
550   55 GLU  CB    -47.16512  -20.81915  111.54876  A1   55   0.00000
551   55 GLU  CG    -47.92567  -21.96126  112.19274  A1   55   0.00000
552   55 GLU  CD    -49.04456  -22.36202  111.27677  A1   55   0.00000
553   55 GLU  OE1   -49.15553  -23.53977  110.96047  A1   55   0.00000
554   55 GLU  OE2   -49.80524  -21.50984  110.81474  A1   55   0.00000
555   55 GLU  C     -45.19354  -19.30188  111.76318  A1   55   0.00000
556   55 GLU  O     -44.12678  -19.50387  111.19343  A1   55   0.00000
557   56 ALA  N     -45.73650  -18.08673  111.89532  A1   56   0.00000
558   56 ALA  H     -46.62336  -17.96765  112.34890  A1   56   0.00000
559   56 ALA  CA    -45.00414  -16.92733  111.38640  A1   56   0.00000
560   56 ALA  CB    -45.80074  -15.63071  111.59969  A1   56   0.00000
561   56 ALA  C     -43.63772  -16.77849  112.02791  A1   56   0.00000
562   56 ALA  O     -42.62065  -16.60634  111.36878  A1   56   0.00000
563   57 GLN  N     -43.63088  -16.91454  113.35929  A1   57   0.00000
564   57 GLN  H     -44.46826  -17.03983  113.86832  A1   57   0.00000
565   57 GLN  CA    -42.35063  -16.88200  114.06847  A1   57   0.00000
566   57 GLN  CB    -42.61967  -17.03049  115.56930  A1   57   0.00000
567   57 GLN  CG    -41.40659  -16.75355  116.45895  A1   57   0.00000
568   57 GLN  CD    -41.80070  -16.54589  117.90800  A1   57   0.00000
569   57 GLN  OE1   -42.29879  -16.06206  118.58910  A1   57   0.00000
570   57 GLN  NE2   -41.55425  -10.10011  116.30366  A1   57   0.00000
571   57 GLN  HE21  -41.14709  -18.87176  117.81428  A1   57   0.00000
572   57 GLN  HE22  -41.78115  -15.35728  119.33313  A1   57   0.00000
```

FIG. 10

```
./DR1_MIN2.CRD      Thu Feb 25 14:58:48 1993         10

573   57 GLN   C     -41.13    -17.94055 113.59025 A1   57   0.00000
574   57 GLN   O     -40.18971 -17.68051 113.34773 A2   57   0.00000
575   58 GLY   N     -41.88825 -19.15742 113.41319 A1   58   0.00000
576   58 GLY   H     -42.84771 -19.33514 113.64847 A1   58   0.00000
577   58 GLY   CA    -41.05379 -20.23393 112.87374 A1   58   0.00000
578   58 GLY   C     -40.45534 -19.92701 111.50957 A1   58   0.00000
579   58 GLY   O     -39.25324 -20.01021 111.27849 A1   58   0.00000
580   59 ALA   N     -41.34654 -19.52227 110.60018 A1   59   0.00000
581   59 ALA   H     -42.32072 -19.46762 110.83485 A1   59   0.00000
582   59 ALA   CA    -40.88666 -19.14537 109.26181 A1   59   0.00000
583   59 ALA   CB    -42.07124 -18.74086 108.30101 A1   59   0.00000
584   59 ALA   C     -39.86090 -18.02257 109.26073 A1   59   0.00000
585   59 ALA   O     -38.85187 -18.04905 108.56603 A1   59   0.00000
586   60 LEU   N     -40.12979 -17.02925 110.11113 A1   60   0.00000
587   60 LEU   H     -40.96678 -17.03715 110.66448 A1   60   0.00000
588   60 LEU   CA    -39.17026 -15.93079 110.21454 A1   60   0.00000
589   60 LEU   CB    -39.62974 -14.72108 110.88234 A1   60   0.00000
590   60 LEU   CG    -41.00342 -14.16448 110.06267 A1   60   0.00000
591   60 LEU   CD1   -41.72077 -13.05637 110.83175 A1   60   0.00000
592   60 LEU   CD2   -40.54968 -13.69403 108.67852 A1   60   0.00000
593   60 LEU   C     -37.86300 -16.28607 110.90549 A1   60   0.00000
594   60 LEU   O     -36.81366 -15.71151 110.64266 A1   60   0.00000
595   61 ALA   N     -37.92548 -17.30628 111.76650 A1   61   0.00000
596   61 ALA   H     -38.80416 -17.70206 112.04737 A1   61   0.00000
597   61 ALA   CA    -36.66060 -17.86080 112.25036 A1   61   0.00000
598   61 ALA   CB    -36.90091 -18.87147 113.37402 A1   61   0.00000
599   61 ALA   C     -35.66652 -18.52303 111.13575 A1   61   0.00000
600   61 ALA   O     -34.67753 -18.28483 110.93578 A1   61   0.00000
601   62 ASN   N     -36.59182 -19.33011 110.35468 A1   62   0.00000
602   62 ASN   H     -37.55651 -19.52444 110.56450 A1   62   0.00000
603   62 ASN   CA    -35.93048 -19.97053 109.20954 A1   62   0.00000
604   62 ASN   CB    -36.90608 -20.83397 108.41185 A1   62   0.00000
605   62 ASN   CG    -36.14296 -21.97501 107.76767 A1   62   0.00000
606   62 ASN   OD1   -35.90083 -23.00051 108.38915 A1   62   0.00000
607   62 ASN   ND2   -35.81296 -21.80385 106.49294 A1   62   0.00000
608   62 ASN   HD21  -35.71613 -20.90910 106.04169 A1   62   0.00000
609   62 ASN   HD22  -35.64736 -22.62041 105.92778 A1   62   0.00000
610   62 ASN   C     -35.27272 -18.97317 108.27635 A1   62   0.00000
611   62 ASN   O     -34.08577 -19.05772 107.98073 A1   62   0.00000
612   63 ILE   N     -36.07385 -17.96130 107.91224 A1   63   0.00000
613   63 ILE   H     -37.03805 -17.97906 108.18770 A1   63   0.00000
614   63 ILE   CA    -35.60960 -16.86395 107.05550 A1   63   0.00000
615   63 ILE   CB    -36.79680 -15.88630 106.84927 A1   63   0.00000
616   63 ILE   CG2   -36.71800 -14.58751 107.66300 A1   63   0.00000
617   63 ILE   CG1   -37.00443 -15.60068 105.36486 A1   63   0.00000
618   63 ILE   CD    -38.27181 -14.79756 105.06416 A1   63   0.00000
619   63 ILE   C     -34.32421 -16.14412 107.48562 A1   63   0.00000
620   63 ILE   O     -33.67028 -15.43835 106.72047 A1   63   0.00000
621   64 ALA   N     -33.97867 -16.34078 108.76481 A1   64   0.00000
622   64 ALA   H     -34.55914 -16.88095 109.37800 A1   64   0.00000
623   64 ALA   CA    -32.68252 -15.86370 109.23001 A1   64   0.00000
624   64 ALA   CB    -32.78414 -15.37252 110.67448 A1   64   0.00000
625   64 ALA   C     -31.59324 -16.91956 109.13883 A1   64   0.00000
626   64 ALA   O     -30.45701 -16.65389 108.75412 A1   64   0.00000
627   65 VAL   N     -31.96250 -18.15367 109.50633 A1   65   0.00000
628   65 VAL   H     -32.92093 -18.37577 109.71401 A1   65   0.00000
629   65 VAL   CA    -30.91507 -19.17596 109.47932 A1   65   0.00000
630   65 VAL   CB    -31.28412 -20.41152 110.33210 A1   65   0.00000
631   65 VAL   CG1   -31.53866 -19.97521 111.77524 A1   65   0.00000
632   65 VAL   CG2   -32.45603 -21.23819 109.79675 A1   65   0.00000
633   65 VAL   C     -30.45713 -19.56758 108.06237 A1   65   0.00000
634   65 VAL   O     -29.26568 -19.71596 107.82437 A1   65   0.00000
635   66 ASP   N     -31.42136 -19.66037 107.15805 A1   66   0.00000
636   66 ASP   H     -32.38553 -19.49723 107.38932 A1   66   0.00000
```

FIG. 11

```
./CR1_MIN2.CRD      Thu Feb 25 14:58:48 1993        11

637  66 ASP  CA   -31.0...3 -19.93216 105.76795 A1   66   0.00000
638  66 ASP  CB   -32.31036 -20.24966 104.93007 A1   66   0.00000
639  66 ASP  CG   -33.44297 -19.24219 105.08208 A1   66   0.00000
640  66 ASP  OD1  -33.16986 -18.05114 105.20729 A1   66   0.00000
641  66 ASP  OD2  -34.60286 -19.65468 105.08126 A1   66   0.00000
642  66 ASP  C    -30.18178 -18.83449 105.15564 A1   66   0.00000
643  66 ASP  O    -29.16482 -19.06872 104.50705 A1   66   0.00000
644  67 LYS  N    -30.56424 -17.59916 105.48017 A1   67   0.00000
645  67 LYS  H    -31.49538 -17.48655 105.84055 A1   67   0.00000
646  67 LYS  CA   -29.72959 -16.43204 105.19320 A1   67   0.00000
647  67 LYS  CB   -30.39071 -15.23196 105.87104 A1   67   0.00000
648  67 LYS  CG   -29.79159 -13.86177 105.56853 A1   67   0.00000
649  67 LYS  CD   -30.51506 -12.79056 106.38164 A1   67   0.00000
650  67 LYS  CE   -29.96446 -11.38645 106.14720 A1   67   0.00000
651  67 LYS  NZ   -30.60526 -10.14891 107.01869 A1   67   0.00000
652  67 LYS  HZ1  -30.33262  -9.48398 106.85909 A1   67   0.00000
653  67 LYS  HZ2  -31.70143 -10.49161 106.80064 A1   67   0.00000
654  67 LYS  HZ3  -30.53221 -10.71804 108.01156 A1   67   0.00000
655  67 LYS  C    -28.28117 -16.58093 105.64383 A1   67   0.00000
656  67 LYS  O    -27.33559 -16.44078 104.87661 A1   67   0.00000
657  68 ALA  N    -28.12520 -16.92373 106.92795 A1   68   0.00000
658  68 ALA  H    -28.92119 -17.00935 107.53692 A1   68   0.00000
659  68 ALA  CA   -26.76352 -17.18143 107.40958 A1   68   0.00000
660  68 ALA  CB   -26.77377 -17.44846 108.91534 A1   68   0.00000
661  68 ALA  C    -26.07149 -18.34364 106.70618 A1   68   0.00000
662  68 ALA  O    -24.80989 -18.33297 106.37143 A1   68   0.00000
663  69 ASN  N    -26.87877 -19.37475 106.44973 A1   69   0.00000
664  69 ASN  H    -27.84416 -19.34421 106.72158 A1   69   0.00000
665  69 ASN  CA   -26.32826 -20.54731 105.77098 A1   69   0.00000
666  69 ASN  CB   -27.33794 -21.70567 105.74618 A1   69   0.00000
667  69 ASN  CG   -27.75534 -22.20215 107.12937 A1   69   0.00000
668  69 ASN  OD1  -28.81753 -22.77967 107.30600 A1   69   0.00000
669  69 ASN  ND2  -26.90880 -21.98927 108.13718 A1   69   0.00000
670  69 ASN  HD21 -26.02949 -21.53117 108.03476 A1   69   0.00000
671  69 ASN  HD22 -27.17968 -22.29754 109.04652 A1   69   0.00000
672  69 ASN  C    -25.83413 -20.26827 104.36379 A1   69   0.00000
673  69 ASN  O    -24.88019 -20.87816 103.89106 A1   69   0.00000
674  70 LEU  N    -26.46696 -19.27268 103.71664 A1   70   0.00000
675  70 LEU  H    -27.27121 -18.83110 104.12686 A1   70   0.00000
676  70 LEU  CA   -25.93555 -18.80513 102.42930 A1   70   0.00000
677  70 LEU  CB   -26.70466 -17.57714 101.93156 A1   70   0.00000
678  70 LEU  CG   -28.07464 -17.87907 101.32608 A1   70   0.00000
679  70 LEU  CD1  -28.90878 -16.60756 101.23109 A1   70   0.00000
680  70 LEU  CD2  -27.93286 -18.56192  99.96378 A1   70   0.00000
681  70 LEU  C    -24.47328 -18.42736 102.51389 A1   70   0.00000
682  70 LEU  O    -23.64160 -18.86456 101.72731 A1   70   0.00000
683  71 GLU  N    -24.17065 -17.62592 103.54240 A1   71   0.00000
684  71 GLU  H    -24.87529 -17.33320 104.19342 A1   71   0.00000
685  71 GLU  CA   -22.77384 -17.24207 103.73624 A1   71   0.00000
686  71 GLU  CB   -22.68099 -16.23884 104.88750 A1   71   0.00000
687  71 GLU  CG   -21.33647 -15.50613 104.93364 A1   71   0.00000
688  71 GLU  CD   -21.30052 -14.53829 106.10023 A1   71   0.00000
689  71 GLU  OE1  -20.27115 -14.47665 106.76970 A1   71   0.00000
690  71 GLU  OE2  -22.29376 -13.85012 106.33423 A1   71   0.00000
691  71 GLU  C    -21.86369 -18.43008 103.97868 A1   71   0.00000
692  71 GLU  O    -20.81243 -18.61050 103.36820 A1   71   0.00000
693  72 ILE  N    -22.34609 -19.31836 104.86364 A1   72   0.00000
694  72 ILE  H    -23.21301 -19.12129 105.33200 A1   72   0.00000
695  72 ILE  CA   -21.56703 -20.53142 105.13564 A1   72   0.00000
696  72 ILE  CB   -22.29516 -21.40405 106.17923 A1   72   0.00000
697  72 ILE  CG2  -21.51796 -22.60646 106.50604 A1   72   0.00000
698  72 ILE  CG1  -22.55172 -20.55465 107.45405 A1   72   0.00000
699  72 ILE  CD   -23.34520 -21.36378 108.51280 A1   72   0.00000
700  72 ILE  C    -21.22106 -21.35113 103.89490 A1   72   0.00000
```

FIG. 12

```
./DNA_KD2.crd        Thu Feb 25 14:58:48 1993        12

701   72 ILE   O     -20.79    -21.68162  103.64178 A1   72   0.00000
702   73 MET   N     -22.1..06 -21.67127  103.09738 A1   73   0.00000
703   73 MET   H     -23.17806 -21.34412  103.27303 A1   73   0.00000
704   73 MET   CA    -21.88577 -22.51146  101.95532 A1   73   0.00000
705   73 MET   CB    -23.02917 -23.44601  101.56487 A1   73   0.00000
706   73 MET   CG    -23.30745 -24.44882  102.69030 A1   73   0.00000
707   73 MET   SD    -24.39480 -25.79652  102.19686 A1   73   0.00000
708   73 MET   CE    -24.58745 -26.56731  103.81212 A1   73   0.00000
709   73 MET   C     -21.30840 -21.79430  100.75010 A1   73   0.00000
710   73 MET   O     -20.54740 -22.36938   99.97894 A1   73   0.00000
711   74 THR   N     -21.60342 -20.49214  100.63510 A1   74   0.00000
712   74 THR   H     -22.28955 -20.04403  101.21510 A1   74   0.00000
713   74 THR   CA    -20.82593 -19.73833   99.64704 A1   74   0.00000
714   74 THR   CB    -21.46299 -18.35496   99.36040 A1   74   0.00000
715   74 THR   OG1   -21.01301 -17.84761   98.09669 A1   74   0.00000
716   74 THR   HG1   -20.04699 -17.88381   98.02785 A1   74   0.00000
717   74 THR   CG2   -21.20740 -17.31089  100.44667 A1   74   0.00000
718   74 THR   C     -19.35170 -19.61359  100.02467 A1   74   0.00000
719   74 THR   O     -18.48554 -19.49348   99.16750 A1   74   0.00000
720   75 LYS   N     -19.08538 -19.69260  101.33717 A1   75   0.00000
721   75 LYS   H     -19.81075 -19.65220  102.02321 A1   75   0.00000
722   75 LYS   CA    -17.69833 -19.83955  101.77078 A1   75   0.00000
723   75 LYS   CB    -17.61408 -19.57287  103.27797 A1   75   0.00000
724   75 LYS   CG    -16.20208 -19.66153  103.86107 A1   75   0.00000
725   75 LYS   CD    -16.21051 -19.57437  105.38567 A1   75   0.00000
726   75 LYS   CE    -14.81504 -19.74395  105.98417 A1   75   0.00000
727   75 LYS   NZ    -14.91179 -19.69851  107.44939 A1   75   0.00000
728   75 LYS   HZ1   -13.96820 -19.83508  107.86470 A1   75   0.00000
729   75 LYS   HZ2   -15.29159 -18.77551  107.74094 A1   75   0.00000
730   75 LYS   HZ3   -15.54844 -20.45311  107.77639 A1   75   0.00000
731   75 LYS   C     -17.14118 -21.21770  101.45102 A1   75   0.00000
732   75 LYS   O     -16.11623 -21.36022  100.79660 A1   75   0.00000
733   76 ARG   N     -17.86151 -22.25466  101.90990 A1   76   0.00000
734   76 ARG   H     -18.69512 -22.09296  102.44436 A1   76   0.00000
735   76 ARG   CA    -17.35520 -23.61422  101.67525 A1   76   0.00000
736   76 ARG   CB    -18.33654 -24.60494  102.17145 A1   76   0.00000
737   76 ARG   CG    -18.82789 -24.66219  103.62361 A1   76   0.00000
738   76 ARG   CD    -19.55363 -25.98411  103.91795 A1   76   0.00000
739   76 ARG   NE    -20.36155 -25.99642  105.14334 A1   76   0.00000
740   76 ARG   HE    -21.34527 -25.85364  105.02467 A1   76   0.00000
741   76 ARG   CZ    -19.85069 -26.28686  106.34915 A1   76   0.00000
742   76 ARG   NH1   -20.67426 -26.45770  107.38550 A1   76   0.00000
743   76 ARG   HH11  -20.32038 -26.64144  108.30551 A1   76   0.00000
744   76 ARG   HH12  -21.67206 -26.42100  107.26619 A1   76   0.00000
745   76 ARG   NH2   -18.53304 -26.41209  106.51158 A1   76   0.00000
746   76 ARG   HH21  -18.12377 -26.62371  107.39854 A1   76   0.00000
747   76 ARG   HH22  -17.92942 -26.29542  105.72237 A1   76   0.00000
748   76 ARG   C     -17.06072 -23.91761  100.20901 A1   76   0.00000
749   76 ARG   O     -16.02715 -24.45819   99.83552 A1   76   0.00000
750   77 SER   N     -18.01091 -23.50462   99.36716 A1   77   0.00000
751   77 SER   H     -18.84286 -23.05363   99.69917 A1   77   0.00000
752   77 SER   CA    -17.80506 -23.71642   97.95702 A1   77   0.00000
753   77 SER   CB    -19.13837 -24.15898   97.32351 A1   77   0.00000
754   77 SER   OG    -18.92403 -25.08061   96.24728 A1   77   0.00000
755   77 SER   HG    -18.99574 -24.62840   95.39572 A1   77   0.00000
756   77 SER   C     -17.22854 -22.51234   97.20137 A1   77   0.00000
757   77 SER   O     -17.39865 -22.33993   96.00106 A1   77   0.00000
758   78 ASN   N     -16.52714 -21.66944   97.97646 A1   78   0.00000
759   78 ASN   H     -16.44843 -21.84082   98.96113 A1   78   0.00000
760   78 ASN   CA    -15.74721 -20.53857   97.45264 A1   78   0.00000
761   78 ASN   CB    -14.33390 -21.01377   97.09195 A1   78   0.00000
762   78 ASN   CG    -13.52905 -21.21984   98.36314 A1   78   0.00000
763   78 ASN   OD1   -12.89966 -20.31632   98.85266 A1   78   0.00000
764   78 ASN   ND2   -13.55265 -22.45457   98.85326 A1   78   0.00000
```

FIG. 13

```
./CR1_MD2.CRD      Thu Feb 25 14:56:48 1993        13

765    78 ASN   HD21  -14.C    2  -23.19170  98.43678 A1   78   0.00000
766    78 ASN   HD22  -13.0.../1  -22.65362  99.68493 A1   78   0.00000
767    78 ASN   C     -16.34134  -19.72172  96.31352 A1   78   0.00000
768    78 ASN   O     -15.71478  -19.62979  95.30178 A1   78   0.00000
769    79 TYR   N     -17.59612  -19.32597  96.52354 A1   79   0.00000
770    79 TYR   H     -18.05424  -19.55771  97.38252 A1   79   0.00000
771    79 TYR   CA    -18.21408  -18.48918  95.49858 A1   79   0.00000
772    79 TYR   CB    -19.64874  -18.92649  95.21260 A1   79   0.00000
773    79 TYR   CG    -19.74485  -20.32764  94.65360 A1   79   0.00000
774    79 TYR   CD1   -20.64246  -21.23278  95.25950 A1   79   0.00000
775    79 TYR   CE1   -20.76017  -22.54189  94.75217 A1   79   0.00000
776    79 TYR   CD2   -18.96361  -20.72112  93.54108 A1   79   0.00000
777    79 TYR   CE2   -19.07884  -22.03339  93.03642 A1   79   0.00000
778    79 TYR   CZ    -19.97533  -22.93822  93.64752 A1   79   0.00000
779    79 TYR   OH    -20.07585  -24.23438  93.18578 A1   79   0.00000
780    79 TYR   HH    -19.67682  -24.30670  92.31232 A1   79   0.00000
781    79 TYR   C     -18.21035  -17.01261  95.83719 A1   79   0.00000
782    79 TYR   O     -18.85099  -16.51273  96.76683 A1   79   0.00000
783    80 THR   N     -17.42457  -16.33235  95.00452 A1   80   0.00000
784    80 THR   H     -16.96429  -16.79509  94.24288 A1   80   0.00000
785    80 THR   CA    -17.09577  -14.92660  95.20513 A1   80   0.00000
786    80 THR   CB    -15.89072  -14.87711  96.18098 A1   80   0.00000
787    80 THR   OG1   -15.49849  -13.52440  96.43537 A1   80   0.00000
788    80 THR   HG1   -14.60960  -13.50159  96.80560 A1   80   0.00000
789    80 THR   CG2   -14.69719  -15.72265  95.72104 A1   80   0.00000
790    80 THR   C     -16.77512  -14.32258  93.03840 A1   80   0.00000
791    80 THR   O     -16.16879  -14.97644  92.99811 A1   80   0.00000
792    81 PRO   N     -17.23243  -13.08096  93.61451 A1   81   0.00000
793    81 PRO   CD    -18.04687  -12.25452  94.50529 A1   81   0.00000
794    81 PRO   CA    -16.95963  -12.43774  92.32255 A1   81   0.00000
795    81 PRO   CB    -18.08102  -11.39225  92.28996 A1   81   0.00000
796    81 PRO   CG    -18.22970  -10.94901  93.74456 A1   81   0.00000
797    81 PRO   C     -15.57247  -11.80328  92.25040 A1   81   0.00000
798    81 PRO   O     -15.41926  -10.58936  92.16776 A1   81   0.00000
799    82 ILE   N     -14.65883  -12.66988  92.27154 A1   82   0.00000
800    82 ILE   H     -14.69364  -13.66392  92.31920 A1   82   0.00000
801    82 ILE   CA    -13.18946  -12.18130  92.13921 A1   82   0.00000
802    82 ILE   CB    -12.60010  -11.87598  93.53959 A1   82   0.00000
803    82 ILE   CG2   -12.41140  -13.13773  94.38674 A1   82   0.00000
804    82 ILE   CG1   -11.31152  -11.05228  93.44331 A1   82   0.00000
805    82 ILE   CD    -10.76554  -10.62709  94.80896 A1   82   0.00000
806    82 ILE   C     -12.35649  -13.19907  91.37376 A1   82   0.00000
807    82 ILE   OCT1  -11.36717  -12.81747  90.75062 A1   82   0.00000
808    82 ILE   OCT2  -12.72556  -14.37446  91.38671 A1   82   0.00000
809    83 GLY   N     -17.53322   -0.31236  94.99084 B1    1   0.00000
810    83 GLY   HT1   -17.21994    0.44323  94.35235 B1    1   0.00000
811    83 GLY   HT2   -16.86357   -1.12219  94.96444 B1    1   0.00000
812    83 GLY   HT3   -17.61098    0.01920  95.97150 B1    1   0.00000
813    83 GLY   CA    -18.79853   -0.91116  94.55151 B1    1   0.00000
814    83 GLY   C     -18.52573   -2.38203  94.66351 B1    1   0.00000
815    83 GLY   O     -17.35786   -2.70920  94.84086 B1    1   0.00000
816    84 ASP   N     -19.57260   -3.20239  94.59303 B1    2   0.00000
817    84 ASP   H     -20.49658   -2.89510  94.35600 B1    2   0.00000
818    84 ASP   CA    -19.43900   -4.63200  94.86181 B1    2   0.00000
819    84 ASP   CB    -19.44643   -4.83356  96.38475 B1    2   0.00000
820    84 ASP   CG    -18.89301   -6.19619  96.73815 B1    2   0.00000
821    84 ASP   OD1   -17.69451   -6.29764  96.98109 B1    2   0.00000
822    84 ASP   OD2   -19.66566   -7.14958  96.75715 B1    2   0.00000
823    84 ASP   C     -20.62786   -5.31072  94.19868 B1    2   0.00000
824    84 ASP   O     -21.46903   -4.61697  93.63479 B1    2   0.00000
825    85 THR   N     -20.67796   -6.64606  94.24891 B1    3   0.00000
826    85 THR   H     -20.04362   -7.15926  94.84032 B1    3   0.00000
827    85 THR   CA    -21.75257   -7.39367  93.59154 B1    3   0.00000
828    85 THR   CB    -21.58903   -7.31952  92.05122 B1    3   0.00000
```

FIG. 14

```
./D21_KIN2.CRD        Thu Feb 25 14:58:48 1993        14

828  85 THR  OG1  -22.     .65  -7.82400  91.39964 B1  3   0.00000
830  85 THR  HG1  -22.73431  -7.60152  90.46343 B1  3   0.00000
831  85 THR  CG2  -20.32966  -8.02078  91.53071 B1  3   0.00000
832  85 THR  C    -21.74290  -8.83241  94.09035 B1  3   0.00000
833  85 THR  O    -20.76454  -9.30377  94.65381 B1  3   0.00000
834  86 ARG  N    -22.86491  -9.52779  93.88799 B1  4   0.00000
835  86 ARG  H    -23.62404  -9.13760  93.36423 B1  4   0.00000
836  86 ARG  CA   -22.93360 -10.87552  94.44830 B1  4   0.00000
837  86 ARG  CB   -23.51668 -10.79083  95.86916 B1  4   0.00000
838  86 ARG  CG   -22.74323 -11.65365  96.87092 B1  4   0.00000
839  86 ARG  CD   -23.23116 -13.10294  97.02541 B1  4   0.00000
840  86 ARG  NE   -22.12580 -14.03911  97.27083 B1  4   0.00000
841  86 ARG  HE   -21.93083 -14.68836  96.53494 B1  4   0.00000
842  86 ARG  CZ   -21.37502 -14.05036  98.38612 B1  4   0.00000
843  86 ARG  NH1  -20.31371 -14.85617  98.44757 B1  4   0.00000
844  86 ARG  HH11 -19.73815 -14.87872  99.26299 B1  4   0.00000
845  86 ARG  HH12 -20.05194 -15.47498  97.69021 B1  4   0.00000
846  86 ARG  NH2  -21.67517 -13.26636  99.42563 B1  4   0.00000
847  86 ARG  HH21 -21.13780 -13.26659 100.26897 B1  4   0.00000
848  86 ARG  HH22 -22.46145 -12.65025  99.36831 B1  4   0.00000
849  86 ARG  C    -23.73522 -11.82065  93.57905 B1  4   0.00000
850  86 ARG  O    -24.85200 -11.52883  93.17882 B1  4   0.00000
851  87 PRO  N    -23.12190 -12.98532  93.27325 B1  5   0.00000
852  87 PRO  CD   -21.73269 -13.34562  93.54376 B1  5   0.00000
853  87 PRO  CA   -23.84435 -14.02757  92.53087 B1  5   0.00000
854  87 PRO  CB   -22.78628 -15.13066  92.39999 B1  5   0.00000
855  87 PRO  CG   -21.43460 -14.43376  92.52460 B1  5   0.00000
856  87 PRO  C    -25.10390 -14.54496  93.21975 B1  5   0.00000
857  87 PRO  O    -25.32443 -14.39544  94.41838 B1  5   0.00000
858  88 ARG  N    -25.94344 -15.17061  92.39123 B1  6   0.00000
859  88 ARG  H    -25.68611 -15.35588  91.44433 B1  6   0.00000
860  88 ARG  CA   -27.23219 -15.62675  92.90235 B1  6   0.00000
861  88 ARG  CB   -28.29078 -15.39805  91.81653 B1  6   0.00000
862  88 ARG  CG   -29.70863 -15.55859  92.35844 B1  6   0.00000
863  88 ARG  CD   -30.79150 -14.91787  91.49236 B1  6   0.00000
864  88 ARG  NE   -31.92741 -14.57277  92.34607 B1  6   0.00000
865  88 ARG  HE   -31.76512 -14.64038  93.33788 B1  6   0.00000
866  88 ARG  CZ   -33.08881 -14.12165  91.86193 B1  6   0.00000
867  88 ARG  NH1  -34.06565 -13.81756  92.71322 B1  6   0.00000
868  88 ARG  HH11 -34.95441 -13.48157  92.40144 B1  6   0.00000
869  88 ARG  HH12 -33.91853 -13.92533  93.69838 B1  6   0.00000
870  88 ARG  NH2  -33.26623 -13.97383  90.54974 B1  6   0.00000
871  88 ARG  HH21 -34.12737 -13.64013  90.16725 B1  6   0.00000
872  88 ARG  HH22 -32.52080 -14.19859  89.92214 B1  6   0.00000
873  88 ARG  C    -27.23157 -17.07404  93.36366 B1  6   0.00000
874  88 ARG  O    -26.89591 -18.00090  92.63574 B1  6   0.00000
875  89 PHE  N    -27.62757 -17.24057  94.62546 B1  7   0.00000
876  89 PHE  H    -27.92346 -16.46797  95.16173 B1  7   0.00000
877  89 PHE  CA   -27.64368 -18.59443  95.17433 B1  7   0.00000
878  89 PHE  CB   -26.56379 -18.74887  96.25427 B1  7   0.00000
879  89 PHE  CG   -25.20774 -18.55805  95.61829 B1  7   0.00000
880  89 PHE  CD1  -24.74915 -19.48139  94.64858 B1  7   0.00000
881  89 PHE  CD2  -24.42840 -17.43023  95.96102 B1  7   0.00000
882  89 PHE  CE1  -23.51045 -19.27079  94.00961 B1  7   0.00000
883  89 PHE  CE2  -23.18767 -17.21976  95.32384 B1  7   0.00000
884  89 PHE  CZ   -22.73800 -18.13927  94.34976 B1  7   0.00000
885  89 PHE  C    -28.99632 -18.97147  95.72084 B1  7   0.00000
886  89 PHE  O    -29.85551 -18.12429  95.94786 B1  7   0.00000
887  90 LEU  N    -29.15755 -20.28822  95.87791 B1  8   0.00000
888  90 LEU  H    -28.36720 -20.92114  95.76376 D1  8   0.00000
889  90 LEU  CA   -30.48975 -20.02226  96.14113 B1  8   0.00000
890  90 LEU  CB   -31.01266 -21.46546  94.64981 B1  8   0.00000
891  90 LEU  CG   -32.46079 -21.16652  94.43614 B1  8   0.00000
892  90 LEU  CD1  -32.81337 -21.96230  93.19113 B1  8   0.00000
```

FIG. 15

```
./DR1_MIN2.CRD        Thu Feb 25 14:58:48 1993           15

893  90 LEU  CD2  -33.4     8 -21.40699  95.55222 B1   8   0.00000
894  90 LEU  C    -30.45467  -21.90281  97.20252 B1   8   0.00000
895  90 LEU  O    -29.74216  -22.89200  97.07224 B1   8   0.00000
896  91 TRP  N    -31.28133  -21.71086  98.22982 B1   9   0.00000
897  91 TRP  H    -31.78897  -20.85226  98.31900 B1   9   0.00000
898  91 TRP  CA   -31.61477  -22.06043  99.06700 B1   9   0.00000
899  91 TRP  CB   -31.76159  -22.50789 100.54418 B1   9   0.00000
900  91 TRP  CG   -30.46050  -22.11490 101.18157 B1   9   0.00000
901  91 TRP  CD2  -29.22893  -22.79283 101.16170 B1   9   0.00000
902  91 TRP  CE2  -28.30074  -21.96546 101.98847 B1   9   0.00000
903  91 TRP  CE3  -28.77368  -24.00327 100.60389 B1   9   0.00000
904  91 TRP  CD1  -30.26500  -20.96427 101.96112 B1   9   0.00000
905  91 TRP  NE1  -28.99810  -20.87047 102.44030 B1   9   0.00000
906  91 TRP  HE1  -28.68566  -20.15616 103.04137 B1   9   0.00000
907  91 TRP  CZ2  -26.97767  -22.40520 102.16578 B1   9   0.00000
908  91 TRP  CZ3  -27.44054  -24.40402 100.81577 B1   9   0.00000
909  91 TRP  CH2  -26.56124  -23.61859 101.58828 B1   9   0.00000
910  91 TRP  C    -32.96765  -23.39534  98.70806 B1   9   0.00000
911  91 TRP  O    -33.92486  -22.66026  98.49798 B1   9   0.00000
912  92 GLN  N    -33.02847  -24.71550  98.69197 B1  10   0.00000
913  92 GLN  H    -32.20362  -25.28365  98.76579 B1  10   0.00000
914  92 GLN  CA   -34.33516  -25.34751  98.65309 B1  10   0.00000
915  92 GLN  CB   -34.50105  -26.04119  97.30049 B1  10   0.00000
916  92 GLN  CG   -34.43267  -25.05724  96.13126 B1  10   0.00000
917  92 GLN  CD   -34.12668  -25.79390  94.84833 B1  10   0.00000
918  92 GLN  OE1  -32.99424  -25.68638  94.39010 B1  10   0.00000
919  92 GLN  NE2  -35.19268  -26.32196  94.25873 B1  10   0.00000
920  92 GLN  HE21 -36.10617  -26.21874  94.65013 B1  10   0.00000
921  92 GLN  HE22 -35.08609  -26.83019  93.40658 B1  10   0.00000
922  92 GLN  C    -34.37000  -26.35610  99.77327 B1  10   0.00000
923  92 GLN  O    -33.40619  -27.07419 100.00960 B1  10   0.00000
924  93 LEU  N    -35.49484  -26.39205 100.47380 B1  11   0.00000
925  93 LEU  H    -36.24432  -25.74963 100.29272 B1  11   0.00000
926  93 LEU  CA   -35.59559  -27.43909 101.48633 B1  11   0.00000
927  93 LEU  CB   -35.41178  -26.81504 102.88181 B1  11   0.00000
928  93 LEU  CG   -34.83577  -27.70766 103.99848 B1  11   0.00000
929  93 LEU  CD1  -34.33031  -26.83624 105.14843 B1  11   0.00000
930  93 LEU  CD2  -35.82812  -28.74167 104.52805 B1  11   0.00000
931  93 LEU  C    -36.93596  -28.11112 101.32695 B1  11   0.00000
932  93 LEU  O    -37.91692  -27.47571 100.96621 B1  11   0.00000
933  94 LYS  N    -36.95045  -29.41719 101.56549 B1  12   0.00000
934  94 LYS  H    -36.10205  -29.89066 101.79736 B1  12   0.00000
935  94 LYS  CA   -38.21063  -30.14121 101.49214 B1  12   0.00000
936  94 LYS  CB   -38.26049  -30.88530 100.13839 B1  12   0.00000
937  94 LYS  CG   -39.43761  -31.85442 100.07544 B1  12   0.00000
938  94 LYS  CD   -39.91969  -32.44832  98.75113 B1  12   0.00000
939  94 LYS  CE   -41.00198  -33.40442  99.23924 B1  12   0.00000
940  94 LYS  NZ   -41.98389  -33.90963  98.26846 B1  12   0.00000
941  94 LYS  HZ1  -42.69798  -34.41995  98.86351 B1  12   0.00000
942  94 LYS  HZ2  -42.69249  -33.14263  97.78947 B1  12   0.00000
943  94 LYS  HZ3  -41.57162  -34.57937  97.59540 B1  12   0.00000
944  94 LYS  C    -38.34510  -31.08699 102.67642 B1  12   0.00000
945  94 LYS  O    -37.54720  -31.99770 102.85849 B1  12   0.00000
946  95 PHE  N    -39.60676  -30.85929 103.46609 B1  13   0.00000
947  95 PHE  H    -39.99321  -30.05201 103.34519 B1  13   0.00000
948  95 PHE  CA   -39.73794  -31.84982 104.49053 B1  13   0.00000
949  95 PHE  CB   -39.13251  -31.49228 105.86481 B1  13   0.00000
950  95 PHE  CG   -39.62104  -30.20819 106.49960 B1  13   0.00000
951  95 PHE  CD1  -39.04917  -28.96886 106.12996 B1  13   0.00000
952  95 PHE  CD2  -40.60668  -30.26479 107.51173 B1  13   0.00000
953  95 PHE  CE1  -39.45587  -27.78326 106.77985 B1  13   0.00000
954  95 PHE  CE2  -41.01477  -29.08019 108.16313 B1  13   0.00000
955  95 PHE  CZ   -40.43557  -27.84435 107.79605 B1  13   0.00000
956  95 PHE  C    -41.22005  -32.16799 104.57423 B1  13   0.00000
```

FIG. 16

./DRJ_ND2.CRD        Thu Feb 25 14:58:48 1993         16

```
957    95 PHE  O    -42.0.    : -31.31332 104.41691 B1   13   0.00000
958    96 GLU  N    -41.47812 -33.46734 104.75822 B1   14   0.00000
959    96 GLU  H    -40.74093 -34.09071 105.01948 B1   14   0.00000
960    96 GLU  CA   -42.80002 -33.99059 104.40078 B1   14   0.00000
961    96 GLU  CB   -42.75085 -34.25375 102.88321 B1   14   0.00000
962    96 GLU  CG   -43.92070 -34.87965 102.11791 B1   14   0.00000
963    96 GLU  CD   -43.55585 -34.92496 100.64018 B1   14   0.00000
964    96 GLU  OE1  -44.08205 -34.15253  99.84297 B1   14   0.00000
965    96 GLU  OE2  -42.67962 -35.68559 100.23154 B1   14   0.00000
966    96 GLU  C    -43.13129 -35.25393 105.17925 B1   14   0.00000
967    96 GLU  O    -42.27510 -36.11395 105.37879 B1   14   0.00000
968    97 CYS  N    -44.39621 -35.34431 105.62501 B1   15   0.00000
969    97 CYS  H    -45.05281 -34.60566 105.44206 B1   15   0.00000
970    97 CYS  CA   -44.78990 -36.60747 106.25700 B1   15   0.00000
971    97 CYS  CB   -45.09404 -36.46870 107.76554 B1   15   0.00000
972    97 CYS  SG   -46.49873 -35.54248 108.42288 B1   15   0.00000
973    97 CYS  C    -45.89248 -37.36966 105.55706 B1   15   0.00000
974    97 CYS  O    -46.75253 -36.80546 104.88787 B1   15   0.00000
975    98 HIS  N    -45.80356 -38.69951 105.71784 B1   16   0.00000
976    98 HIS  H    -45.06854 -39.11332 106.26371 B1   16   0.00000
977    98 HIS  CA   -46.75592 -39.59530 105.05785 B1   16   0.00000
978    98 HIS  CB   -46.00867 -40.61029 104.19437 B1   16   0.00000
979    98 HIS  CG   -45.38253 -39.98357 102.97364 B1   16   0.00000
980    98 HIS  ND1  -45.88967 -40.13539 101.74183 B1   16   0.00000
981    98 HIS  HD1  -46.72307 -40.60043 101.51181 B1   16   0.00000
982    98 HIS  CD2  -44.21286 -39.22166 102.89430 B1   16   0.00000
983    98 HIS  NE2  -44.02278 -38.92334 101.58753 B1   16   0.00000
984    98 HIS  CE1  -45.05268 -39.48082 100.87633 B1   16   0.00000
985    98 HIS  C    -47.56750 -40.40062 106.05217 B1   16   0.00000
986    98 HIS  O    -47.04279 -40.99638 106.99225 B1   16   0.00000
987    99 PHE  N    -48.87987 -40.39547 105.81218 B1   17   0.00000
988    99 PHE  H    -49.25243 -39.92869 105.00666 B1   17   0.00000
989    99 PHE  CA   -49.78029 -41.01889 106.77662 B1   17   0.00000
990    99 PHE  CB   -50.48946 -39.93190 107.59234 B1   17   0.00000
991    99 PHE  CG   -49.63868 -39.72312 108.81497 B1   17   0.00000
992    99 PHE  CD1  -48.50685 -38.87580 108.76543 B1   17   0.00000
993    99 PHE  CD2  -49.92563 -40.47457 109.97439 B1   17   0.00000
994    99 PHE  CE1  -47.64103 -38.80002 109.87537 B1   17   0.00000
995    99 PHE  CE2  -49.06252 -40.39779 111.08354 B1   17   0.00000
996    99 PHE  CZ   -47.92137 -39.56658 111.02626 B1   17   0.00000
997    99 PHE  C    -50.79242 -41.97404 106.19800 B1   17   0.00000
998    99 PHE  O    -51.48007 -41.71068 105.22101 B1   17   0.00000
999   100 PHE  N    -50.86837 -43.12653 106.85814 B1   18   0.00000
1000  100 PHE  H    -50.32768 -43.27017 107.68944 B1   18   0.00000
1001  100 PHE  CA   -51.84718 -44.10783 106.41132 B1   18   0.00000
1002  100 PHE  CB   -51.44468 -45.52210 106.04262 B1   18   0.00000
1003  100 PHE  CG   -51.08740 -46.34931 105.63001 B1   18   0.00000
1004  100 PHE  CD1  -49.81159 -46.95065 105.55366 B1   18   0.00000
1005  100 PHE  CD2  -52.01269 -46.50158 104.56911 B1   18   0.00000
1006  100 PHE  CE1  -49.45012 -47.69723 104.41336 B1   18   0.00000
1007  100 PHE  CE2  -51.65494 -47.24829 103.42719 B1   18   0.00000
1008  100 PHE  CZ   -50.37408 -47.83859 103.35608 B1   18   0.00000
1009  100 PHE  C    -53.21727 -43.84401 106.96975 B1   18   0.00000
1010  100 PHE  O    -53.38235 -43.49692 108.13319 B1   18   0.00000
1011  101 ASN  N    -54.19611 -44.08275 106.08672 B1   19   0.00000
1012  101 ASN  H    -53.92777 -44.29429 105.14366 B1   19   0.00000
1013  101 ASN  CA   -55.63451 -43.97453 106.37273 B1   19   0.00000
1014  101 ASN  CB   -56.35400 -45.03359 105.52094 B1   19   0.00000
1015  101 ASN  CG   -57.86040 -44.63624 105.52911 B1   19   0.00000
1016  101 ASN  OD1  -58.43246 -44.06601 104.77523 B1   19   0.00000
1017  101 ASN  ND2  -58.51327 -45.52184 106.41359 B1   19   0.00000
1018  101 ASN  HD21 -58.04843 -46.21753 107.02623 B1   19   0.00000
1019  101 ASN  HD22 -59.50666 -45.49785 106.46682 B1   19   0.00000
1020  101 ASN  C    -56.06277 -44.09262 107.83398 B1   19   0.00000
```

FIG. 17

```
/CR1_NCR2.CRD        Thu Feb 25 14:58:48 1993        27

1021  101 ASN   O    -56.77   7 -43.23997 108.39463 B1   19   0.00000
1022  102 GLY   N    -55.6.   0 -45.10941 108.46454 B1   20   0.00000
1023  102 GLY   H    -55.00370 -45.02188 108.01935 B1   20   0.00000
1024  102 GLY   CA   -55.97438 -45.32353 109.88157 B1   20   0.00000
1025  102 GLY   C    -55.02088 -44.59872 110.81953 B1   20   0.00000
1026  102 GLY   O    -54.46008 -45.17864 111.73800 B1   20   0.00000
1027  103 THR   N    -54.84744 -43.29716 110.54648 B1   21   0.00000
1028  103 THR   H    -55.35512 -42.90731 109.77435 B1   21   0.00000
1029  103 THR   CA   -53.96549 -42.39542 111.30363 B1   21   0.00000
1030  103 THR   CB   -54.75487 -41.81263 112.51011 B1   21   0.00000
1031  103 THR   OG1  -54.22405 -40.53356 112.87483 B1   21   0.00000
1032  103 THR   HG1  -54.81974 -40.09919 113.49221 B1   21   0.00000
1033  103 THR   CG2  -54.86925 -42.72433 113.73959 B1   21   0.00000
1034  103 THR   C    -52.56983 -42.92386 111.66956 B1   21   0.00000
1035  103 THR   O    -51.96086 -42.59288 112.68707 B1   21   0.00000
1036  104 GLU   N    -52.05837 -43.78433 110.78327 B1   22   0.00000
1037  104 GLU   H    -52.50836 -43.94021 109.90068 B1   22   0.00000
1038  104 GLU   CA   -50.80234 -44.42458 111.16198 B1   22   0.00000
1039  104 GLU   CB   -50.88647 -45.95191 111.05395 B1   22   0.00000
1040  104 GLU   CG   -51.13368 -46.62525 112.41591 B1   22   0.00000
1041  104 GLU   CD   -50.07267 -46.21410 113.43075 B1   22   0.00000
1042  104 GLU   OE1  -50.42273 -45.91599 114.57130 B1   22   0.00000
1043  104 GLU   OE2  -48.89658 -46.13148 113.08359 B1   22   0.00000
1044  104 GLU   C    -49.56607 -43.91901 110.45954 B1   22   0.00000
1045  104 GLU   O    -49.58628 -43.40196 109.34894 B1   22   0.00000
1046  105 ARG   N    -48.46470 -44.04978 111.19345 B1   23   0.00000
1047  105 ARG   H    -48.46820 -44.67995 111.97754 B1   23   0.00000
1048  105 ARG   CA   -47.23862 -43.36578 110.79677 B1   23   0.00000
1049  105 ARG   CB   -46.43619 -43.14957 112.09184 B1   23   0.00000
1050  105 ARG   CG   -45.11167 -42.37595 112.05228 B1   23   0.00000
1051  105 ARG   CD   -43.69570 -43.22016 111.65081 B1   23   0.00000
1052  105 ARG   NE   -42.65640 -42.46704 111.89499 B1   23   0.00000
1053  105 ARG   HE   -42.30777 -42.45915 112.83941 B1   23   0.00000
1054  105 ARG   CZ   -42.05554 -41.77685 110.93892 B1   23   0.00000
1055  105 ARG   NH1  -41.02352 -41.00938 111.25165 B1   23   0.00000
1056  105 ARG   HH11 -40.51476 -40.49136 110.56874 B1   23   0.00000
1057  105 ARG   HH12 -40.73208 -40.92747 112.21979 B1   23   0.00000
1058  105 ARG   NH2  -42.47661 -41.82718 109.68286 B1   23   0.00000
1059  105 ARG   HH21 -42.19810 -41.15340 109.00310 B1   23   0.00000
1060  105 ARG   HH22 -43.08503 -42.57763 109.38941 B1   23   0.00000
1061  105 ARG   C    -46.47373 -44.13883 109.74376 B1   23   0.00000
1062  105 ARG   O    -46.02105 -45.25363 109.97034 B1   23   0.00000
1063  106 VAL   N    -46.32883 -43.51517 108.56827 B1   24   0.00000
1064  106 VAL   H    -46.72693 -42.61352 108.37187 B1   24   0.00000
1065  106 VAL   CA   -45.53349 -44.24499 107.58352 B1   24   0.00000
1066  106 VAL   CB   -46.27081 -44.39073 106.24298 B1   24   0.00000
1067  106 VAL   CG1  -45.79579 -45.65575 105.52366 B1   24   0.00000
1068  106 VAL   CG2  -47.77990 -44.41166 106.42922 B1   24   0.00000
1069  106 VAL   C    -44.14065 -43.66075 107.41554 B1   24   0.00000
1070  106 VAL   O    -43.30354 -43.60891 108.29696 B1   24   0.00000
1071  107 ARG   N    -43.87314 -42.98069 106.29416 B1   25   0.00000
1072  107 ARG   H    -44.58452 -42.69040 105.65671 B1   25   0.00000
1073  107 ARG   CA   -42.49561 -42.53115 106.12329 B1   25   0.00000
1074  107 ARG   CB   -41.95685 -43.01317 104.76032 B1   25   0.00000
1075  107 ARG   CG   -41.96328 -42.02619 103.58362 B1   25   0.00000
1076  107 ARG   CD   -42.33357 -42.66829 102.24883 B1   25   0.00000
1077  107 ARG   NE   -43.76838 -42.93515 102.23147 B1   25   0.00000
1078  107 ARG   HE   -44.37946 -42.14312 102.28284 B1   25   0.00000
1079  107 ARG   CZ   -44.26510 -44.17490 102.20945 B1   25   0.00000
1080  107 ARG   NH1  -45.56598 -44.32747 102.35905 B1   25   0.00000
1081  107 ARG   HH11 -46.00629 -45.19207 102.34562 B1   25   0.00000
1082  107 ARG   HH12 -46.19539 -43.55730 102.54612 B1   25   0.00000
1083  107 ARG   HH2  -43.47963 -45.23695 102.05799 B1   25   0.00000
1084  107 ARG   HH21 -43.86541 -46.15096 102.05452 B1   25   0.00000
```

FIG. 18

```
./DNA_KIN2.CRD              Thu Feb 25 14:58:48 1993              18

1085  107 ARG  HH22  -42.04    -45.11957  101.94496 B1  25   0.00000
1086  107 ARG  C     -42.37787 -41.03546  106.32504 B1  25   0.00000
1087  107 ARG  O     -43.36896 -40.31981  106.43645 B1  25   0.00000
1088  108 LEU  N     -41.12633 -40.58602  106.39627 B1  26   0.00000
1089  108 LEU  H     -40.32617 -41.17985  106.29320 B1  26   0.00000
1090  108 LEU  CA    -40.89942 -39.15744  106.53751 B1  26   0.00000
1091  108 LEU  CB    -40.80087 -38.80954  108.01248 B1  26   0.00000
1092  108 LEU  CG    -41.96347 -37.89689  108.35874 B1  26   0.00000
1093  108 LEU  CD1   -42.75820 -38.44729  109.53808 B1  26   0.00000
1094  108 LEU  CD2   -41.50070 -36.44650  108.50151 B1  26   0.00000
1095  108 LEU  C     -39.62061 -38.77273  105.85764 B1  26   0.00000
1096  108 LEU  O     -38.76368 -39.61093  105.60154 B1  26   0.00000
1097  109 LEU  N     -39.52150 -37.47828  105.56773 B1  27   0.00000
1098  109 LEU  H     -40.28459 -36.84167  105.72467 B1  27   0.00000
1099  109 LEU  CA    -38.30683 -37.02679  104.90334 B1  27   0.00000
1100  109 LEU  CB    -38.47418 -37.24039  103.39009 B1  27   0.00000
1101  109 LEU  CG    -39.74490 -36.59695  102.82634 B1  27   0.00000
1102  109 LEU  CD1   -39.42210 -35.25631  102.17066 B1  27   0.00000
1103  109 LEU  CD2   -40.49190 -37.56523  101.91138 B1  27   0.00000
1104  109 LEU  C     -37.99969 -35.58061  105.21268 B1  27   0.00000
1105  109 LEU  O     -38.88411 -34.77322  105.47943 B1  27   0.00000
1106  110 GLU  N     -36.70092 -35.29768  105.12126 B1  28   0.00000
1107  110 GLU  H     -36.01498 -36.01786  105.00992 B1  28   0.00000
1108  110 GLU  CA    -36.20315 -33.92985  105.08184 B1  28   0.00000
1109  110 GLU  CB    -35.80977 -33.47627  106.49578 B1  28   0.00000
1110  110 GLU  CG    -35.32216 -32.02210  106.60993 B1  28   0.00000
1111  110 GLU  CD    -33.83808 -31.67178  106.30413 B1  28   0.00000
1112  110 GLU  OE1   -33.37957 -30.74951  106.10521 B1  28   0.00000
1113  110 GLU  OE2   -33.05671 -32.85201  106.36691 B1  28   0.00000
1114  110 GLU  C     -35.01026 -33.94076  104.15500 B1  28   0.00000
1115  110 GLU  O     -34.25577 -34.90807  104.11585 B1  28   0.00000
1116  111 ARG  N     -34.89439 -32.86843  103.37222 B1  29   0.00000
1117  111 ARG  H     -35.61365 -32.16766  103.37387 B1  29   0.00000
1118  111 ARG  CA    -33.75645 -32.74903  102.46249 B1  29   0.00000
1119  111 ARG  CB    -33.99004 -33.60407  101.20352 B1  29   0.00000
1120  111 ARG  CG    -35.45106 -33.70037  100.75305 B1  29   0.00000
1121  111 ARG  CD    -35.67880 -34.83036   99.75174 B1  29   0.00000
1122  111 ARG  NE    -37.09124 -35.21147   99.72614 B1  29   0.00000
1123  111 ARG  HE    -37.71860 -34.61357  100.22757 B1  29   0.00000
1124  111 ARG  CZ    -37.50098 -36.32384   99.09789 B1  29   0.00000
1125  111 ARG  NH1   -38.78119 -36.68971   99.16119 B1  29   0.00000
1126  111 ARG  HH11  -39.12269 -37.49888   98.68276 B1  29   0.00000
1127  111 ARG  HH12  -39.43712 -36.16699   99.70960 B1  29   0.00000
1128  111 ARG  NH2   -36.63391 -37.06893   98.41518 B1  29   0.00000
1129  111 ARG  HH21  -36.91501 -37.90348   97.94325 B1  29   0.00000
1130  111 ARG  HH22  -35.67503 -36.78688   98.36264 B1  29   0.00000
1131  111 ARG  C     -33.69135 -31.31194  102.08170 B1  29   0.00000
1132  111 ARG  O     -34.39395 -30.54569  101.76699 B1  29   0.00000
1133  112 CYS  N     -32.20568 -30.97057  102.12414 B1  30   0.00000
1134  112 CYS  H     -31.50733 -31.64380  102.37455 B1  30   0.00000
1135  112 CYS  CA    -31.80458 -29.62360  101.73826 B1  30   0.00000
1136  112 CYS  CB    -31.12874 -28.92365  102.91930 B1  30   0.00000
1137  112 CYS  SG    -30.70297 -27.19555  102.57697 B1  30   0.00000
1138  112 CYS  C     -30.87368 -29.64998  100.54300 B1  30   0.00000
1139  112 CYS  O     -29.97769 -30.48052  100.40406 B1  30   0.00000
1140  113 ILE  N     -31.15975 -28.70696   99.65078 B1  31   0.00000
1141  113 ILE  H     -31.84393 -28.00116   99.86111 B1  31   0.00000
1142  113 ILE  CA    -30.55306 -28.70228   98.32464 B1  31   0.00000
1143  113 ILE  CB    -31.56021 -29.33526   97.30706 B1  31   0.00000
1144  113 ILE  CG2   -33.00339 -29.37434   97.82323 B1  31   0.00000
1145  113 ILE  CG1   -31.52431 -28.74184   95.85635 B1  31   0.00000
1146  113 ILE  CD    -32.44057 -29.50025   94.93272 B1  31   0.00000
1147  113 ILE  C     -30.08576 -27.29665   97.96535 B1  31   0.00000
1148  113 ILE  O     -30.75333 -26.29900   98.21317 B1  31   0.00000
```

FIG. 19

```
     2 CPD           Thu Feb 25 14:58:48 1993        19

..  114 TYR  N     -28. /10  -27.25564  97.41665 B1   32   0.00000
1150  114 TYR  H     -28.42970 -28.10151  97.10297 B1   32   0.00000
1151  114 TYR  CA    -28.22036 -25.98264  97.11462 B1   32   0.00000
1152  114 TYR  CB    -26.80088 -26.01933  97.71345 B1   32   0.00000
1153  114 TYR  CG    -26.01127 -24.72107  97.61311 B1   32   0.00000
1154  114 TYR  CD1   -26.62770 -23.45825  97.79068 B1   32   0.00000
1155  114 TYR  CE1   -25.84886 -22.28083  97.75267 B1   32   0.00000
1156  114 TYR  CD2   -24.61824 -24.80211  97.38751 B1   32   0.00000
1157  114 TYR  CE2   -23.83841 -23.62651  97.34588 B1   32   0.00000
1158  114 TYR  CZ    -24.45600 -22.36940  97.53154 B1   32   0.00000
1159  114 TYR  OH    -23.68967 -21.21917  97.50979 B1   32   0.00000
1160  114 TYR  HH    -22.79676 -21.43015  97.21984 B1   32   0.00000
1161  114 TYR  C     -28.34723 -25.83215  95.61430 B1   32   0.00000
1162  114 TYR  O     -27.66375 -26.70965  94.91236 B1   32   0.00000
1163  115 ASN  N     -28.66823 -24.69995  95.12919 B1   33   0.00000
1164  115 ASN  H     -29.03092 -24.02391  95.77643 B1   33   0.00000
1165  115 ASN  CA    -28.63762 -24.41545  93.68566 B1   33   0.00000
1166  115 ASN  CB    -27.27049 -23.84385  93.27078 B1   33   0.00000
1167  115 ASN  CG    -27.00239 -22.43118  93.78440 B1   33   0.00000
1168  115 ASN  OD1   -26.55389 -22.16954  94.85370 B1   33   0.00000
1169  115 ASN  ND2   -27.51765 -21.48359  92.96271 B1   33   0.00000
1170  115 ASN  HD21  -28.04883 -21.70692  92.14797 B1   33   0.00000
1171  115 ASN  HD22  -27.29503 -20.52370  93.13946 B1   33   0.00000
1172  115 ASN  C     -28.96318 -25.59300  92.77321 B1   33   0.00000
1173  115 ASN  O     -28.22150 -25.91402  91.85250 B1   33   0.00000
1174  116 GLN  N     -30.10651 -26.23583  93.07767 B1   34   0.00000
1175  116 GLN  H     -30.66790 -25.52614  93.84630 B1   34   0.00000
1176  116 GLN  CA    -30.60575 -27.38897  92.31212 B1   34   0.00000
1177  116 GLN  CB    -30.73906 -26.98635  90.82631 B1   34   0.00000
1178  116 GLN  CG    -31.33401 -27.96419  89.80983 B1   34   0.00000
1179  116 GLN  CD    -31.33954 -27.31473  88.43568 B1   34   0.00000
1180  116 GLN  OE1   -32.32002 -27.33002  87.70605 B1   34   0.00000
1181  116 GLN  NE2   -30.20428 -26.71450  88.08185 B1   34   0.00000
1182  116 GLN  HE21  -29.39553 -26.71396  88.67007 B1   34   0.00000
1183  116 GLN  HE22  -30.15594 -26.24641  87.20205 B1   34   0.00000
1184  116 GLN  C     -29.89899 -28.73663  92.53043 B1   34   0.00000
1185  116 GLN  O     -30.38571 -29.77693  92.10767 B1   34   0.00000
1186  117 GLU  N     -28.76921 -28.72803  93.24838 B1   35   0.00000
1187  117 GLU  H     -28.34990 -27.88576  93.59525 B1   35   0.00000
1188  117 GLU  CA    -28.17324 -30.02538  93.58636 B1   35   0.00000
1189  117 GLU  CB    -26.68237 -30.02305  93.23572 B1   35   0.00000
1190  117 GLU  CG    -26.41125 -29.71932  91.75724 B1   35   0.00000
1191  117 GLU  CD    -24.93459 -29.87167  91.43636 B1   35   0.00000
1192  117 GLU  OE1   -24.62388 -30.40776  90.37359 B1   35   0.00000
1193  117 GLU  OE2   -24.09945 -29.45965  92.24135 B1   35   0.00000
1194  117 GLU  C     -28.34342 -30.39133  95.05360 B1   35   0.00000
1195  117 GLU  O     -28.39032 -29.54087  95.93593 B1   35   0.00000
1196  118 GLU  N     -28.45418 -31.70267  95.31151 B1   36   0.00000
1197  118 GLU  H     -28.37884 -32.37663  94.57056 B1   36   0.00000
1198  118 GLU  CA    -20.64640 -32.12718  96.70504 B1   36   0.00000
1199  118 GLU  CB    -28.86529 -33.64399  96.80220 B1   36   0.00000
1200  118 GLU  CG    -30.04821 -34.25904  96.04454 B1   36   0.00000
1201  118 GLU  CD    -30.18685 -35.73854  96.39969 B1   36   0.00000
1202  118 GLU  OE1   -31.31366 -36.18518  96.62004 B1   36   0.00000
1203  118 GLU  OE2   -29.17775 -36.44658  96.46236 B1   36   0.00000
1204  118 GLU  C     -27.45968 -31.79603  97.59954 B1   36   0.00000
1205  118 GLU  O     -26.30375 -31.93771  97.22004 B1   36   0.00000
1206  119 SER  N     -27.77719 -31.35385  98.81871 B1   37   0.00000
1207  119 SER  H     -28.73032 -31.22468  99.10568 B1   37   0.00000
1208  119 SER  CA    -26.67523 -31.09310  99.74333 B1   37   0.00000
1209  119 SER  CB    -26.79679 -29.64425 100.25438 B1   37   0.00000
1210  119 SER  OG    -25.62406 -29.23340 100.96654 B1   37   0.00000
1211  119 SER  HG    -25.73940 -28.33730 101.30354 B1   37   0.00000
1212  119 SER  C     -26.64967 -32.10855 100.87559 B1   37   0.00000
```

FIG. 20

```
/DR1 KIN2.CRD        Thu Feb 25 14:58:48 1993        20

1213  119 SER  O    -25.7.. .8 -32.90554 101.03211 B1  37   0.00000
1214  120 VAL  N    -27.72434 -32.06808 101.67561 B1  38   0.00000
1215  120 VAL  H    -28.50026 -31.45938 101.48344 B1  38   0.00000
1216  120 VAL  CA   -27.82678 -32.99802 102.80099 B1  38   0.00000
1217  120 VAL  CB   -27.44790 -32.32244 104.13888 B1  38   0.00000
1218  120 VAL  CG1  -25.93252 -32.18078 104.29388 B1  38   0.00000
1219  120 VAL  CG2  -28.15631 -30.97900 104.33500 B1  38   0.00000
1220  120 VAL  C    -29.23777 -33.53625 102.89372 B1  38   0.00000
1221  120 VAL  O    -30.19812 -32.88656 102.49711 B1  38   0.00000
1222  121 ARG  N    -29.34164 -34.75356 103.41944 B1  39   0.00000
1223  121 ARG  H    -28.52525 -35.27675 103.67737 B1  39   0.00000
1224  121 ARG  CA   -30.65941 -35.37282 103.49447 B1  39   0.00000
1225  121 ARG  CB   -30.83879 -36.26556 102.25451 B1  39   0.00000
1226  121 ARG  CG   -32.24891 -36.83907 102.13977 B1  39   0.00000
1227  121 ARG  CD   -32.36448 -38.11228 101.31436 B1  39   0.00000
1228  121 ARG  NE   -33.46636 -38.89614 101.86585 B1  39   0.00000
1229  121 ARG  HE   -33.58314 -38.82444 102.86363 B1  39   0.00000
1230  121 ARG  CZ   -34.21779 -39.71705 101.13259 B1  39   0.00000
1231  121 ARG  NH1  -35.18842 -40.40193 101.73316 B1  39   0.00000
1232  121 ARG  HH11 -35.77971 -41.03741 101.23780 B1  39   0.00000
1233  121 ARG  HH12 -35.33365 -40.28453 102.71808 B1  39   0.00000
1234  121 ARG  NH2  -33.99786 -39.84536  99.82444 B1  39   0.00000
1235  121 ARG  HH21 -34.53079 -40.47140  99.25675 B1  39   0.00000
1236  121 ARG  HH22 -33.27054 -39.30635  99.39731 B1  39   0.00000
1237  121 ARG  C    -30.80743 -36.21013 104.75602 B1  39   0.00000
1238  121 ARG  O    -29.86515 -36.82872 105.23483 B1  39   0.00000
1239  122 PHE  N    -32.04075 -36.24055 105.26404 B1  40   0.00000
1240  122 PHE  H    -32.75061 -35.63810 104.89111 B1  40   0.00000
1241  122 PHE  CA   -32.40668 -37.26064 106.24769 B1  40   0.00000
1242  122 PHE  CB   -33.75724 -36.87165 106.85296 B1  40   0.00000
1243  122 PHE  CG   -33.64992 -36.46831 108.30418 B1  40   0.00000
1244  122 PHE  CD1  -32.56100 -35.69712 108.77664 B1  40   0.00000
1245  122 PHE  CD2  -34.66985 -36.87929 109.19094 B1  40   0.00000
1246  122 PHE  CE1  -32.49275 -35.34303 110.14035 B1  40   0.00000
1247  122 PHE  CE2  -34.60187 -36.52254 110.55431 B1  40   0.00000
1248  122 PHE  CZ   -33.51285 -35.75823 111.02379 B1  40   0.00000
1249  122 PHE  C    -32.57844 -38.62424 105.60697 B1  40   0.00000
1250  122 PHE  O    -33.34168 -38.79208 104.65587 B1  40   0.00000
1251  123 ASP  N    -31.06201 -39.60796 106.15389 B1  41   0.00000
1252  123 ASP  H    -31.23184 -39.47015 106.92548 B1  41   0.00000
1253  123 ASP  CA   -32.08552 -40.93522 105.58825 B1  41   0.00000
1254  123 ASP  CB   -30.85171 -41.81726 105.76445 B1  41   0.00000
1255  123 ASP  CG   -29.93161 -41.56041 104.59405 B1  41   0.00000
1256  123 ASP  OD1  -28.81173 -41.11310 104.61757 B1  41   0.00000
1257  123 ASP  OD2  -30.34905 -41.80191 103.45856 B1  41   0.00000
1258  123 ASP  C    -33.32362 -41.63618 106.09965 B1  41   0.00000
1259  123 ASP  O    -34.00966 -41.21121 107.02319 B1  41   0.00000
1260  124 SER  N    -33.62443 -42.74250 105.41429 B1  42   0.00000
1261  124 SER  H    -32.95329 -43.10971 104.76900 B1  42   0.00000
1262  124 SER  CA   -34.94425 -43.35498 105.58880 B1  42   0.00000
1263  124 SER  CB   -35.18779 -44.37028 104.46149 B1  42   0.00000
1264  124 SER  OG   -36.57945 -44.70776 104.37671 B1  42   0.00000
1265  124 SER  HG   -36.91089 -44.87590 105.27413 B1  42   0.00000
1266  124 SER  C    -35.21640 -44.01057 106.93634 B1  42   0.00000
1267  124 SER  O    -36.33538 -44.42223 107.22372 B1  42   0.00000
1268  125 ASP  N    -34.16447 -44.10325 107.74330 B1  43   0.00000
1269  125 ASP  H    -33.26228 -43.73425 107.50494 B1  43   0.00000
1270  125 ASP  CA   -34.30492 -44.60689 109.10471 B1  43   0.00000
1271  125 ASP  CB   -32.96210 -45.24580 109.50620 B1  43   0.00000
1272  125 ASP  CG   -31.82155 -44.23245 109.55779 B1  43   0.00000
1273  125 ASP  OD1  -31.89194 -43.19553 108.89075 B1  43   0.00000
1274  125 ASP  OD2  -30.67249 -44.45676 110.29614 B1  43   0.00000
1275  125 ASP  C    -34.65374 -43.52244 110.10428 B1  43   0.00000
1276  125 ASP  O    -35.10540 -43.75441 111.22672 B1  43   0.00000
```

FIG. 21

```
./DR1_MIN2.CRD            Thu Feb 25 14:58:48 1993        21

1277  126 VAL  N    -34.51305 -42.26751 109.64790 B1  44   0.00000
1278  126 VAL  H    -34.20939 -42.12308 108.70456 B1  44   0.00000
1279  126 VAL  CA   -34.59346 -41.07914 110.50496 B1  44   0.00000
1280  126 VAL  CB   -36.04814 -40.82462 110.97592 B1  44   0.00000
1281  126 VAL  CG1  -36.22164 -39.41758 111.54094 B1  44   0.00000
1282  126 VAL  CG2  -37.04494 -41.00281 109.82481 B1  44   0.00000
1283  126 VAL  C    -33.57625 -41.13739 111.64961 B1  44   0.00000
1284  126 VAL  O    -33.78819 -40.75401 112.79533 B1  44   0.00000
1285  127 GLY  N    -32.41541 -41.66443 111.25324 B1  45   0.00000
1286  127 GLY  H    -32.31598 -42.01122 110.31755 B1  45   0.00000
1287  127 GLY  CA   -31.32244 -41.88201 112.19529 B1  45   0.00000
1288  127 GLY  C    -29.94594 -41.56889 111.62542 B1  45   0.00000
1289  127 GLY  O    -29.03055 -41.23776 112.35962 B1  45   0.00000
1290  128 GLU  N    -29.81143 -41.65704 110.29545 B1  46   0.00000
1291  128 GLU  H    -30.48653 -42.13586 109.72534 B1  46   0.00000
1292  128 GLU  CA   -28.56256 -41.14297 109.73120 B1  46   0.00000
1293  128 GLU  CB   -27.75197 -42.29481 109.11709 B1  46   0.00000
1294  128 GLU  CG   -26.29316 -42.25781 109.59860 B1  46   0.00000
1295  128 GLU  CD   -25.44181 -43.20422 108.87693 B1  46   0.00000
1296  128 GLU  OE1  -24.49646 -42.88073 108.19992 B1  46   0.00000
1297  128 GLU  OE2  -25.71010 -44.47773 109.00348 B1  46   0.00000
1298  128 GLU  C    -28.71376 -39.98012 108.75031 B1  46   0.00000
1299  128 GLU  O    -29.80604 -39.57375 108.35724 B1  46   0.00000
1300  129 TYR  N    -27.54735 -39.42619 108.38931 B1  47   0.00000
1301  129 TYR  H    -26.68498 -39.83420 108.68820 B1  47   0.00000
1302  129 TYR  CA   -27.50019 -38.29654 107.46434 B1  47   0.00000
1303  129 TYR  CB   -26.63842 -37.15326 108.01560 B1  47   0.00000
1304  129 TYR  CG   -27.30857 -36.34222 109.09443 B1  47   0.00000
1305  129 TYR  CD1  -26.67181 -36.21958 110.34811 B1  47   0.00000
1306  129 TYR  CE1  -27.25566 -35.42131 111.35148 B1  47   0.00000
1307  129 TYR  CD2  -28.52827 -35.67832 108.83210 B1  47   0.00000
1308  129 TYR  CE2  -29.11235 -34.88063 109.83571 B1  47   0.00000
1309  129 TYR  CZ   -28.47327 -34.75726 111.08860 B1  47   0.00000
1310  129 TYR  OH   -29.05005 -33.98459 112.07221 B1  47   0.00000
1311  129 TYR  HH   -29.70394 -33.40059 111.67732 B1  47   0.00000
1312  129 TYR  C    -26.82531 -38.64304 106.15941 B1  47   0.00000
1313  129 TYR  O    -25.66697 -39.04407 106.10492 B1  47   0.00000
1314  130 ARG  N    -27.55686 -38.39162 105.08581 B1  48   0.00000
1315  130 ARG  H    -28.51666 -38.10451 105.16735 B1  48   0.00000
1316  130 ARG  CA   -26.07326 -38.41254 103.80227 B1  48   0.00000
1317  130 ARG  CB   -27.85650 -38.84659 102.71647 B1  48   0.00000
1318  130 ARG  CG   -27.21143 -39.00526 101.34112 B1  48   0.00000
1319  130 ARG  CD   -28.23975 -39.41974 100.29808 B1  48   0.00000
1320  130 ARG  NE   -27.66322 -39.38333  98.95629 B1  48   0.00000
1321  130 ARG  HE   -26.82589 -38.85034  98.82833 B1  48   0.00000
1322  130 ARG  CZ   -28.29934 -39.96348  97.93202 B1  48   0.00000
1323  130 ARG  NH1  -27.82365 -39.81313  96.69917 B1  48   0.00000
1324  130 ARG  HH11 -28.26738 -40.23513  95.90996 B1  48   0.00000
1325  130 ARG  HH12 -27.01064 -39.25297  96.53955 B1  48   0.00000
1326  130 ARG  NH2  -29.39843 -40.68730  98.14392 B1  48   0.00000
1327  130 ARG  HH21 -29.90446 -41.10492  97.39118 B1  48   0.00000
1328  130 ARG  HH22 -29.72741 -40.81930  99.07957 B1  48   0.00000
1329  130 ARG  C    -26.28004 -37.06053 103.45986 B1  48   0.00000
1330  130 ARG  O    -26.96293 -36.11772 103.07688 B1  48   0.00000
1331  131 ALA  N    -24.95816 -36.99899 103.58668 B1  49   0.00000
1332  131 ALA  H    -24.45069 -37.77908 103.95192 B1  49   0.00000
1333  131 ALA  CA   -24.28607 -35.84094 102.98902 B1  49   0.00000
1334  131 ALA  CB   -23.06137 -35.44271 103.80801 B1  49   0.00000
1335  131 ALA  C    -23.85084 -36.20833 101.58658 B1  49   0.00000
1336  131 ALA  O    -23.17892 -37.20532 101.36065 B1  49   0.00000
1337  132 VAL  N    -24.28495 -35.36774 100.63154 B1  50   0.00000
1338  132 VAL  H    -24.78984 -34.54695 100.85567 B1  50   0.00000
1339  132 VAL  CA   -24.05930 -35.79619  99.24192 B1  50   0.00000
1340  132 VAL  CB   -25.12578 -35.11200  98.36560 B1  50   0.00000
```

FIG. 22

```
./DR1_MIN2.CRD        Thu Feb 25 14:58:48 1993      22

1341  132 VAL  CG1  -25.  05  -35.45687   96.87606 B1   50   0.00000
1342  132 VAL  CG2  -26.51048 -35.48893   98.85777 B1   50   0.00000
1343  132 VAL  C    -22.64446 -35.53393   98.73419 B1   50   0.00000
1344  132 VAL  O    -22.12598 -36.19257   97.84114 B1   50   0.00000
1345  133 THR  N    -22.01646 -34.53567   99.35299 B1   51   0.00000
1346  133 THR  H    -22.44036 -34.04272  100.11190 B1   51   0.00000
1347  133 THR  CA   -20.68297 -34.13851   98.91128 B1   51   0.00000
1348  133 THR  CB   -20.84979 -33.09962   97.76600 B1   51   0.00000
1349  133 THR  OG1  -19.58519 -32.56706   97.34397 B1   51   0.00000
1350  133 THR  HG1  -19.69018 -32.10136   96.50551 B1   51   0.00000
1351  133 THR  CG2  -21.81730 -31.96947   98.32788 B1   51   0.00000
1352  133 THR  C    -19.91735 -33.59750  100.10846 B1   51   0.00000
1353  133 THR  O    -20.48697 -33.30952  101.15881 B1   51   0.00000
1354  134 GLU  N    -18.60119 -33.44216   99.91793 B1   52   0.00000
1355  134 GLU  H    -18.20352 -33.65725   99.02398 B1   52   0.00000
1356  134 GLU  CA   -17.75238 -32.88738  100.97647 B1   52   0.00000
1357  134 GLU  CB   -16.30452 -32.81284  100.49482 B1   52   0.00000
1358  134 GLU  CG   -15.76229 -34.17073  100.03844 B1   52   0.00000
1359  134 GLU  CD   -14.31377 -34.04410   99.60488 B1   52   0.00000
1360  134 GLU  OE1  -13.54341 -34.96158   99.88007 B1   52   0.00000
1361  134 GLU  OE2  -13.96021 -33.03519   98.99487 B1   52   0.00000
1362  134 GLU  C    -18.18601 -31.51310  101.45728 B1   52   0.00000
1363  134 GLU  O    -17.97884 -31.11916  102.59352 B1   52   0.00000
1364  135 LEU  N    -18.87611 -30.80678  100.55812 B1   53   0.00000
1365  135 LEU  H    -18.92762 -31.13340   99.61398 B1   53   0.00000
1366  135 LEU  CA   -19.55727 -29.57029  100.96531 B1   53   0.00000
1367  135 LEU  CB   -20.25914 -29.06218   99.70959 B1   53   0.00000
1368  135 LEU  CG   -20.12211 -27.57937   99.30843 B1   53   0.00000
1369  135 LEU  CD1  -20.93390 -26.68772  100.32666 B1   53   0.00000
1370  135 LEU  CD2  -18.63204 -27.23870   99.36436 B1   53   0.00000
1371  135 LEU  C    -20.53099 -29.72915  102.11422 B1   53   0.00000
1372  135 LEU  O    -20.60025 -28.93514  103.04463 B1   53   0.00000
1373  136 GLY  N    -21.29082 -30.82221  102.02891 B1   54   0.00000
1374  136 GLY  H    -21.14062 -31.49656  101.30480 B1   54   0.00000
1375  136 GLY  CA   -22.25373 -31.10000  103.08935 B1   54   0.00000
1376  136 GLY  C    -21.66227 -31.85099  104.26834 B1   54   0.00000
1377  136 GLY  O    -22.17280 -31.82013  105.38053 B1   54   0.00000
1378  137 ARG  N    -20.54192 -32.53644  104.01306 B1   55   0.00000
1379  137 ARG  H    -20.17033 -32.57514  103.08296 B1   55   0.00000
1380  137 ARG  CA   -19.94165 -33.32437  105.09532 B1   55   0.00000
1381  137 ARG  CB   -18.67070 -34.02762  104.58318 B1   55   0.00000
1382  137 ARG  CG   -18.13008 -35.07893  105.55025 B1   55   0.00000
1383  137 ARG  CD   -19.16855 -36.15719  105.85371 B1   55   0.00000
1384  137 ARG  NE   -18.66781 -37.06640  106.87657 B1   55   0.00000
1385  137 ARG  HE   -17.93002 -36.71900  107.47204 B1   55   0.00000
1386  137 ARG  CZ   -19.21896 -38.26612  107.07086 B1   55   0.00000
1387  137 ARG  NH1  -18.67534 -39.07643  107.97489 B1   55   0.00000
1388  137 ARG  HH11 -19.03969 -39.99255  108.14749 B1   55   0.00000
1389  137 ARG  HH12 -17.88763 -38.75541  108.49972 B1   55   0.00000
1390  137 ARG  NH2  -20.29085 -38.64369  106.37214 B1   55   0.00000
1391  137 ARG  HH21 -20.72192 -39.53705  106.49834 B1   55   0.00000
1392  137 ARG  HH22 -20.68879 -38.01490  105.70437 B1   55   0.00000
1393  137 ARG  C    -19.76330 -32.65026  106.46929 B1   55   0.00000
1394  137 ARG  O    -20.33202 -33.13643  107.44172 B1   55   0.00000
1395  138 PRO  N    -19.03095 -31.51331  106.56277 B1   56   0.00000
1396  138 PRO  CD   -18.26903 -30.78028  105.55482 B1   56   0.00000
1397  138 PRO  CA   -19.92500 -30.86885  107.67839 B1   56   0.00000
1398  138 PRO  CB   -18.00966 -29.66775  107.61418 B1   56   0.00000
1399  138 PRO  CG   -17.22921 -30.01427  106.35388 B1   56   0.00000
1400  138 PRO  C    -20.24853 -30.39451  108.65452 B1   56   0.00000
1401  138 PRO  O    -20.38873 -30.20105  109.65243 B1   56   0.00000
1402  139 ASP  N    -21.22822 -30.19407  107.56513 B1   57   0.00000
1403  139 ASP  H    -21.12955 -30.45258  106.60295 B1   57   0.00000
1404  139 ASP  CA   -22.54445 -29.76374  108.02835 B1   57   0.00000
```

FIG. 23

```
/DR1_KDI2.CRD        Thu Feb 25 14:58:48 1993        23

1405  139 ASP  CB    -23.2     1 -29.22794 106.80729 B1   57   0.00000
1406  139 ASP  CG    -24.50040  -28.44150 107.23406 B1   57   0.00000
1407  139 ASP  OD1   -24.33925  -27.25955 107.53698 B1   57   0.00000
1408  139 ASP  OD2   -25.59590  -29.00937 107.24891 B1   57   0.00000
1409  139 ASP  C     -23.29009  -30.90651 108.70646 B1   57   0.00000
1410  139 ASP  O     -23.84428  -30.79944 109.79628 B1   57   0.00000
1411  140 ALA  N     -23.18867  -32.06950 108.04975 B1   58   0.00000
1412  140 ALA  H     -22.77745  -32.09325 107.13514 B1   58   0.00000
1413  140 ALA  CA    -23.64141  -33.29863 108.70194 B1   58   0.00000
1414  140 ALA  CB    -23.39932  -34.51285 107.80148 B1   58   0.00000
1415  140 ALA  C     -22.96994  -33.52591 110.04660 B1   58   0.00000
1416  140 ALA  O     -23.61501  -33.62460 111.08086 B1   58   0.00000
1417  141 GLU  N     -21.63141  -33.53710 110.01537 B1   59   0.00000
1418  141 GLU  H     -21.14260  -33.44422 109.14251 B1   59   0.00000
1419  141 GLU  CA    -20.88131  -33.73045 111.26272 B1   59   0.00000
1420  141 GLU  CB    -19.38545  -33.75474 110.92637 B1   59   0.00000
1421  141 GLU  CG    -19.08157  -34.92155 109.97183 B1   59   0.00000
1422  141 GLU  CD    -17.65605  -34.91070 109.44677 B1   59   0.00000
1423  141 GLU  OE1   -17.21662  -35.95752 108.96182 B1   59   0.00000
1424  141 GLU  OE2   -16.99658  -33.87375 109.50268 B1   59   0.00000
1425  141 GLU  C     -21.20315  -32.72395 112.36696 B1   59   0.00000
1426  141 GLU  O     -21.35204  -33.05368 113.53869 B1   59   0.00000
1427  142 TYR  N     -21.39109  -31.47026 111.93865 B1   60   0.00000
1428  142 TYR  H     -21.16858  -31.22939 110.99159 B1   60   0.00000
1429  142 TYR  CA    -21.91640  -30.42572 112.82625 B1   60   0.00000
1430  142 TYR  CB    -22.17510  -29.18770 111.95478 B1   60   0.00000
1431  142 TYR  CG    -22.15441  -27.86866 112.68902 B1   60   0.00000
1432  142 TYR  CD1   -20.91930  -27.21121 112.08286 B1   60   0.00000
1433  142 TYR  CE1   -20.89216  -25.94177 113.49633 B1   60   0.00000
1434  142 TYR  CD2   -23.36373  -27.27306 113.11310 B1   60   0.00000
1435  142 TYR  CE2   -23.33600  -26.00211 113.72688 B1   60   0.00000
1436  142 TYR  CZ    -22.10013  -25.34007 113.91274 B1   60   0.00000
1437  142 TYR  OH    -22.06472  -24.08718 114.49226 B1   60   0.00000
1438  142 TYR  HH    -22.95958  -23.75980 114.62492 B1   60   0.00000
1439  142 TYR  C     -23.20365  -30.84932 113.52485 B1   60   0.00000
1440  142 TYR  O     -23.33185  -30.86335 114.74427 B1   60   0.00000
1441  143 TRP  N     -24.16619  -31.24530 112.69102 B1   61   0.00000
1442  143 TRP  H     -24.01203  -31.27353 111.69669 B1   61   0.00000
1443  143 TRP  CA    -25.36084  -31.65772 113.24427 B1   61   0.00000
1444  143 TRP  CB    -26.46502  -31.82534 112.10045 B1   61   0.00000
1445  143 TRP  CG    -26.82927  -30.51319 111.43167 B1   61   0.00000
1446  143 TRP  CD2   -27.59514  -30.35383 110.26190 B1   61   0.00000
1447  143 TRP  CE2   -27.68725  -28.88192 110.01923 B1   61   0.00000
1448  143 TRP  CE3   -28.23171  -31.24445 109.37526 B1   61   0.00000
1449  143 TRP  CD1   -26.49404  -29.20408 111.84528 B1   61   0.00000
1450  143 TRP  NE1   -26.99373  -28.24161 111.01939 B1   61   0.00000
1451  143 TRP  HE1   -26.86335  -27.27405 111.09738 B1   61   0.00000
1452  143 TRP  CZ2   -28.41151  -28.41903 108.90296 B1   61   0.00000
1453  143 TRP  CZ3   -28.94655  -30.73482 108.27056 B1   61   0.00000
1454  143 TRP  CH2   -29.03488  -29.34388 108.03833 B1   61   0.00000
1455  143 TRP  C     -25.40824  -32.93379 114.07770 B1   61   0.00000
1456  143 TRP  O     -26.13451  -33.11650 115.04995 B1   61   0.00000
1457  144 ASN  N     -24.46546  -33.80055 113.69236 B1   62   0.00000
1458  144 ASN  H     -23.94027  -33.62305 112.85783 B1   62   0.00000
1459  144 ASN  CA    -24.16067  -34.99080 114.49069 B1   62   0.00000
1460  144 ASN  CB    -23.20850  -35.93308 113.73882 B1   62   0.00000
1461  144 ASN  CG    -23.69541  -36.68861 112.61740 B1   62   0.00000
1462  144 ASN  OD1   -23.68355  -36.47075 111.43371 B1   62   0.00000
1463  144 ASN  ND2   -24.72776  -37.64097 113.02365 B1   62   0.00000
1464  144 ASN  HD21  -24.69338  -37.81526 113.99276 B1   62   0.00000
1465  144 ASN  HD22  -25.19584  -38.20406 112.34455 B1   62   0.00000
1466  144 ASN  C     -23.49875  -34.69497 115.82591 B1   62   0.00000
1467  144 ASN  O     -23.43003  -35.54654 116.69924 B1   62   0.00000
1468  145 SER  N     -22.99694  -33.45640 115.97315 B1   63   0.00000
```

FIG. 24

```
./LR1_MIN2.CRD         Thu Feb 25 14:58:46 1993        24

1469  145 SER   H      -22.10    -32.80428 115.21961 B1   63    0.00000
1470  145 SER   CA     -22.35004 -33.14621 117.25865 B1   63    0.00000
1471  145 SER   CB     -20.91921 -32.73054 117.01176 B1   63    0.00000
1472  145 SER   OG     -20.38983 -32.64180 118.24511 B1   63    0.00000
1473  145 SER   HG     -20.76055 -32.22535 118.91065 B1   63    0.00000
1474  145 SER   C      -23.11027 -32.07614 118.06161 B1   63    0.00000
1475  145 SER   O      -22.67401 -31.68287 119.13941 B1   63    0.00000
1476  146 GLN   N      -24.22180 -31.59037 117.51252 B1   64    0.00000
1477  146 GLN   H      -24.58118 -31.94604 116.64774 B1   64    0.00000
1478  146 GLN   CA     -24.90025 -30.49286 118.19522 B1   64    0.00000
1479  146 GLN   CB     -24.86315 -29.29301 117.23892 B1   64    0.00000
1480  146 GLN   CG     -25.45855 -27.96945 117.72882 B1   64    0.00000
1481  146 GLN   CD     -26.89096 -27.81462 117.25234 B1   64    0.00000
1482  146 GLN   OE1    -27.00837 -27.53609 118.00911 B1   64    0.00000
1483  146 GLN   NE2    -27.06556 -27.97948 115.94329 B1   64    0.00000
1484  146 GLN   HE21   -26.30809 -28.20349 115.33276 B1   64    0.00000
1485  146 GLN   HE22   -27.98288 -27.88997 115.56134 B1   64    0.00000
1486  146 GLN   C      -26.29488 -30.93694 118.57642 B1   64    0.00000
1487  146 GLN   O      -27.21649 -30.91839 117.77294 B1   64    0.00000
1488  147 LYS   N      -26.36947 -31.44426 119.82371 B1   65    0.00000
1489  147 LYS   H      -25.65249 -31.20699 120.47663 B1   65    0.00000
1490  147 LYS   CA     -27.35463 -32.46614 120.21964 B1   65    0.00000
1491  147 LYS   CB     -28.27258 -32.00851 121.37895 B1   65    0.00000
1492  147 LYS   CG     -29.34716 -33.02726 121.84203 B1   65    0.00000
1493  147 LYS   CD     -28.88674 -34.49172 121.97244 B1   65    0.00000
1494  147 LYS   CE     -29.96618 -35.46785 121.47444 B1   65    0.00000
1495  147 LYS   NZ     -29.40221 -36.81034 121.26907 B1   65    0.00000
1496  147 LYS   HZ1    -30.04886 -37.42223 120.71767 B1   65    0.00000
1497  147 LYS   HZ2    -28.53282 -36.76558 120.68922 B1   65    0.00000
1498  147 LYS   HZ3    -29.15199 -37.28892 122.15073 B1   65    0.00000
1499  147 LYS   C      -28.12445 -33.12689 119.09340 B1   65    0.00000
1500  147 LYS   O      -29.30235 -32.90174 118.83863 B1   65    0.00000
1501  148 ASP   N      -27.34620 -34.00916 118.45822 B1   66    0.00000
1502  148 ASP   H      -26.39747 -34.14495 118.75300 B1   66    0.00000
1503  148 ASP   CA     -27.79510 -35.00236 117.48362 B1   66    0.00000
1504  148 ASP   CB     -27.88927 -36.37833 118.17059 B1   66    0.00000
1505  148 ASP   CG     -26.79528 -36.57930 119.21585 B1   66    0.00000
1506  148 ASP   OD1    -25.69280 -36.06325 119.05153 B1   66    0.00000
1507  148 ASP   OD2    -27.07650 -37.20742 120.23524 B1   66    0.00000
1508  148 ASP   C      -29.08887 -34.63043 116.79645 B1   66    0.00000
1509  148 ASP   O      -30.17136 -35.14808 117.04951 B1   66    0.00000
1510  149 LEU   N      -28.92399 -33.61840 115.93941 B1   67    0.00000
1511  149 LEU   H      -27.98965 -33.30969 115.73440 B1   67    0.00000
1512  149 LEU   CA     -30.07076 -32.84036 115.45008 B1   67    0.00000
1513  149 LEU   CB     -29.45399 -31.74267 114.57360 B1   67    0.00000
1514  149 LEU   CG     -30.29432 -30.58223 114.02475 B1   67    0.00000
1515  149 LEU   CD1    -30.85820 -30.92475 112.65290 B1   67    0.00000
1516  149 LEU   CD2    -31.34761 -30.09615 115.02072 B1   67    0.00000
1517  149 LEU   C      -31.17667 -33.69413 114.80952 B1   67    0.00000
1518  149 LEU   O      -32.36472 -33.37859 114.83807 B1   67    0.00000
1519  150 LEU   N      -30.73118 -34.86138 114.32363 B1   68    0.00000
1520  150 LEU   H      -29.75579 -34.94139 114.11621 B1   68    0.00000
1521  150 LEU   CA     -31.59762 -36.02822 114.12850 B1   68    0.00000
1522  150 LEU   CB     -30.74740 -37.29867 114.15286 B1   68    0.00000
1523  150 LEU   CG     -29.89363 -37.44772 112.89569 B1   68    0.00000
1524  150 LEU   CD1    -20.64060 -38.26626 113.18796 B1   68    0.00000
1525  150 LEU   CD2    -30.71709 -38.01712 111.73915 B1   68    0.00000
1526  150 LEU   C      -32.74973 -36.17247 115.10785 B1   68    0.00000
1527  150 LEU   O      -33.89001 -36.01901 114.70350 B1   68    0.00000
1528  151 GLU   N      -32.47441 -36.43576 116.39428 B1   69    0.00000
1529  151 GLU   H      -31.52943 -36.57286 116.72119 B1   69    0.00000
1530  151 GLU   CA     -33.61295 -36.59512 117.30950 B1   69    0.00000
1531  151 GLU   CB     -33.19465 -36.99331 118.72938 B1   69    0.00000
1532  151 GLU   CG     -32.69082 -38.41906 118.86324 B1   69    0.00000
```

FIG. 25

```
./DNA_KIN2.CRD         Thu F  25 14:58:48 1993      25

1533  151 GLU  CD    -31.15287  -38.44464  118.70497 B1    69    0.00000
1534  151 GLU  OE1   -30.71320  -30.33129  117.58148 B1    69    0.00000
1535  151 GLU  OE2   -30.51522  -38.56462  119.72459 B1    69    0.00000
1536  151 GLU  C     -34.55067  -35.41168  117.43857 B1    69    0.00000
1537  151 GLU  O     -35.75790  -35.57313  117.58647 B1    69    0.00000
1538  152 GLN  N     -33.98601  -34.19780  117.35586 B1    70    0.00000
1539  152 GLN  H     -33.00321  -34.10256  117.18602 B1    70    0.00000
1540  152 GLN  CA    -34.89656  -33.04752  117.40695 B1    70    0.00000
1541  152 GLN  CB    -34.15680  -31.71646  117.32018 B1    70    0.00000
1542  152 GLN  CG    -33.46159  -31.26900  118.60094 B1    70    0.00000
1543  152 GLN  CD    -33.23376  -29.77424  118.49387 B1    70    0.00000
1544  152 GLN  OE1   -32.13068  -29.27019  118.36008 B1    70    0.00000
1545  152 GLN  NE2   -34.34656  -29.04682  118.54731 B1    70    0.00000
1546  152 GLN  HE21  -35.24607  -29.46511  118.65663 B1    70    0.00000
1547  152 GLN  HE22  -34.28188  -28.05358  118.46911 B1    70    0.00000
1548  152 GLN  C     -35.89575  -33.04746  116.27182 B1    70    0.00000
1549  152 GLN  O     -37.09756  -32.85841  116.43607 B1    70    0.00000
1550  153 ARG  N     -35.34435  -33.30759  115.08552 B1    71    0.00000
1551  153 ARG  H     -34.35839  -33.48709  114.99299 B1    71    0.00000
1552  153 ARG  CA    -36.25853  -33.42129  115.95947 B1    71    0.00000
1553  153 ARG  CB    -35.46322  -33.43707  112.66564 B1    71    0.00000
1554  153 ARG  CG    -34.84280  -32.07791  112.35054 B1    71    0.00000
1555  153 ARG  CD    -33.88699  -32.22570  111.17839 B1    71    0.00000
1556  153 ARG  NE    -33.53171  -30.95306  110.55166 B1    71    0.00000
1557  153 ARG  HE    -33.79858  -30.09360  110.98860 B1    71    0.00000
1558  153 ARG  CZ    -33.01475  -31.01372  109.31716 B1    71    0.00000
1559  153 ARG  NH1   -32.97943  -29.92906  108.54980 B1    71    0.00000
1560  153 ARG  HH11  -32.81618  -30.04802  107.55422 B1    71    0.00000
1561  153 ARG  HH12  -33.14801  -29.01024  108.90136 B1    71    0.00000
1562  153 ARG  NH2   -32.57787  -32.17691  108.83735 B1    71    0.00000
1563  153 ARG  HH21  -32.40269  -32.29042  107.04355 B1    71    0.00000
1564  153 ARG  HH22  -32.45571  -32.97359  109.42307 B1    71    0.00000
1565  153 ARG  C     -37.16363  -34.62908  114.06526 B1    71    0.00000
1566  153 ARG  O     -38.37029  -34.50228  113.96948 B1    71    0.00000
1567  154 ARG  N     -36.57082  -35.79410  115.34589 B1    72    0.00000
1568  154 ARG  H     -35.57655  -35.03805  114.34685 B1    72    0.00000
1569  154 ARG  CA    -37.52441  -37.02834  114.59374 B1    72    0.00000
1570  154 ARG  CB    -36.30561  -38.11823  115.12926 B1    72    0.00000
1571  154 ARG  CG    -37.06240  -39.46786  115.22908 B1    72    0.00000
1572  154 ARG  CD    -36.14056  -40.61269  115.69023 B1    72    0.00000
1573  154 ARG  NE    -36.90866  -41.85162  115.80184 B1    72    0.00000
1574  154 ARG  HE    -37.59626  -42.01330  115.09038 B1    72    0.00000
1575  154 ARG  CZ    -36.70093  -42.71372  116.80504 B1    72    0.00000
1576  154 ARG  NH1   -37.45795  -43.80593  116.88687 B1    72    0.00000
1577  154 ARG  HH11  -37.33416  -44.47837  117.61567 B1    72    0.00000
1578  154 ARG  HH12  -38.17495  -43.96809  116.20728 B1    72    0.00000
1579  154 ARG  NH2   -35.75363  -42.48325  117.71513 B1    72    0.00000
1580  154 ARG  HH21  -35.59042  -43.10493  118.48012 B1    72    0.00000
1581  154 ARG  HH22  -35.18100  -41.66590  117.63709 B1    72    0.00000
1582  154 ARG  C     -38.52465  -36.86141  115.51516 B1    72    0.00000
1583  154 ARG  O     -39.58964  -37.43301  115.28503 B1    72    0.00000
1584  155 ARG  N     -38.35223  -36.06670  116.55472 B1    73    0.00000
1585  155 ARG  H     -37.44332  -35.69920  116.77047 B1    73    0.00000
1586  155 ARG  CA    -39.52250  -35.72569  117.36373 B1    73    0.00000
1587  155 ARG  CB    -39.05476  -34.79593  118.48265 B1    73    0.00000
1588  155 ARG  CG    -40.15723  -34.36970  119.44775 B1    73    0.00000
1589  155 ARG  CD    -39.62900  -33.36327  120.46128 B1    73    0.00000
1590  155 ARG  NE    -40.71623  -32.83780  121.26237 B1    73    0.00000
1591  155 ARG  HE    -41.63763  -33.18145  121.09517 B1    73    0.00000
1592  155 ARG  CZ    -40.47089  -31.92135  122.22743 B1    73    0.00000
1593  155 ARG  NH1   -41.46382  -31.43599  122.94081 B1    73    0.00000
1594  155 ARG  HH11  -41.33888  -30.75247  123.65592 B1    73    0.00000
1595  155 ARG  HH12  -42.41618  -31.75018  122.77039 B1    73    0.00000
1596  155 ARG  NH2   -39.22715  -31.49669  122.45304 B1    73    0.00000
```

```
/dr1_MIN2.CRD   Thu Feb 25  14:58:48 1993   26

1597  155 ARG   HH21  -39.02013  -30.51248  123.16141  B1  73  0.00000
1598  155 ARG   HH22  -39.47020  -31.56739  121.91409  B1  73  0.00000
1599  155 ARG   C     -40.65369  -35.07591  116.56312  B1  73  0.00000
1600  155 ARG   O     -41.90290  -35.51173  116.56406  B1  73  0.00000
1601  156 ALA   N     -40.28792  -34.01372  116.84196  B1  74  0.00000
1602  156 ALA   H     -39.31961  -33.76543  116.77165  B1  74  0.00000
1603  156 ALA   CA    -41.30773  -33.34226  115.03220  B1  74  0.00000
1604  156 ALA   CB    -40.72599  -32.10061  114.38248  B1  74  0.00000
1605  156 ALA   C     -41.91382  -34.25964  113.96113  B1  74  0.00000
1606  156 ALA   O     -43.11661  -34.40603  113.89911  B1  74  0.00000
1607  157 VAL   N     -40.99693  -34.92630  113.29026  B1  75  0.00000
1608  157 VAL   H     -40.04160  -34.56633  113.44809  B1  75  0.00000
1609  157 VAL   CA    -41.27013  -36.00533  112.34552  B1  75  0.00000
1610  157 VAL   CB    -39.86851  -36.59697  112.04096  B1  75  0.00000
1611  157 VAL   CG1   -39.79462  -38.01333  111.46596  B1  75  0.00000
1612  157 VAL   CG2   -39.10167  -35.63693  111.12688  B1  75  0.00000
1613  157 VAL   C     -42.31378  -37.01997  112.63333  B1  75  0.00000
1614  157 VAL   O     -43.41565  -37.10246  112.30297  B1  75  0.00000
1615  158 ASP   N     -41.96948  -37.78157  113.57061  B1  76  0.00000
1616  158 ASP   H     -41.06306  -37.68874  114.30470  B1  76  0.00000
1617  158 ASP   CA    -42.85516  -38.84272  114.32359  B1  76  0.00000
1618  158 ASP   CB    -42.05373  -39.82201  115.22733  B1  76  0.00000
1619  158 ASP   CG    -41.27306  -40.79302  114.39962  B1  76  0.00000
1620  158 ASP   OD1   -40.34839  -40.37634  113.70459  B1  76  0.00000
1621  158 ASP   OD2   -41.56922  -41.95359  114.41507  B1  76  0.00000
1622  158 ASP   C     -44.10643  -39.36706  115.04358  B1  76  0.00000
1623  158 ASP   O     -45.17033  -38.86720  114.93621  B1  76  0.00000
1624  159 THR   N     -43.96505  -37.26512  115.70661  B1  76  0.00000
1625  159 THR   H     -43.09027  -35.78113  116.56564  B1  77  0.00000
1626  159 THR   CA    -45.16504  -36.89791  116.56067  B1  77  0.00000
1627  159 THR   CB    -44.86368  -36.97162  118.07412  B1  77  0.00000
1628  159 THR   CG1   -46.06916  -37.10329  118.79712  B1  77  0.00000
1629  159 THR   HG1   -46.91547  -37.30091  119.72206  B1  77  0.00000
1630  159 THR   CG2   -44.03422  -35.82624  118.66004  B1  77  0.00000
1631  159 THR   C     -45.84449  -38.56150  116.12087  B1  77  0.00000
1632  159 THR   O     -47.06166  -38.51846  116.96765  B1  77  0.00000
1633  160 TYR   N     -45.05269  -34.84372  115.87045  B1  78  0.00000
1634  160 TYR   H     -44.06861  -34.64495  115.78633  B1  78  0.00000
1635  160 TYR   CA    -45.73499  -33.26691  115.64281  B1  78  0.00000
1636  160 TYR   CB    -44.74473  -32.10746  115.78676  B1  78  0.00000
1637  160 TYR   CG    -45.25402  -31.12355  116.81319  B1  78  0.00000
1638  160 TYR   CD1   -44.85214  -31.25680  118.16144  B1  78  0.00000
1639  160 TYR   CE1   -45.23319  -30.34310  119.12535  B1  78  0.00000
1640  160 TYR   CD2   -46.12744  -30.06443  116.42011  B1  78  0.00000
1641  160 TYR   CE2   -46.60347  -29.17117  117.38468  B1  78  0.00000
1642  160 TYR   CZ    -46.20160  -29.30406  118.73381  B1  78  0.00000
1643  160 TYR   OH    -46.56272  -28.41253  119.68223  B1  78  0.00000
1644  160 TYR   HH    -47.26242  -27.90044  119.27249  B1  78  0.00000
1645  160 TYR   C     -46.46006  -33.16254  114.31073  B1  78  0.00000
1646  160 TYR   O     -47.69067  -32.62968  114.21477  B1  78  0.00000
1647  161 CYS   N     -45.72696  -33.56692  113.36774  B1  79  0.00000
1648  161 CYS   H     -44.77082  -33.85206  113.40718  B1  79  0.00000
1649  161 CYS   CA    -46.32708  -33.68877  111.99544  B1  79  0.00000
1650  161 CYS   CB    -45.27134  -34.17403  110.93065  B1  79  0.00000
1651  161 CYS   SG    -45.67069  -35.63716  109.19024  B1  79  0.00000
1652  161 CYS   C     -47.53731  -34.60219  111.93094  B1  79  0.00000
1653  161 CYS   O     -48.56723  -34.29704  111.38273  B1  79  0.00000
1654  162 ARG   N     -47.37462  -35.72005  112.85663  B1  80  0.00000
1655  162 ARG   H     -46.47636  -35.94232  113.03662  B1  80  0.00000
1656  162 ARG   CA    -48.50678  -36.61784  112.89998  B1  80  0.00000
1657  162 ARG   CB    -48.07710  -37.71819  113.89476  B1  80  0.00000
1658  162 ARG   CG    -49.16345  -38.77197  114.12227  B1  80  0.00000
1659  162 ARG   CD    -48.67844  -40.04247  114.81823  B1  80  0.00000
1660  162 ARG   NE    -49.62321  -41.12379  114.54196  B1  80  0.00000
```

```
./CF_K2N2.CRD        Thu Feb 25 14:58:48 1993          27

1661  162 ARG  HE   -50.  94  -40.88455 114.11092 B1    80    0.00000
1662  162 ARG  CZ   -49.3,267  -42.40507 114.80601 B1    80    0.00000
1663  162 ARG  NH1  -50.23020 -43.32564 114.46730 B1    80    0.00000
1664  162 ARG  HH11 -50.11979 -44.31403 114.66150 B1    80    0.00000
1665  162 ARG  HH12 -51.06184 -43.06285 113.96028 B1    80    0.00000
1666  162 ARG  NH2  -48.19839 -42.76163 115.38323 B1    80    0.00000
1667  162 ARG  HH21 -48.00134 -43.72771 115.55650 B1    80    0.00000
1668  162 ARG  HH22 -47.52579 -42.06788 115.64161 B1    80    0.00000
1669  162 ARG  C    -49.75512 -35.92906 113.42487 B1    80    0.00000
1670  162 ARG  O    -50.02093 -35.93732 112.81658 B1    80    0.00000
1671  163 HIS  N    -49.58593 -35.31862 114.60088 B1    81    0.00000
1672  163 HIS  H    -48.68252 -35.28035 115.03933 B1    81    0.00000
1673  163 HIS  CA   -50.76431 -34.73357 115.23467 B1    81    0.00000
1674  163 HIS  CB   -50.42874 -34.29045 116.66134 B1    81    0.00000
1675  163 HIS  CG   -50.41026 -35.50649 117.55950 B1    81    0.00000
1676  163 HIS  ND1  -51.51644 -36.01842 118.12240 B1    81    0.00000
1677  163 HIS  HD1  -52.42830 -35.67431 118.03242 B1    81    0.00000
1678  163 HIS  CD2  -49.31404 -36.28837 117.93420 B1    81    0.00000
1679  163 HIS  NE2  -49.78030 -37.28089 118.73130 B1    81    0.00000
1680  163 HIS  CE1  -51.33423 -37.11585 118.64798 B1    81    0.00000
1681  163 HIS  C    -51.37160 -33.59588 114.44466 B1    81    0.00000
1682  163 HIS  O    -52.56947 -33.55956 114.18659 B1    81    0.00000
1683  164 ASN  N    -50.50246 -32.67616 114.01202 B1    82    0.00000
1684  164 ASN  H    -49.51981 -32.74462 114.21247 B1    82    0.00000
1685  164 ASN  CA   -51.04300 -31.58239 113.20331 B1    82    0.00000
1686  164 ASN  CB   -49.96583 -30.54361 112.89196 B1    82    0.00000
1687  164 ASN  CG   -49.91907 -29.53869 114.02377 B1    82    0.00000
1688  164 ASN  OD1  -49.23948 -29.62233 114.96163 B1    82    0.00000
1689  164 ASN  ND2  -50.00473 -28.55321 113.91309 B1    82    0.00000
1690  164 ASN  HD21 -51.44311 -28.49843 113.14586 B1    82    0.00000
1691  164 ASN  HD22 -50.84210 -27.84178 114.61251 B1    82    0.00000
1692  164 ASN  C    -51.70674 -32.02333 111.91584 B1    82    0.00000
1693  164 ASN  O    -52.73418 -31.48602 111.51085 B1    82    0.00000
1694  165 TYR  N    -51.12326 -33.05626 111.29191 B1    83    0.00000
1695  165 TYR  H    -50.28201 -33.49370 111.62194 B1    83    0.00000
1696  165 TYR  CA   -51.81304 -33.54191 110.10401 B1    83    0.00000
1697  165 TYR  CB   -50.52781 -34.67239 109.25048 B1    83    0.00000
1698  165 TYR  CG   -51.39689 -34.50284 107.80317 B1    83    0.00000
1699  165 TYR  CD1  -52.18946 -33.44669 107.29137 B1    83    0.00000
1700  165 TYR  CE1  -52.63312 -33.47413 105.96126 B1    83    0.00000
1701  165 TYR  CD2  -51.04289 -35.58963 106.96903 B1    83    0.00000
1702  165 TYR  CE2  -51.48846 -35.61522 105.62740 B1    83    0.00000
1703  165 TYR  CZ   -52.28557 -34.55457 105.13440 B1    83    0.00000
1704  165 TYR  OH   -52.75931 -34.53152 103.84155 B1    83    0.00000
1705  165 TYR  HH   -52.13515 -34.97162 103.24416 B1    83    0.00000
1706  165 TYR  C    -53.16114 -34.17050 110.39688 B1    83    0.00000
1707  165 TYR  O    -54.17243 -33.75040 109.85354 B1    83    0.00000
1708  166 GLY  N    -53.16827 -35.13255 111.32677 B1    84    0.00000
1709  166 GLY  H    -52.30920 -35.44284 111.74443 B1    84    0.00000
1710  166 GLY  CA   -54.44388 -35.75931 111.69489 B1    84    0.00000
1711  166 GLY  C    -55.55421 -34.78683 112.08191 B1    84    0.00000
1712  166 GLY  O    -56.70058 -34.86763 111.64884 B1    84    0.00000
1713  167 VAL  N    -55.16433 -33.81049 112.90998 B1    85    0.00000
1714  167 VAL  H    -54.21931 -33.77699 113.25020 B1    85    0.00000
1715  167 VAL  CA   -56.14083 -32.77588 113.26808 B1    85    0.00000
1716  167 VAL  CB   -55.54422 -31.87200 114.36486 B1    85    0.00000
1717  167 VAL  CG1  -56.46931 -30.71890 114.75691 B1    85    0.00000
1718  167 VAL  CG2  -55.22649 -32.70528 115.60849 B1    85    0.00000
1719  167 VAL  C    -56.62003 -31.96437 112.06515 B1    85    0.00000
1720  167 VAL  O    -57.80658 -31.70971 111.87375 B1    85    0.00000
1721  168 GLY  N    -55.65605 -31.61592 111.20320 B1    86    0.00000
1722  168 GLY  H    -54.68827 -31.81924 111.38362 B1    86    0.00000
1723  168 GLY  CA   -56.04215 -30.94450 109.94972 B1    86    0.00000
1724  168 GLY  C    -57.02336 -31.77629 109.11507 B1    86    0.00000
```

FIG. 28

```
./DRL_MIN2.CRD         Thu Feb 25 14:58:46 1993         28

1725  168 GLY        -58.    49 -31.28044 108.61617 B1   86   0.00000
  1726  169 GLU   N    -56.74134 -33.07169 109.00665 B1   87   0.00000
  1727  169 GLU   H    -55.87921 -33.43085 109.43169 B1   87   0.00000
  1728  169 GLU   CA   -57.59179 -34.00467 108.30469 B1   87   0.00000
  1729  169 GLU   CB   -56.95070 -35.39155 108.28846 B1   87   0.00000
  1730  169 GLU   CG   -55.67851 -35.40281 107.43481 B1   87   0.00000
  1731  169 GLU   CD   -54.91259 -36.69049 107.65905 B1   87   0.00000
  1732  169 GLU   OE1  -53.74095 -36.61342 108.02205 B1   87   0.00000
  1733  169 GLU   OE2  -55.48540 -37.76250 107.47736 B1   87   0.00000
  1734  169 GLU   C    -59.00151 -34.05273 108.86565 B1   87   0.00000
  1735  169 GLU   O    -59.98966 -34.06690 108.14126 B1   87   0.00000
  1736  170 SER   N    -59.06996 -33.99305 110.19884 B1   88   0.00000
  1737  170 SER   H    -58.23138 -34.05998 110.74831 B1   88   0.00000
  1738  170 SER   CA   -60.38255 -33.85094 110.83391 B1   88   0.00000
  1739  170 SER   CB   -60.18950 -33.85581 112.35798 B1   88   0.00000
  1740  170 SER   OG   -61.42043 -34.13237 113.03659 B1   88   0.00000
  1741  170 SER   HG   -61.30877 -34.00943 113.98374 B1   88   0.00000
  1742  170 SER   C    -61.16415 -32.61665 110.37646 B1   88   0.00000
  1743  170 SER   O    -62.31497 -32.69150 109.96191 B1   88   0.00000
  1744  171 PHE   N    -60.49231 -31.45621 110.41676 B1   89   0.00000
  1745  171 PHE   H    -59.54601 -31.41832 110.75393 B1   89   0.00000
  1746  171 PHE   CA   -61.19539 -30.24631 109.95663 B1   89   0.00000
  1747  171 PHE   CB   -60.30793 -28.99941 110.10880 B1   89   0.00000
  1748  171 PHE   CG   -59.94208 -28.68147 111.54294 B1   89   0.00000
  1749  171 PHE   CD1  -58.59291 -28.39703 211.85413 B1   89   0.00000
  1750  171 PHE   CD2  -60.93098 -28.63398 112.55491 B1   89   0.00000
  1751  171 PHE   CE1  -58.23032 -28.06074 113.17656 B1   89   0.00000
  1752  171 PHE   CE2  -60.56845 -28.29967 113.87858 B1   89   0.00000
  1753  171 PHE   CZ   -59.21901 -28.01319 114.18527 B1   89   0.00000
  1754  171 PHE   C    -61.62802 -30.29139 108.49502 B1   89   0.00000
  1755  171 PHE   O    -62.68697 -29.84047 108.07691 B1   89   0.00000
  1756  172 THR   N    -60.72520 -30.85206 107.69903 B1   90   0.00000
  1757  172 THR   H    -59.91792 -31.29854 108.09636 B1   90   0.00000
  1758  172 THR   CA   -60.04308 -30.66246 106.25599 B1   90   0.00000
  1759  172 THR   CB   -59.41710 -30.70747 105.70165 B1   90   0.00000
  1760  172 THR   OG1  -59.35292 -30.21143 104.36207 B1   90   0.00000
  1761  172 THR   HG1  -60.15430 -30.48800 103.89285 B1   90   0.00000
  1762  172 THR   CG2  -58.90262 -32.13906 105.74825 B1   90   0.00000
  1763  172 THR   C    -61.71208 -31.64677 105.47987 B1   90   0.00000
  1764  172 THR   O    -61.76078 -31.56505 104.25169 B1   90   0.00000
  1765  173 VAL   N    -62.32957 -32.60764 106.19315 B1   91   0.00000
  1766  173 VAL   H    -62.28706 -32.56397 107.19363 B1   91   0.00000
  1767  173 VAL   CA   -62.87984 -33.81113 105.53718 B1   91   0.00000
  1768  173 VAL   CB   -63.87967 -34.51911 106.47899 B1   91   0.00000
  1769  173 VAL   CG1  -64.50006 -35.77324 105.85034 B1   91   0.00000
  1770  173 VAL   CG2  -63.20452 -34.90248 107.79466 B1   91   0.00000
  1771  173 VAL   C    -63.53710 -33.59419 104.16716 B1   91   0.00000
  1772  173 VAL   O    -63.18750 -34.24452 103.18126 B1   91   0.00000
  1773  174 GLN   N    -64.41211 -32.59570 104.14711 B1   92   0.00000
  1774  174 GLN   H    -64.59818 -32.11269 105.00138 B1   92   0.00000
  1775  174 GLN   CA   -65.14373 -32.19104 102.94243 B1   92   0.00000
  1776  174 GLN   CB   -65.76132 -30.80951 103.22574 B1   92   0.00000
  1777  174 GLN   CG   -66.77986 -30.26016 102.21318 B1   92   0.00000
  1778  174 GLN   CD   -66.09397 -29.58024 101.04012 B1   92   0.00000
  1779  174 GLN   OE1  -65.45924 -28.54065 101.15380 B1   92   0.00000
  1780  174 GLN   NE2  -66.26402 -30.18961  99.87453 B1   92   0.00000
  1781  174 GLN   HE21 -66.63226 -31.11966  99.82928 B1   92   0.00000
  1782  174 GLN   HE22 -65.97833 -29.74839  99.02730 B1   92   0.00000
  1783  174 GLN   C    -64.36067 -32.18074 101.63553 B1   92   0.00000
  1784  174 GLN   O    -64.88562 -32.51356 100.57991 B1   92   0.00000
  1785  175 ARG   N    -63.09233 -31.77447 101.73327 B1   93   0.00000
  1786  175 ARG   H    -62.69754 -31.53564 102.62225 B1   93   0.00000
  1787  175 ARG   CA   -62.31707 -31.78635 100.50018 B1   93   0.00000
  1788  175 ARG   CB   -61.85817 -30.36631 100.16956 B1   93   0.00000
```

FIG. 29

```
DR1_KIN2.CRD        Thu Feb 25 14:58:48 1993      29

1789  175 ARG  CG    -61.24395 -30.26914  90.77310 B1  93  0.00000
1790  175 ARG  CD    -60.91597 -28.04209  96.34709 B1  93  0.00000
1791  175 ARG  NE    -59.98117 -28.87216  97.22615 B1  93  0.00000
1792  175 ARG  HE    -59.59146 -29.76910  97.00518 B1  93  0.00000
1793  175 ARG  CZ    -59.49795 -27.74924  96.68186 B1  93  0.00000
1794  175 ARG  NH1   -58.57343 -27.83579  95.72833 B1  93  0.00000
1795  175 ARG  HH11  -58.19414 -27.02728  95.28229 B1  93  0.00000
1796  175 ARG  HH12  -58.22480 -28.73459  95.46034 B1  93  0.00000
1797  175 ARG  NH2   -59.92427 -26.55682  97.09593 B1  93  0.00000
1798  175 ARG  HH21  -59.57028 -25.70796  96.70808 B1  93  0.00000
1799  175 ARG  HH22  -60.60311 -26.50975  97.82696 B1  93  0.00000
1800  175 ARG  C     -61.17336 -32.79150 100.46150 B1  93  0.00000
1801  175 ARG  O     -61.02327 -33.52738  99.49809 B1  93  0.00000
1802  176 ARG  N     -60.36493 -32.85103 101.53216 B1  94  0.00000
1803  176 ARG  H     -60.53761 -32.31340 102.35662 B1  94  0.00000
1804  176 ARG  CA    -59.25084 -33.80802 101.41499 B1  94  0.00000
1805  176 ARG  CB    -58.18750 -33.62483 102.49829 B1  94  0.00000
1806  176 ARG  CG    -57.32871 -32.37173 102.34974 B1  94  0.00000
1807  176 ARG  CD    -56.27515 -32.28237 103.45854 B1  94  0.00000
1808  176 ARG  NE    -56.30062 -30.94018 104.04511 B1  94  0.00000
1809  176 ARG  HE    -56.83150 -30.25818 103.53710 B1  94  0.00000
1810  176 ARG  CZ    -55.69078 -30.63659 105.15759 B1  94  0.00000
1811  176 ARG  NH1   -55.74431 -29.38340 105.64628 B1  94  0.00000
1812  176 ARG  HH11  -55.30471 -29.10555 106.50132 B1  94  0.00000
1813  176 ARG  HH12  -56.24088 -28.69008 105.12278 B1  94  0.00000
1814  176 ARG  NH2   -55.05038 -31.57276 105.85297 B1  94  0.00000
1815  176 ARG  HH21  -54.58912 -31.37726 106.75753 B1  94  0.00000
1816  176 ARG  HH22  -55.02183 -32.51329 105.54660 B1  94  0.00000
1817  176 ARG  C     -59.64666 -35.27348 101.42902 B1  94  0.00000
1818  176 ARG  O     -58.87808 -36.15316 101.06767 B1  94  0.00000
1819  177 VAL  N     -60.88626 -35.53350 101.85272 B1  95  0.00000
1820  177 VAL  H     -61.51901 -34.82551 102.18430 B1  95  0.00000
1821  177 VAL  CA    -61.32863 -36.91608 101.70299 B1  95  0.00000
1822  177 VAL  CB    -61.79519 -37.47193 103.06780 B1  95  0.00000
1823  177 VAL  CG1   -61.64113 -39.00335 103.05589 B1  95  0.00000
1824  177 VAL  CG2   -60.88761 -37.00753 104.21299 B1  95  0.00000
1825  177 VAL  C     -62.41412 -37.02458 100.63553 B1  95  0.00000
1826  177 VAL  O     -63.44404 -37.67295 100.79118 B1  95  0.00000
1827  178 HIS  N     -62.14889 -36.33028  99.52296 B1  96  0.00000
1828  178 HIS  H     -61.32158 -35.77698  99.39184 B1  96  0.00000
1829  178 HIS  CA    -63.09845 -36.32813  98.41659 B1  96  0.00000
1830  178 HIS  CB    -64.01495 -35.10064  98.57314 B1  96  0.00000
1831  178 HIS  CG    -65.27852 -35.21481  97.74669 B1  96  0.00000
1832  178 HIS  ND1   -65.30573 -35.62002  96.46944 B1  96  0.00000
1833  178 HIS  HD1   -64.50806 -35.91855  95.96816 B1  96  0.00000
1834  178 HIS  CD2   -66.58524 -34.92566  98.14872 B1  96  0.00000
1835  178 HIS  NE2   -67.39749 -35.16505  97.08780 B1  96  0.00000
1836  178 HIS  CE1   -66.60728 -35.59364  96.05191 B1  96  0.00000
1837  178 HIS  C     -62.34621 -36.29235  97.09131 B1  96  0.00000
1838  178 HIS  OCT1  -61.22615 -35.78756  97.07091 B1  96  0.00000
1839  178 HIS  OCT2  -62.87363 -36.77415  96.08709 B1  96  0.00000
```

FIG. 30

MODEL FOR TESTING IMMUNOGENICITY OF PEPTIDES

CROSS REFERENCE

This application is a Continuation-In-Part of Ser. No. 08/798,734 filed Jan. 27, 1997, now U.S. Pat. No. 6,309,669, which is a Continuation-In-Part of Ser. No. 08/590,973, now abandoned, which is a Continuation-In-Part of Ser. No. 08/247,884, filed May 23, 1994, now abandoned, which is a Continuation-In-Part of Ser. No. 08/064,559 filed May 21, 1993, now abandoned.

GOVERNMENT INTEREST

The invention described herein may be manufactured, licensed and used by or for governmental purposes without the payment of any royalties to us thereon.

FIELD OF THE INVENTION

This invention relates to a means of predicting potential of a peptide for eliciting immune response.

BACKGROUND OF THE INVENTION

Among the numerous steps required for an immunological response to occur is the presentation of the antigen by macrophages to the B-cell or T-cell. This presentation is mediated by the Class I and Class II major histocompatibility complex (MHC) molecules on the surface of the cell. The MHC molecules hold antigens in the form of the peptide fragments and together with the receptor molecule on the T-cells, form a macromolecular complex that induces a response in the T-cell. Therefore, a necessary step in an immune response is the binding of the antigen to the MHC.

Recent single crystal X-ray structures of human and murine Class I MHC's have been reported. Analysis of these crystal structures have shown that antigenic peptides lie in the so-called binding cleft for presentation to the T-cell. This cleft is formed by $\alpha_1$ and $\alpha_2$ domains and by β-strands from each domain forming the floor. Furthermore, the sequence polymorphism among Class I molecules can result in alterations of the surface of the cleft forming different pockets. Peptide side chains may insert into these pockets. Thus, different pockets may interact with different side chains. This implies the mechanism for the peptide specificity of class I MHC's. Peptides bound to the Class I MHC's in the crystal structures were found to have both the amino and carboxy termini tightly held by the MHC. There were few interactions near the middle of the cleft. Hence the bound peptide is allowed to bend slightly in the center. The observed binding mode helped to explain the apparent partial specificity of peptide sequence and the allowed variation in peptide length found among peptides isolated from Class I MHC's.

The precise mode of binding of peptides to Class II MHC molecules is less clear. While a single crystal X-ray diffraction structure for the HLA-DR1 MHC has been shown, the coordinates have remained unavailable. However, currently available theoretical and experimental results help form a hypothesis that the binding of a peptide to Class II MHC is similar to that observed with Class I. First, it is noted that the Class II binding cleft is structurally similar to that of Class I. This was concluded based upon a sequence analysis of 26 Class I and 54 Class II amino acid sequences.

Unlike with Class I molecules, self-peptides isolated from murine I-$A^b$ and I-$E^b$, from murine I-$A^d$ and from human HLA-DR1 molecules were found to be varied in size (13 to 25 residues long). The peptides isolated from the murine I-$A^b$ and I-$E^b$ molecules had heterogenous carboxy termini while those from I-$A^d$ and HLA-DR1 had ragged termini at both ends. The varying lengths indicate that the amino and carboxy termini of the peptides were not critical for the binding. One or both termini may protrude from the binding site and be available for further processing. The residues critical for binding were proposed to be at the ends of the peptide as opposed to the center.

SUMMARY OF THE INVENTION

It is the purpose of this invention to provide a method for preliminary screening of peptides for ability to elicit an immune response. Structural homology techniques were used to model a receptor (the Class II MHC is exemplified). This model makes it possible to preliminarily screen peptides for antigenic properties. By modifying the peptide to "fit" into the receptor it is possible to identify methods of rendering non-immunogenic peptides immunogenic.

The preliminary screening of peptides for immunogenicity comprises the steps of (1) creating a molecular model of a receptor followed by minimizing the model created, 2) modeling a peptide to be tested and minimizing the model of the peptide, then testing the fit of the model of the peptide into the model of the receptor to produce a composite minimized receptor/minimized peptide model. Upon finding an acceptable fit, the peptide may then be screened by a binding assay for actual binding to Class II MHC as a further test for immunogenicity.

It has been found that when the model of the peptide can not be fitted into the model of the receptor, the peptide will lack immunogenicity. While not all peptide models which can be made to "fit" into the model of the receptor will be effective as immunogens, the screening methods of the invention may make it possible to avoid undue biological testing of inappropriate peptides. By using the model, it is also possible to alter peptides to accommodate the receptor. Hence, the invention has both predictive and drug design applications.

BRIEF DESCRIPTION OF THE FIGURES

FIG. 1 shows the HLA-aw68 $\alpha_1$ and $\alpha_2$ domains with DR1 $\alpha_1$ and $\beta_1$ domains aw68 $\alpha_1$, and $\alpha_2$ domains are represented by SEQ ID NO:13, DR1 $\alpha$, and $\beta_2$ domains are represented by SEQ ID NO:14 and SEQ ID NO:15 respectively, FIGS. 2–30 are a printout of the minimized coordinates of the receptor;

DETAILED DESCRIPTION OF THE INVENTION

Figure 31:
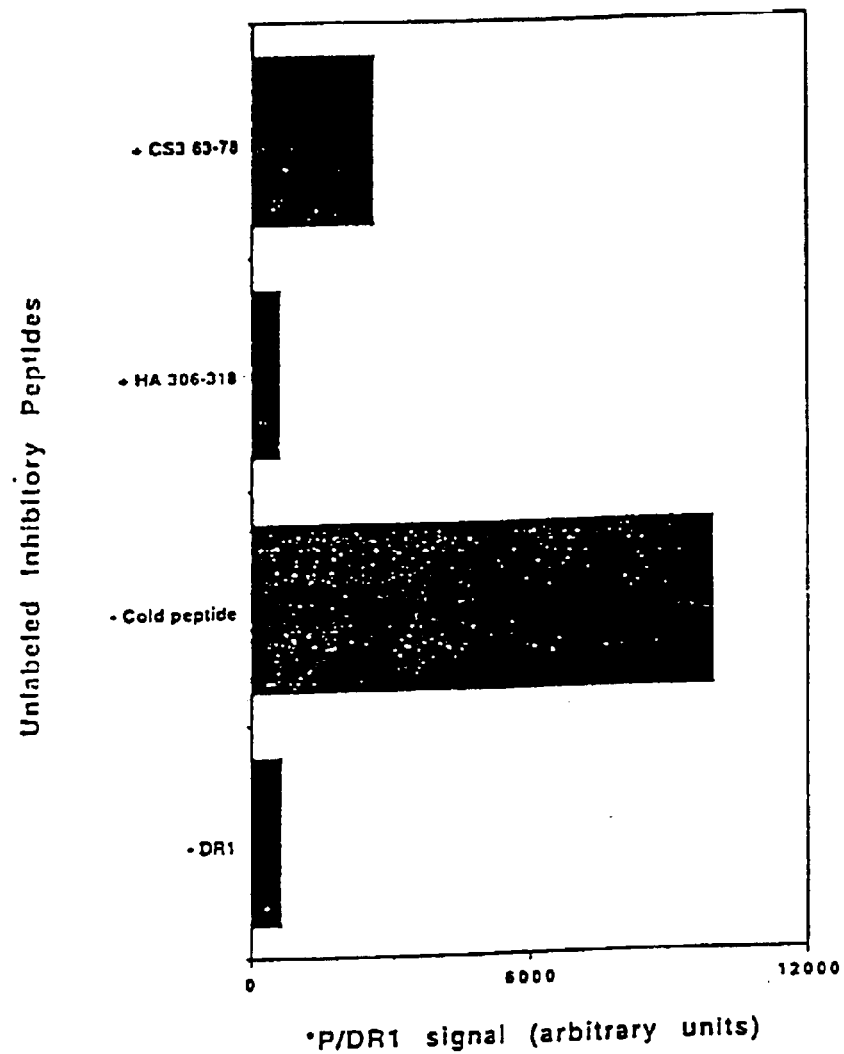
FIGS. 31 and 32 shows the effects of various peptides inhibiting the binding of labeled hemagglutinin in a competitive binding assay.
Figure 32:
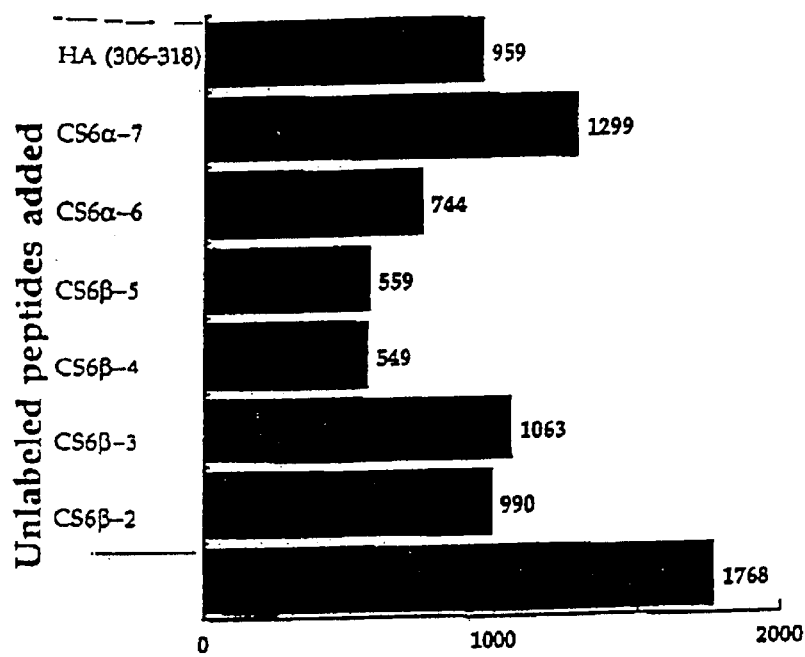

In order to understand and better predict peptide interaction with Class II MHC's and as an aid for synthetic peptide vaccine design, a structural homology model of HLA-DR1 molecule was made using the Class 1 HLA-aw68 as a reference molecule. For purposes of this analysis, numerous conserved residues were aligned leading to a proposed three-dimensional model for the Class II structure very similar to that of Class I. This model retained the overall conformation of a Class I MHC and agreed with a considerable amount of the published data. Furthermore, peptides shown to bind to DR1 were docked in the binding cleft of the model and analyzed. The results agree with the experimental binding data presented here. Hence, it is shown that the structural homology model reported here is useful for screening Class II MHC functionality.

It had been hypothesized that few peptide residues may be required for binding to DR1. By substituting residues into the influenza hemagglutinin 307–319 T-cell epitope (HA) it had been determined that a single tyrosine at 308 was required for binding. A synthetic peptide with the tyrosine at position 308 and a lysine at 315 was found to bind DR1 as well as the native peptide. Hence, it was concluded that few peptide residues determine the high affinity binding to DR1.

The peptides produced according to the present invention may be used alone or chemically bound to another peptide and/or carrier in order to elicit an immune response. An immune response is elicited by administering a peptide to an animal in an effective dose and by an effective route of administration. Typically the peptide will be administered with an immunologically acceptable carrier. The routes of administration, dosages, times between multiple administrations will be based on the particular peptide and are standard operations of those skilled in the art.

Of particular interest are peptides from pathogenic microorganisms and neoplasms. In such an example, a vaccine may be formed with the peptide and any known immunological carrier and may be administered prophylactically or therapeutically. The immune response may be elicited for a number of reasons other than for prophylaxis or therapy such as increasing antibody production from the harvesting of antibodies, or increasing specific B-cell or T-cell concentration for the production of hybridomas or cellular therapy.

The choice of host animals is limited only to those capable of an immune response. Preferred hosts are mammals, more preferred are humans.

The vaccine may contain plural peptides with each peptide corresponding to the same or different antigens. The peptides may be used unbound or they may be chemically bound to another peptide or an unrelated protein or other molecule. A preferred vaccine preparation contains a plurality of peptides chemically bound to a larger more immunogenic peptide.

The peptide or plurality of peptides may be adsorbed, bound or encapsulated in a biodegradable microsphere, microcapsule, larger carrier or a combination of these. The carrier may have a slow or controlled release property thereby releasing the peptide under appropriate conditions and times for enhanced immunization. This is particularly important when administering the peptide orally where stomach acid can degrade the peptide.

When the peptide is combined (i.e. encapsulated within) with a biodegradable lactide and/or glycolide polymers, they can be formulated into immunostimulating composition comprising encapsulating-microspheres, which may contain a pharmaceutically-acceptable adjuvant, wherein said microspheres having a diameter between 1 nanogram (ng) to 10 microns (um) are comprised of (a) a biodegradable-biocompatible poly (DL-lactide-co-glycolide) as the bulk matrix, wherein the relative ratio between the amount of lactide and glycolide components are within the range of 40:60 to 0:100 and (b) an immunogenic substance comprising Colony Factor Antigen (CFA/II), hepatitis B surface antigen (HBsAg), or a physiologically similar antigen that serves to elicit the production of antibodies in animal subjects. Compositions wherein the immunogenic substance is a peptide within the range of 0.1 to 1.5% based on the volume of the bulk matrix of lactide and glycolide component having a relative ratio of 48:52 to 58:42 should be especially useful.

Another embodiment of the present invention is to modify the amino acid sequence of a peptide to enhance its immunogenicity. This is done by modifying the natural peptide sequence to bind to the Class II MHC receptor DR12 with superior binding affinity for a Class II MHC receptor DR1 than the natural peptide sequence. This modified peptide is considered a synthetic peptide. Alternatively, the sequence may be modified to have a greater inhibition of HA (306–318) binding to a Class II MHC receptor DR1.

Many amino acid changes are acceptable in the formation of a synthetic peptide. The changes may be for similar types of amino acids such as leucine for isoleucine or they may be for diverse types such as tyrosine for lysine.

Materials and Methods:

The structural homology model for the DR1 Class II MHC was constructed using the QUANTA molecular modeling package (vision 3.2, Molecular Simulations, Inc., Burlington, Mass.) with the CHARMM and Protein Design modules. After alignment of the sequences as described below, gaps and loops were energy minimized using 100 steps of steepest descents minimization followed by 100 steps of adopted basis set Newton-Rapheson (ABNR) minimization. Large gaps were closed using a fragment database from a selected set of high-resolution crystal structures. The resulting structure we minimized in vacuo using 1000 steps of steepest descents followed by an additional 1000 steps of ABNR minimization. A distance related electrostatic function was used in all calculations with a dielectric constant of 1.0. Non-bound parameter lists were updated every 20 steps with a cutoff distance of 15.OA. Non-bonded calculations were performed using a shifted potential function between 11.OA and 14.OA. An extended atom set was used with only polar hydrogen atoms specifically placed. There were no explicit hydrogen bond energy calculations performed.

All peptides were initially modeled using QUANTA in an extended chain conformation and subjected to 500 steps of ABNR minimization. The resulting structures remained essentially in extended chain conformations. Individual peptides were manually docked in several different orientations into the binding cleft region of the minimized DR1 structure. The resulting bimolecular complex was subjected to 5000 steps of steepest descents minimization with non-bonded interactions updated every five steps. After minimization, bound peptides remained essentially in extended chain conformations. The lowest energy complexes for each peptide were selected for further analysis.

The selected peptide and DR1 complexes and the minimized DR1 model were subjected to the following molecular dynamics regimen: 300 steps of heating to 300° K, 600 steps of equilibration at 300° K, and 1100 steps of production dynamics. During this simulation, the DR1 C$\alpha$ atoms were constrained in their starting positions. All non-bonded interaction parameters were as stated for the minimization procedure. The lowest energy structure during the course of the production dynamics was selected and subjected to the 5000 step minimization procedure described previously with the C$\alpha$ restraints removed. The resulting structures were used for the binding energy calculations and for hydrogen bonding analysis.

Hydrogen bonds were determined using the QUANTA default parameters. Maximum allowed distances were 2.5 Å between a hydrogen and the acceptor atom and 3.3 Å between the donor and acceptor atoms. The minimum angle allowed between any set of atoms forming a hydrogen bond was 90°.

Competitive Inhibition Binding Assay:

HA peptide (the influenza hemagglutinin 307–319 T-cell epitope) was labeled with $^{125}$I. The labeled HA peptides were then allowed to interact with purified DR1 molecules during incubation to allow formation of peptide/DR1 complexes. After incubation, the peptide/DR1 composition was exposed to a native gel for chromatographic separation or passed through a spun column to separate labeled peptide/DR1 complex and free labelled peptide. When unlabeled peptides were added before incubation of labeled HA peptides and DR1, and if the unlabelled peptides had capacity for binding to DR1 simultaneous with $^{125}$I-HA, there was a resultant decrease in radioactive signal associated with the DR1. The extent of this decrease directly related to the binding capacity of the unlabeled unknown peptide.

Structural Homology Model for the DR1 Molecule:

The structural homology model was created, the reference molecule being the crystal structure of HLA-aw68. The HLA-aw68 coordinates and subsequent sequence were obtained from the entry 2HLA in the Brookhaven Protein Data Bank released Jan. 15, 1991, which is incorporated herein by reference. The sequence for the DR1 molecule was for the $\alpha_1$ domain was reported by Klein and for the $\beta_1$ domain, the study reported by Todd et al. (*Nature* 329, 599 (1987)).

The sequence alignment is based on Brown et al. (*Nature* 332, 845 (1988)). The complete alignment and numbering scheme for both are seen in FIG. 1. The Class II, $\beta_1$ and Class I $\alpha_2$ domains regions were conserved with some variations at the ends where the it two MHC's have different loop regions. The fourth B-strand in the $\alpha_1$ domain of HLA-aw68 (residues 30–38) is disrupted in the DR1 model. Only three residues are in a β-sheet conformation, probably due to the inserted glycine at position 28 before the strand and the large deletion in the loop region immediately after the strand. The two alpha-helical regions are clearly maintained. Both helices have been observed to be discontinuous in the Class I molecules and are similar in the DR1 model. The $\alpha_1$ domain helix is long and curves from residues 49α to 76α a without significant disruption. It is essentially a single continuous helix. However, the $\alpha_2$ helical region is broken into two separate helices as with the Class I molecules. A short helix (52–63) is separated from a longer helix (68–94) by a deformed region without secondary structure. This deformation is more pronounced in the DR1 model as opposed to the Class I molecules due to an insertion.

Influenza Hemagglutinin Peptide with DR1:

The amino acid residues 307–319 of influenza hemagglutinin (Pro-Lys-Tyr-Val-Lys-Gln-Asn-Thr-Leu-Lys-Leu-Ala-Thr, SEQ ID NO:1) make up a well-documented linear T-cell epitope which as been shown to be HLA-DR1 restricted. With the demonstration that the influenza hemagglutinin epitope (referred to as the HA peptide) binds DR1, it was chosen to be modeled into the binding cleft.

The peptide was initially inserted into the cleft so that Leu 11 HA was in the vicinity of the hydrophobic pocket. This allowed Asn 7 to be near the middle charged and polar groups of the cleft. The remaining residue of the motif (Lys 2) was near the vicinity of the remaining charged and polar residues at the end of the cleft. The only adjustment to the starting conformation was a slight rearrangement of the terminal peptide proline and Tyr 3 to alleviate obvious bad contacts.

After the energy minimization of the bimolecular complex, the total energy was reduced to 483 kcal/mol. This reduction in energy was accomplished by alleviation of several bad contacts and also by formation of several hydrogen bonds. The sticking feature of this mode is lack of hydrogen bonds in the carboxy terminal half of the peptide. Only one hydrogen bond is identified between the backbone carbonyl group of Leu 9 and the side chain of the $\beta_1$ Asn 77. In contrast, the amino terminal half has eleven identified interactions. Four of these interaction involve the peptide backbone residues Tyr 3, Val 4, and Gln 6. The remainder involve the side chains of Lys 2, Tyr 3, Lys 5 and Gln 6. Interestingly, Lys 5 is involved in more interactions (three) than Lys 2 (only 2). No interactions were observed as anticipated with Asn 7. Instead it was the glutamine at position 6 donating a hydrogen bond to the $\alpha_1$ Asn 62. No interactions were observed for the amino and carboxy termini.

HA-YK Peptide with DR1:

The binding of the HA-YK peptide (Ala-Ala-Tyr-Ala-Ala-Ala-Ala-Ala-Ala-Lys-Ala-Ala, SEQ ID NO:2) to the DR1 model was tested. In aligning the peptide in the cleft, it was deemed logical to insert the tyrosine residue into the hydrophobic region of the binding cleft. The lysine would then be in position to interact with the hydrophilic groups in the other half of the cleft. The resulting peptide orientation is the opposite of that used for the HA and the CS3 (defined below) peptides. With the peptide oriented as described, the final docking position for the peptide was unclear. The hydrophobic pocket is quite large, and, at least in this model, could accommodate the peptide tyrosine in a number of positions by sliding the peptide lengthwise through the cleft. However, repositioning the peptide also repositions the lysine. There were primarily two positions for the lysine: one with the lysine inside the cleft and the second with it outside. Of the two positions, the former was the lower in energy by 46 kcal/mol and had the greater number of interactions with the protein (11 vs. 7). Thus, the preferred orientation of the peptide appears to be with the lysine inside the binding cleft region.

CS3 Subunit Pilin Peptide with DR1:

The suspected T-cell epitope for CS3 pilus subunit 63–78 (Ser-Lys-Asn-Gly-Thr-Val-Thr-Trp-Ala-His-Glu-Thr-Asn-Asn-Ser-Ala, SEQ ID NO:3) was modeled with the DR1 molecule. The peptide was inserted with lysine inside the cleft in the hydrophilic region. This placed the Thr 5 in the center of the binding cleft and the tryptophane (residue 8) near the hydrophobic region. The resulting minimized model had ten interactions between the peptide and the protein, three interactions with the peptide backbone and five with the peptide side chains. The remaining two were with the amino terminal of the peptide. All of the interactions were in either the first three residues, His 10 or Glu 11 in the peptide. No interactions were observed in the center of the cleft or residues four through nine.

CFA/1 with DR1:

A peptide identified as CFA/1 (colonization factor antigen) (Val-Gly-Lys-Asn-Ile-Thr-Val-Thr-Ala-Ser-Val-Asp-Pro, SEQ ID NO:4) was prepared and an attempt was made to "fit" the molecule into the cleft of the DR1. The lysine at position 3 prevented insertion of the peptide.

Results:

The peptides chosen to dock in the DR1 model are shown in Table 1. The peptides were docked manually in several orientations into the DR1 model. The peptides were then tested in biological binding assays with the following results:

TABLE I

| Peptide | Molecular Model predicted binding | Binding in the bioassay |
|---|---|---|
| HA (influenza hemagglutinin) | Yes | Yes |
| HA-YK (synthetic peptide) | Yes | Yes |
| CS3 Pilin subunit | Yes | Yes |
| CFA/1 | No | No |

(2) INFORMATION FOR SEQ ID NO:2:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:2:

Ala Ala Tyr Ala Ala Ala Ala Ala Ala Lys Ala Ala
1               5                   10

(2) INFORMATION FOR SEQ ID NO:3:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:3:

Ser Lys Asn Gly Thr Val Thr Trp Ala His Glu Thr Asn Asn Ser Ala
1               5                   10                  15

(2) INFORMATION FOR SEQ ID NO:4:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:4:

Val Gly Lys Asn Ile Thr Val Thr Ala Ser Val Asp Pro
1               5                   10

(2) INFORMATION FOR SEQ ID NO:5:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:5:

Asp Glu Tyr Gly Leu Gly Arg Leu Val Asn Thr Ala Asp
1               5                  10

(2) INFORMATION FOR SEQ ID NO:6:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:6:

Ile Ile Tyr Gln Ile Val Asp Glu Lys Gly Lys Lys Lys
1               5                  10

(2) INFORMATION FOR SEQ ID NO:7:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:7:

Leu Asn Tyr Thr Ser Gly Glu Lys Lys Ile Ser Pro Gly
1               5                  10

(2) INFORMATION FOR SEQ ID NO:8:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:8:

Trp Gln Tyr Lys Ser Leu Asp Val Asn Val Asn Ile Glu
1               5                  10

(2) INFORMATION FOR SEQ ID NO:9:

(i) SEQUENCE CHARACTERISTICS:
            (A) LENGTH: 13 amino acids

```
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:9:

Gln Leu Tyr Thr Val Glu Met Thr Ile Pro Ala Gly Val
1               5                   10

(2) INFORMATION FOR SEQ ID NO:10:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:10:

Thr Ser Tyr Thr Phe Ser Ala Ile Tyr Thr Gly Gly Glu
1               5                   10

(2) INFORMATION FOR SEQ ID NO:11:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:11:

Gly Glu Tyr Pro Asn Ser Gly Tyr Ser Ser Gly Thr Tyr
1               5                   10

(2) INFORMATION FOR SEQ ID NO:12:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:12:
```

```
Gly Thr Tyr Ala Gly His Leu Thr Val Ser Phe Tyr Ser
1               5                   10
```

(2) INFORMATION FOR SEQ ID NO:13:

(i) SEQUENCE CHARACTERISTICS:
        (A) LENGTH: 181 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:13:

```
Gly Ser His Ser Met Arg Tyr Phe Tyr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Arg Asn Thr
    50                  55                  60

Arg Asn Val Lys Ala Gln Ser Gln Thr Asp Arg Val Asp Leu Gly Thr
65                  70                  75                  80

Leu Arg Gly Tyr Tyr Asn Gln Ser Glu Ala Gly Ser His Thr Ile Gln
                85                  90                  95

Met Met Tyr Gly Cys Asp Val Gly Ser Asp Gly Arg Phe Leu Arg Gly
            100                 105                 110

Tyr Arg Gln Asp Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
130                 135                 140

His Lys Trp Glu Ala Ala His Val Ala Glu Gln Trp Arg Ala Tyr Leu
145                 150                 155

Glu Gly Thr Cys Val Glu Trp Leu Arg Arg Tyr Leu Glu Asn Gly Lys
                165                 170                 175

Glu Thr Leu Gln Arg
            180
```

(2) INFORMATION FOR SEQ ID NO:14:

(i) SEQUENCE CHARACTERISTICS:
        (A) LENGTH: 81 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:14:

```
Ile Lys Glu Glu His Val Ile Ile Gln Ala Glu Phe Tyr Leu Asn Pro
```

-continued

```
  1               5                  10                 15
Asp Gln Ser Gly Glu Met Phe Asp Phe Asp Gly Asp Glu Ile Phe
              20                  25                 30

His Val Asp Met Ala Lys Lys Glu Thr Val Trp Arg Leu Glu Glu Phe
              35                  40                 45

Gly Arg Phe Ala Ser Phe Glu Ala Gln Gly Ala Leu Ala Asn Ile Ala
              50                  55                 60

Val Asp Lys Ala Asn Leu Glu Ile Met Thr Lys Arg Ser Asn Tyr Thr
              65                  70                 75

Pro Ile
 80
```

(2) INFORMATION FOR SEQ ID NO:15:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: peptide (iii) HYPOTHETICAL: No (iv) ANTI-SENSE: NO (v) FRAGMENT TYPE: C-terminal (xi) SEQUENCE DESCRIPTION: SEQ ID NO:15:

```
Gly Asp Thr Arg Pro Arg Phe Leu Trp Gln Leu Lys Phe Glu Cys His
 1               5                  10                 15

Phe Phe Asn Gly Thr Glu Arg Val Arg Leu Leu Glu Arg Cys Ile Tyr
              20                  25                 30

Asn Gln Glu Glu Ser Val Arg Phe Asp Ser Asp Val Gly Glu Tyr Arg
              35                  40                 45

Ala Val Thr Glu Leu Gly Arg Pro Asp Ala Glu Tyr Trp Asn Ser Gln
              50                  55                 60

Lys Asp Leu Leu Glu Gln Arg Arg Arg Ala Val Asp Thr Tyr Cys Arg
 65                              70                 75                 80

His Met Tyr Gly Val Gly Glu Ser Phe Thr Val Gln Arg Arg Val His
                     85                  90                 95
```

We claim:

1. An immunogenic composition comprising: a CS3 peptide, said peptide selected from CS3 consisting of the amino acid sequence of SKNGTVTWAHETNNSA, Seq. ID No: 3.

2. The immunogenic composition of claim 1, wherein said composition is immunogenic against pathogenic microorganisms and neoplasms.

3. The immunogenic composition of claim 1, wherein said composition is immunogenic against Enterotoxigenic *E. coli*.

4. The immunogenic composition of claim 1, wherein said composition is combined with an immunologically acceptable carrier.

5. The immunogenic composition of claim 4 wherein said immunologically acceptable carrier comprises encapsulating microspheres.

6. The immunogenic composition of claim 5, wherein said encapsulation microspheres comprise biodegradable biocompatible poly(DL-lactide-co-glycolide) as a bulk matrix.

7. The immunogenic composition of claim 1 wherein said peptide is a synthetic peptide.

8. The immunogenic composition of claim 1, wherein when said peptide is minimized, the minimized peptide binds to a Class II MHC receptor DR1.

9. An immunogenic composition comprising: a CS3 peptide with an amino acid sequence of SKNGTVTWAHETNNSA, Seq. ID No: 3, wherein said peptide is not a whole CS3 protein.

10. The immunogenic composition of claim 9, wherein when said peptide is minimized, the minimized peptide binds to a Class II MHC receptor DR1.

11. The immunogenic composition of claim 8, wherein when said peptide binds to the Class II receptor DR1, it inhibits the binding of HA residues 307–319.

12. The immunogenic composition of claim 10, wherein said peptide binds to the Class II receptor DR1, it inhibits the binding of HA residues 307–319.

* * * * *